US008932601B2

(12) United States Patent
Medof et al.

(10) Patent No.: US 8,932,601 B2
(45) Date of Patent: Jan. 13, 2015

(54) HYBRID AND CHIMERIC POLYPEPTIDES THAT REGULATE ACTIVATION OF COMPLEMENT

(75) Inventors: M. Edward Medof, Pepper Pike, OH (US); Lisa Kuttner-Kondo, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 13/306,631

(22) Filed: Nov. 29, 2011

(65) Prior Publication Data
US 2012/0226020 A1 Sep. 6, 2012

Related U.S. Application Data

(63) Continuation of application No. 10/597,373, filed as application No. PCT/IB2005/050257 on Jan. 21, 2005, now Pat. No. 8,124,097.

(60) Provisional application No. 60/537,860, filed on Jan. 21, 2004.

(51) Int. Cl.
*C07K 19/00* (2006.01)
*C07K 14/705* (2006.01)
*C07K 14/745* (2006.01)

(52) U.S. Cl.
CPC ................ *C07K 14/70596* (2013.01)
USPC ...................... 424/192.1; 530/350

(58) Field of Classification Search
None
See application file for complete search history.

(56) References Cited

U.S. PATENT DOCUMENTS

| | | | |
|---|---|---|---|
| 4,774,180 A | 9/1988 | Toth et al. | |
| 5,212,071 A | 5/1993 | Fearon et al. | |
| 5,256,642 A * | 10/1993 | Fearon et al. ............... | 514/14.9 |
| 5,472,939 A | 12/1995 | Fearon et al. | |
| 5,514,787 A | 5/1996 | Atkinson | |
| 5,552,381 A | 9/1996 | Atkinson | |
| 5,624,837 A | 4/1997 | Fodor et al. | |
| 5,627,264 A | 5/1997 | Fodor et al. | |
| 5,679,546 A | 10/1997 | Ko et al. | |
| 5,703,046 A | 12/1997 | Atkinson | |
| 5,763,224 A | 6/1998 | Caras et al. | |
| 5,833,989 A | 11/1998 | Mossakowska et al. | |
| 5,843,778 A | 12/1998 | Rosengard et al. | |
| 5,851,528 A | 12/1998 | Ko et al. | |
| 5,856,297 A | 1/1999 | Fearon et al. | |
| 5,866,402 A | 2/1999 | Innis et al. | |
| 5,981,481 A | 11/1999 | Fearon et al. | |
| 6,140,472 A | 10/2000 | Rosengard et al. | |
| 6,218,520 B1 | 4/2001 | Atkinson | |
| 6,280,732 B1 | 8/2001 | Caras et al. | |
| 6,316,604 B1 | 11/2001 | Fearon et al. | |
| 6,458,360 B1 | 10/2002 | Fearon et al. | |
| 6,713,606 B1 * | 3/2004 | Smith et al. ................ | 530/350 |
| 6,897,290 B1 | 5/2005 | Atkinson et al. | |
| 8,007,804 B2 * | 8/2011 | Tomlinson et al. ......... | 424/178.1 |
| 2002/0197606 A1 * | 12/2002 | Craig ........................... | 435/6 |
| 2006/0246066 A1 | 11/2006 | Morgan et al. | |

FOREIGN PATENT DOCUMENTS

| | | | |
|---|---|---|---|
| WO | 9508570 A1 | 3/1995 | |
| WO | WO 95/08570 | * | 3/1995 |
| WO | WO 00/61752 | * | 10/2000 |

OTHER PUBLICATIONS

Song et al, J Clin Investigation 111(12): 1875-1885.*
Yu et al, Investigative Ophthalmology & Visual Science 49(2): 522-527, Feb. 2008.*
Witte et al, Cancer and Metastasis Reviews 17: 155-161, 1998.*
Smith et al, J Immunology 154: 2226-2236, 1995.*
Harris et al, J Biol Chemistry 278(38): 36068-36076, Sep. 2003.*
Lublin et al, J Exp Med 168: 181-194, Jul. 1988.*
Smith et al., Biochemical Society Transactions 30(6): 1037-1041, 2002.*
Fraser et al., J Bio Chem 278(49): 48921-48927, 2003.*
Krych-Goldberg et al., J Biol Chem 274(44): 31160-31168, 1999.*
Kuttner-Kondo and Medof; "Engineering of DAF-CR1 and DAF-MCP hybrid proteins for enhanced function;" Abstracts/Molecular Immunology; 2004; pp. 264-265 (Abstract #138); vol. 41.
Weisman et al.; "Soluble human complement receptor type 1: in vivo inhibitor of complement suppressing post-ischemic myocardial inflammation and necrosis;" Science; Jul. 13, 1990; pp. 146-151; vol. 249.
Kalli et al.; "Mapping of the C3b-binding site of CR1 and construction of a (CR1)2-F(ab')2 chimeric complement inhibitor;" J. Exp. Med.; Dec. 1991; pp. 1451-1460; vol. 174; The Rockefeller University Press.
Song et al.; "Complement receptor 2-mediated targeting of complement inhibitors to sites of complement activation;" The Journl of Clinical Investigation; Jun. 2003; pp. 1875-1885; vol. 111, No. 12.
Fodor et al.; "A novel bifunctional chimeric complement inhibitor that regulates C3 convertase and formation of the.membrane attack complex;" The Journal of Immunology; 1995; pp. 4135-4138; vol. 155; The American Association of Immunologists.

(Continued)

*Primary Examiner* — Phuong Huynh
(74) *Attorney, Agent, or Firm* — Tarolli, Sundheim, Covell & Tummino LLP

(57) ABSTRACT

A hybrid complement-regulating protein comprises a first functional unit of a first complement regulatory protein having complement regulating properties, a first spacer sequence of at least about 200 amino acids encoding a polypeptide that does not exhibit complement regulating properties and at least a second functional unit attached to the spacer sequence. The second functional unit may be a polypeptide providing a functional unit of a second complement regulatory protein, a polypeptide derived from an immunoglobulin, or a polypeptide that enhances binding of the protein to an animal cell. The hybrid protein may also contain a second spacer sequence and a third functional unit of a complement regulatory protein, a polypeptide derived from an immunoglobulin, and a polypeptide that enhances binding of the protein to an animal cell. The optional third functional unit may be the same or different from the first or second functional units.

4 Claims, 25 Drawing Sheets

(56) References Cited

OTHER PUBLICATIONS

Higgins et al.; "A soluble chimeric complement inhibitory protein that possesses both decay-accelerating and factor I cofactor activities;" The Journal of Immunology; 1997; pp. 2872-2881; vol. 158; The American Association of Immunologists; U.S.A.

Salerno et al.; "A soluble chimeric inhibitor of C3 and C5 convertases, complement activation blocker-2, prolongs graft survival in pig-to-rhesus monkey heart transplantation;" Xenotransplantation; 2002; pp. 125-134; vol. 9; United Kingdom.

Kroshus et al.; "A recombinant soluble chimeric complement inhibitor composed of human CD46 and CD55 reduces acute cardiac tissue injury in models of pig-to-human heart transplantation;" Transplantation; Jun. 15, 2000; pp. 2282-2289; vol. 69, No. 11; Lippincott Williams & Wilkins, Inc.; U.S.A.

Li et al.; "Pharmacokinetics and safety of TP10, soluble complement receptor 1, in infants undergoing cardiopulmonary bypass;" American Heart Journal; Jan. 2004; pp. 173-180; vol. 147; Elsevier Inc., U.S.A.

Lazar et al.;"Soluble human complement receptor 1 limits ischemic damage in cardiac surgery patients at high risk requiring cardiopulmonary bypass;" Circulation; Sep. 14, 2004; pp. 11274-11279; Issue No. 0009-7322; vol. 110 (Suppl II); The American Heart Association; Dallas, TX U.S.A.

Schmid et al.; "TP20 is superior to TP10 in reducing ischemia/reperfusion injury in rat lung grafts;" Transplantation Proceedings; 2001; pp. 948-949; vol. 33; Elsevier Science Inc.; New York, NY U.S.A.

Zimmerman et al.; "Phase I trial of the recombinant soluble complement receptor 1 in acute lung injury and acute respiratory distress syndrome;" Crit Care Med; 2000; pp. 3149-3154; vol. 28, No. 9; lippincott Williams & Wilkins; U.S.A.

Couser et al.; "The effects of soluble recombinant complement receptor 1 on complement-mediated experimental glomerulonephritis;" Journal of the American Society of Nephrology; 1995; pp. 1888-1894; vol. 5, No. 11; The American Society of Nephrology; U.S.A.

Krych-Goldberg et al.; "Synergy between two active sites of human complement receptor type 1 (CD35) in complement regulation: implications for the structure of the classical pathway C3 convertase and generation of more D potent inhibitors;" Journal of Immunology; 2005; pp. 4528-4535; vol. 175; The American Association of Immunologists, Inc. U.S.A.

Harris et al.; "Coupling complement regulators to immunoglobulin domains generates effective anti-complement reagents with extended half-life in vivo;" Clinical and Experimental Immunology; 2002; pp. 198-207; vol. 129; Blackwell Science.

Harris et al.; "Generation of anti-complement "prodrugs": cleavable reagents for specific delivery of complement regulators to disease sites;" Journal of Biological Chemistry; Sep. 19, 2003; pp. 36068-36076; vol. 278, No. 38; The American Society for Biochemistry and Molecular Biology. Inc.; U.S.A.

Iwata et al.; "Expression of a hybrid complement regulatory protein, membrane cofactor protein decay accelerating factor on Chinese Hamster Ovary. Comparison of its regulatory effect with those of decay accelerating factor and membrane cofactor protein;" Journal of Immunology; 1994; pp. 3436-3444; vol. 152; The American Association of Immunologists; U.S.A.

Christiansen et al.; "Engineering of recombinant soluble CD46: an inhibitor of complement activation;" Immunology; 1996; pp. 348-354; vol. 87; Blackwell Science Ltd.

Rinder et al.; "Role of C3 cleavage in monocyte activation during extracorporeal circulation;" Circulation; Aug. 3, 1999; pp. 553-558; vol. 100; American Heart Association, Inc.; Dallas, TX U.S.A.

Souza et al; "APT070 (Mirococept), a membrane-localised complement inhibitor, inhibits inflammatory responses that follow intestinal ischaemia and reperfusion injury;" British Journal of Pharmacology; 2005; pp. 1027-1034; vol. 145; Nature Publishing Group.

Lam et al.; "The effect of soluble complement receptor type 1 on acute humoral xenograft rejection in hDAF-transgenic pig-to-primate life-supporting kidney xenografts;" Xenotransplantation; 2005; pp. 20-29; vol. 12; Singapore.

Henry et al.; "Complement activation is responsible for acute toxicities in rhesus monkeys treated with a phosphorothioate oligodeoxynucleotide;" International Immunopharmacology; 2002, pp. 1657-1666; Elsevier Science BV.

Von Dobschuetz et al.; "Soluble complement receptor 1 preserves endothelial barrier function and microcirculation in postischemic pancreatitis in the rat;" American Journal of Physiology—Gastrointestinal Liver Physiology; Dec. 23, 2003; pp. 791-796; vol. 286; American Physiological Society; Bethesda, MD U.S.A.

Yazdanbakhsh, Karina; "Development of complement therapeutics for inhibition of immune-mediated red cell destruction;" Transfusion; Aug. 2005; pp. 122S-1295; vol. 45.

Xoma Ltd.; "MLN01 and CAB-2 with Millennium Pharmaceuticals, Inc.;" Press Release; May 15, 2003; p. 2; U.S.A.

Biospace Beat; "XOMA (XOMA) and Millennium Pharmaceuticals, Inc. (California) (MLNM) announce initiation of phase I clinical trial of MLN2222—A.K.A. CAB-2—a novel complement inhibitor;" Press Release; Dec. 18, 2003; U.S.A.

Harris, C.L., et al., "Tailoring anti-complement therapeutics", Biochemical Society Transactions 30(6): 1019-1026, 2002.

Seffernick, Jennifer L., et al., "Melamine Deaminase and Atrazine Chlorohydrolase: 98 Percent Identical but functionally different", Journal of Bacteriology, Apr. 2001, p. 2405-2410, vol. 183, No. 8.

\* cited by examiner

SEQ. ID NO:1

```
MTVARPSVPAALPLLGELPRLLLLVLLCLPAVWGDCGLPPDVPNAQPALE    50
GRTSFPEDTVITYKCEESFVKIPGEKDSVICLKGSQWSDIEEFCNRSCEV   100
PTRLNSASLKQPYITQNYFPVGTVVEYECRPGYRREPSLSPKLTCLQNLK   150
WSTAVEFCKKKSCPNPGEIRNGQIDVPGGILFGATISFSCNTGYKLFGST   200
SSFCLISGSSVQWSDPLPECREIYCPAPPQIDNGIIQGERDHYGYRQSVT   250
YACNKGFTMIGEHSIYCTVNNDEGEWSGPPPECRGKSLTSKVPPTVQKPT   300
TVNVPTTEVSPTSQKTTTKTTTPNAQATRSTPVSRTTKHFHETTPNKGSG   350
TTSGTTRLLSGHTCFTLTGLLGTLVTMGLLT
```

Fig. 1A

SEQ. ID NO:2

```
   1 ccgctgggcg tagctgcgac tcggcggagt cccggcggcg cgtccttgtt ctaacccggc
  61 gcgccatgac cgtcgcgcgg ccgagcgtgc ccgcggcgct gccccctcctc ggggagctgc
 121 cccggctgct gctgctggtg ctgttgtgcc tgccggccgt gtggggtgac tgtggccttc
 181 ccccagatgt acctaatgcc cagccagctt ggaaggccg tacaagtttt cccgaggata
 241 ctgtaataac gtacaaatgt gaagaaagct ttgtgaaaat tcctggcgag aaggactcag
 301 tgatctgcct taagggcagt caatggtcag atattgaaga gttctgcaat cgtagctgcg
 361 aggtgccaac aaggctaaat ctgcatccc tcaaacagcc ttatatcact cagaattatt
 421 ttccagtcgg tactgttgtg gaatatgagt gccgtccagg ttacagaaga gaaccttctc
 481 tatcaccaaa actaacttgc cttcagaatt taaaatggtc cacagcagtc gaattttgta
 541 aaaagaaatc atgccctaat ccgggagaaa tacgaaatgg tcagattgat gtaccaggtg
 601 gcatattatt tggtgcaacc atctcctct catgtaacac agggtacaaa ttatttggct
 661 cgacttctag tttttgtctt atttcaggca gctctgtcca gtggagtgac ccgttgccag
 721 agtgcagaga aatttattgt ccagcaccac cacaaattga caatgaata attcaagggg
 781 aacgtgacca ttatggatat agacagtctg taacgtatgc atgtaataaa ggattcacca
 841 tgattggaga gcactctatt tattgtactg tgaataatga tgaaggagag tggagtggcc
 901 caccacctga atgcagagga aaatctctaa cttccaaggt cccaccaaca gttcagaaac
 961 ctaccacagt aaatgttcca actacagaag tctcaccaac ttctcagaaa accaccacaa
1021 aaaccaccac accaaatgct caagcaacac ggagtacacc tgtttccagg acaaccaagc
1081 attttcatga acaaccccca aataaggaa gtggaaccac ttcaggtact acccgtcttc
1141 tatctgggca cacgtgtttc acgttgacag gttgcttgg gacgctagta accatgggct
1201 tgctgactta gccaagaag agttaagaag aaaatacaca aagtataca gactgttcct
1261 agtttcttag acttatctgc atattggata aaataaatgc aattgtgctc ttcatttagg
1321 atgctttcat tgtctttaag atgtgttagg aatgtcaaca gagcaaggag aaaaaaggca
1381 gtcctggaat cacattctta gcacacctac acctcttgaa aatagaacaa cttgcagaat
1441 tgagagtgat tcctttccta aaagtgtaag aaagcataga gatttgttcg tatttagaat
1501 gggatcacga ggaaaagaga aggaaagtga tttttttcca caagatctgt aatgttattt
1561 ccacttataa aggaaataaa aaatgaaaaa cattatttgg atatcaaaag caaataaaaa
1621 cccaattcag tctcttctaa gcaaaattgc taaagagaga tgaaccacat tataaagtaa
1681 tctttggctg taaggcattt tcatctttcc ttcgggttgg caaaatattt taaaggtaaa
1741 acatgctggt gaaccagggg tgttgatggt gataagggag gaatatagaa tgaaagactg
1801 aatcttcctt tgttgcacaa atagagtttg gaaaaagcct gtgaaaggtg tcttctttga
1861 cttaatgtct ttaaaagtat ccagagatac tacaatatta acataagaaa agattatata
1921 ttatttctga atcgagatgt ccatagtcaa atttgtaaat cttattcttt tgtaatattt
1981 atttatattt atttatgaca gtgaacattc tgattttaca tgtaaaacaa gaaagttga
2041 agaagatatg tgaagaaaaa tgtattttc ctaaatagaa ataaatgatc ccatttttg
2101 gt
```

Fig. 1B

SEQ. ID NO:3

```
MCLGRMGASSPRSPEPVGPPAPGLPFCCGGSLLAVVVLLALPVAWGQCNA    50
PEWLPFARPTNLTDEFEFPIGTYLNYECRPGYSGRPFSIICLKNSVWTGA   100
KDRCRRKSCRNPPDPVNGMVHVIKGIQFGSQIKYSCTKGYRLIGSSSATC   150
IISGDTVIWDNETPICDRIPCGLPPTITNGDFISTNRENFHYGSVVTYRC   200
NPGSGGRKVFELVGEPSIYCTSNDDQVGIWSGPAPQCIIPNKCTPPNVEN   250
GILVSDNRSLFSLNEVVEFRCQPGFVMKGPRRVKCQALNKWEPELPSCSR   300
VCQPPPDVLHAERTQRDKDNFSPGQEVFYSCEPGYDLRGAASMRCTPQGD   350
WSPAAPTCEVKSCDDFMGQLLNGRVLFPVNLQLGAKVDFVCDEGFQLKGS   400
SASYCVLAGMESLWNSSVPVCEQIFCPSPPVIPNGRHTGKPLEVFPFGKA   450
VNYTCDPHPDRGTSFDLIGESTIRCTSDPQGNGVWSSPAPRCGILGHCQA   500
PDHFLFAKLKTQTNASDFPIGTSLKYECRPEYYGRPFSITCLDNLVWSSP   550
KDVCKRKSCKTPPDPVNGMVHVITDIQVGSRINYSCTTGHRLIGHSSAEC   600
ILSGNAAHWSTKPPICQRIPCGLPPTIANGDFISTNRENFHYGSVVTYRC   650
NPGSGGRKVFELVGEPSIYCTSNDDQVGIWSGPAPQCIIPNKCTPPNVEN   700
GILVSDNRSLFSLNEVVEFRCQPGFVMKGPRRVKCQALNKWEPELPSCSR   750
VCQPPPDVLHAERTQRDKDNFSPGQEVFYSCEPGYDLRGAASMRCTPQGD   800
WSPAAPTCEVKSCDDFMGQLLNGRVLFPVNLQLGAKVDFVCDEGFQLKGS   850
SASYCVLAGMESLWNSSVPVCEQIFCPSPPVIPNGRHTGKPLEVFPFGKA   900
VNYTCDPHPDRGTSFDLIGESTIRCTSDPQGNGVWSSPAPRCGILGHCQA   950
PDHFLFAKLKTQTNASDFPIGTSLKYECRPEYYGRPFSITCLDNLVWSSP  1000
KDVCKRKSCKTPPDPVNGMVHVITDIQVGSRINYSCTTGHRLIGHSSAEC  1050
ILSGNTAHWSTKPPICQRIPCGLPPTIANGDFISTNRENFHYGSVVTYRC  1100
NLGSRGRKVFELVGEPSIYCTSNDDQVGIWSGPAPQCIIPNKCTPPNVEN  1150
GILVSDNRSLFSLNEVVEFRCQPGFVMKGPRRVKCQALNKWEPELPSCSR  1200
VCQPPPEILHGEHTPSHQDNFSPGQEVFYSCEPGYDLRGAASLHCTPQGD  1250
WSPEAPRCAVKSCDDFLGQLPHGRVLFPLNLQLGAKVSFVCDEGFRLKGS  1300
SVSHCVLVGMRSLWNNSVPVCEHIFCPNPPAILNGRHTGTPSGDIPYGKE  1350
ISYTCDPHPDRGMTFNLIGESTIRCTSDPHGNGVWSSPAPRCELSVRAGH  1400
CKTPEQFPPFASPTIPINDFEFPVGTSLNYECRPGYFGKMFSISCLENLVW  1450
SSVEDNCRRKSCGPPPEPFNGMVHINTDTQFGSTVNYSCNEGFRLIGSPS  1500
TTCLVSGNNVTWDKKAPICEIISCEPPPTISNGDFYSNNRTSFHNGTVVT  1550
YQCHTGPDGEQLFELVGERSIYCTSKDDQVGVWSSPPPRCISTNKCTAPE  1600
VENAIRVPGNRSFFSLTEIIRFRCQPGFVMGSHTVQCQTNGRWGPKLPH   1650
CSRVCQPPPEILHGEHTLSHQDNFSPGQEVFYSCEPSYDLRGAASLHCTP  1700
QGDWSPEAPRCTVKSCDDFLGQLPHGRVLLPLNLQLGAKVSFVCDEGFRL  1750
KGRSASHCVLAGMKALWNSSVPVCEQIFCPNPPAILNGRHTGTPFGDIPY  1800
GKEISYACDTHPDRGMTFNLIGESSIRCTSDPQGNGVWSSPAPRCELSVP  1850
AACPHPPKIQNGHYIGGHVSLYLPGMTISYTCDPGYLLVGKGFIFCTQG   1900
IWSQLDHYCKEVNCSFPLFMNGISKELEMKKVYHYGDYVTLKCEDGYTLE  1950
GSPWSQCQADDRWDPPLAKCTSRAHDALIVGTLSGTIFFILLIIFLSWII  2000
LKHRKGNNAHENPKEVAIHLHSQGGSSVHPRTLQTNEENSRVLP
```

Fig. 2

SEQ. ID NO:4

```
   1 cgtggtttgt agatgtgctt ggggagaatg ggggcctctt ctccaagaag cccggagcct
  61 gtcgggccgc cggcgcccgg tctcccctt c tgctgcggag gatccctgct ggcggttgtg
 121 gtgctgcttg cgctgccggt ggcctggggt caatgcaatg cccagaatg gcttccattt
 181 gccaggccta ccaacctaac tgatgagttt gagtttccca ttgggacata tctgaactat
 241 gaatgccgcc ctggttattc cggaagaccg ttttctatca tctgcctaaa aaactcagtc
 301 tggactggtg ctaaggacag gtgcagacgt aaatcatgtc gtaatcctcc agatcctgtg
 361 aatggcatgg tgcatgtgat caaaggcatc cagttcggat cccaaattaa atattcttgt
 421 actaaaggat accgactcat tggttcctcg tctgccacat gcatcatctc aggtgatact
 481 gtcatttggg ataatgaaac acctatttgt gacagaattc cttgtgggct acccccccacc
 541 atcaccaatg gagatttcat tagcaccaac agagagaatt ttcactatga tcagtggtg
 601 acctaccgct gcaatcctgg aagcggaggg agaaaggtgt tgagcttgt gggtgagccc
 661 tccatatact gcaccagcaa tgacgatcaa gtgggcatct ggagcggccc cgcccctcag
 721 tgcattatac ctaacaaatg cacgcctcca aatgtggaaa atggaatatt ggtatctgac
 781 aacagaagct tatttcctt aaatgaagtt gtggagttta ggtgtcagcc tggctttgtc
 841 atgaaggac cccgccgtgt gaagtgccag gccctgaaca aatgggagcc ggagctacca
 901 agctgctcca gggtatgtca gccacctcca gatgtcctgc atgctgagcg tacccaaagg
 961 gacaaggaca acttttcacc tgggcaggaa gtgttctaca gctgtgagcc cggctacgac
1021 ctcagagggg ctgcgtctat gcgctgcaca ccccaggag actggagccc tgcagccccc
1081 acatgtgaag tgaaatcctg tgatgacttc atggggccaac ttcttaatgg ccgtgtgctta
1141 tttccagtaa atctccagct tggagcaaaa gtggattttg tttgtgatga aggatttcaa
1201 ttaaaaggca gctctgctag ttactgtgtc ttggctgaa tggaaagcct ttggaatagc
1261 agtgttccag tgtgtgaaca aatctttgt ccaagtcctc cagttattcc taatgggaga
1321 cacacaggaa aacctctgga agtctttccc tttggaaaag cagtaaatta cacatgcgac
1381 ccccacccag acagagggac gagcttcgac ctcattggag agcaccat ccgctgcaca
1441 agtgaccctc aagggaatgg ggttggagc agccctgccc ctcgctgtgg aattctgggt
1501 cactgtcaag ccccagatca ttttctgttt gccaagttga aaacccaaac caatgcatct
1561 gactttccca ttgggacatc tttaaagtac gaatgccgtc ctgagtacta cgggaggcca
1621 ttctctatca catgtctaga taacctggtc tggtcaagtc ccaaagatgt ctgtaaacgt
1681 aaatcatgta aaactcctcc agatccagtg aatggcatgg tgcatgtgat cacagacatc
1741 caggttggat ccagaatcaa ctattcttgt actacagggc accgactcat tggtcactca
1801 tctgctgaat gtatcctctc gggcaatgct gcccattgga gcacgaagcc gccaatttgt
1861 caacgaattc cttgtgggct accccccacc atcgccaatg gagatttcat tagcaccaac
1921 agagagaatt ttcactatga tcagtggtg acctaccgct gcaatcctgg aagcggaggg
1981 agaaaggtgt tgagcttgt gggtgagccc tccatatact gcaccagcaa tgacgatcaa
2041 gtgggcatct ggagcggccc ggcccctcag tgcattatac ctaacaaatg cacgcctcca
2101 aatgtggaaa atggaatatt ggtatctgac aacagaagct tatttcctt aaatgaagtt
2161 gtggagttta ggtgtcagcc tggctttgtc atgaaggac cccgccgtgt gaagtgccag
2221 gccctgaaca aatgggagcc ggagctacca agctgctcca gggtatgtca gccacctcca
2281 gatgtcctgc atgctgagcg tacccaaagg gacaaggaca acttttcacc cgggcaggaa
2341 gtgttctaca gctgtgagcc cggctatgac ctcagagggg ctgcgtctat gcgctgcaca
2401 ccccaggag actggagccc tgcagccccc acatgtgaag tgaaatcctg tgatgacttc
2461 atgggccaac ttcttaatgg ccgtgtgcta tttccagtaa atctccagct tggagcaaaa
2521 gtggattttg tttgtgatga aggatttcaa ttaaaaggca gctctgctag ttattgtgtc
2581 ttggctgaa tggaaagcct ttggaatagc agtgttccag tgtgtgaaca aatctttgt
2641 ccaagtcctc cagttattcc taatgggaga cacacaggaa aacctctgga agtctttccc
2701 tttggaaaag cagtaaatta cacatgcgac ccccacccag acagagggac gagcttcgac
2761 ctcattggag agcaccat ccgctgcaca agtgaccctc aagggaatgg ggtttggagc
2821 agccctgccc ctcgctgtgg aattctgggt cactgtcaag ccccagatca ttttctgttt
2881 gccaagttga aaacccaaac caatgcatct gactttccca ttgggacatc tttaaagtac
2941 gaatgccgtc ctgagtacta cgggaggcca ttctctatca catgtctaga taacctggtc
3001 tggtcaagtc ccaaagatgt ctgtaaacgt aaatcatgta aaactcctcc agatccagtg
3061 aatggcatgg tgcatgtgat cacagacatc caggttggat ccagaatcaa ctattcttgt
```

Fig. 3

```
3121 actacagggc accgactcat tggtcactca tctgctgaat gtatcctctc aggcaatact
3181 gcccattgga gcacgaagcc gccaatttgt caacgaattc cttgtgggct acccccaacc
3241 atcgccaatg gagatttcat tagcaccaac agagagaatt ttcactatgg atcagtggtg
3301 acctaccgct gcaatcttgg aagcagaggg agaaaggtgt ttgagcttgt gggtgagccc
3361 tccatatact gcaccagcaa tgacgatcaa gtgggcatct ggagcggccc cgcccctcag
3421 tgcattatac ctaacaaatg cacgcctcca aatgtggaaa atggaatatt ggtatctgac
3481 aacagaagct tattttcctt aaatgaagtt gtggagttta ggtgtcagcc tggctttgtc
3541 atgaaaggac cccgccgtgt gaagtgccag gccctgaaca aatgggagcc agagttacca
3601 agctgctcca gggtgtgtca gccgcctcca gaaatcctgc atggtgagca tacccccaagc
3661 catcaggaca acttttcacc tgggcaggaa gtgttctaca gctgtgagcc tggctatgac
3721 ctcagagggg ctgcgtctct gcactgcaca cccagggag actggagccc tgaagcccg
3781 agatgtgcag tgaaatcctg tgatgacttc ttgggtcaac tccctcatgg ccgtgtgcta
3841 tttccactta atctccagct tggggcaaag gtgtcctttg tctgtgatga agggtttcgc
3901 ttaaagggca gttccgttag tcattgtgtc ttggttggaa tgagaagcct ttggaataac
3961 agtgttcctg tgtgtgaaca tatctttttgt ccaaatcctc cagctatcct aatgggaga
4021 cacacaggaa ctccctctgg agatattccc tatggaaaag aaatatctta cacatgtgac
4081 ccccacccag acagagggat gaccttcaac ctcattgggg agagcaccat ccgctgcaca
4141 agtgaccctc atgggaatgg ggtttggagc agccctgccc ctcgctgtga actttctgtt
4201 cgtgctggtc actgtaaaac cccagagcag tttccatttg ccagtcctac gatcccaatt
4261 aatgactttg agtttccagt cgggacatct ttgaattatg aatgccgtcc tgggtatttt
4321 gggaaaatgt tctctatctc ctgcctagaa aacttggtct ggtcaagtgt tgaagacaac
4381 tgtagacgaa aatcatgtgg acctccacca gaacccttca atggaatggt gcatataaac
4441 acagatacac agtttggatc aacagttaat tattcttgta atgaagggtt tcgactcatt
4501 ggttccccat ctactacttg tctcgtctca ggcaataatg tcacatggga taagaaggca
4561 cctatttgtg agatcatatc ttgtgagcca cctccaacca tatccaatgg agacttctac
4621 agcaacaata gaacatcttt tcacaatgga acggtggtaa cttaccagtg ccacactgga
4681 ccagatggag aacagctgtt tgagcttgtg ggagaacggt caatatattg caccagcaaa
4741 gatgatcaag ttggtgtttg gagcagccct cccctcggt gtatttctac taataaatgc
4801 acagctccag aagttgaaaa tgcaattaga gtaccaggaa acaggagttt cttttccctc
4861 actgagatca tcagatttag atgtcagccc gggtttgtca tggtagggtc ccacactgtg
4921 cagtgccaga ccaatggcag atgggggccc aagctgccac actgctccag ggtgtgtcag
4981 ccgcctccag aaatcctgca tggtgagcat accctaagcc atcaggacaa cttttcacct
5041 gggcaggaag tgttctacag ctgtgagccc agctatgacc tcagaggggc tgcgtctctg
5101 cactgcacgc cccagggaga ctggagccct gaagccccta gatgtacagt gaaatcctgt
5161 gatgacttcc tgggccaact ccctcattaa cgtgtgctac ttccacttaa tctccagctt
5221 ggggcaaagg tgtcctttgt ttgcgatgaa gggttccgat taaaaggcag gtctgctagt
5281 cattgtgtct tggctggaat gaaagccctt tggaatagca gtgttccagt gtgtgaacaa
5341 atcttttgtc caaatcctcc agctatcctt aatgggagac acacaggaac tcccttttgga
5401 gatattccct atggaaaaga aatatcttac gcatgcgaca cccacccaga cagagggatg
5461 accttcaacc tcattgggga gagctccatc cgctgcacaa gtgaccctca agggaatggg
5521 gtttggagca gccctgcccc tcgctgtgaa ctttctgttc ctgctgcctg cccacatcca
5581 cccaagatcc aaaacgggca ttacattgga ggacacgtat ctctatatct tcctgggatg
5641 acaatcagct acacttgtga ccccggctac ctgttagtgg gaaagggctt catttctgtg
5701 acagaccagg gaatctggag ccaattggat cattattgca agaagtaaa ttgtagcttc
5761 ccactgttta tgaatggaat ctcgaaggag ttagaaatga aaaagtata tcactatgga
5821 gattatgtga ctttgaagtg tgaagatggg tatactctgg aaggcagtcc ctggagccag
5881 tgccaggcgg atgacagatg ggaccctcct ctggccaaat gtacctctcg tgcacatgat
5941 gctctcatag ttggcacttt atctggtacg atcttcttta ttttactcat cattttcctc
6001 tcttggataa ttctaaagca cagaaaaggc aataatgcac atgaaaaccc taaagaagtg
6061 gctatccatt tacattctca aggaggcagc agcgttcatc ccgaactct gcaaacaaat
6121 gaagaaaata gcagggtcct tccttgacaa agtactatac agctgaagaa catctcgaat
6181 acaatttggg tgggaagga gccaattgat ttcaacagaa tcagatctga gcttcataaa
6241 gtctttgaag tgacttcaca gagacgcaga catgtgcact gaagatgct gccccttccc
6301 tggtacctag caaagctcct gcctctttgt gtgcgtcact gtgaaacccc caccttctg
6361 cctcgtgcta aacgcacaca gtatctagtc aggggaaaag actgcatttta ggagatagaa
6421 aatagtttgg attacttaaa ggaataaggt gttgcctgga atttctggtt tgtaaggtgg
```

Fig. 3 (Cont.)

```
6481 tcactgttct tttttaaaat atttgtaata tggaatgggc tcagtaagaa gagcttggaa
6541 aatgcagaaa gttatgaaaa ataagtcact tataattatg ctacctactg ataaccactc
6601 ctaatatttt gattcatttt ctgcctatct tctttcacat atgtgttttt ttacatacgt
6661 acttttcccc ccttagtttg tttccttta ttttatagag cagaaccca gtcttttaaa
6721 cagtttagag tgaaatatat gctatatcag ttttttacttt ctctagggag aaaaattaat
6781 ttactagaaa ggcatgaaat gatcatggga agagtggtta agactactga agagaaatat
6841 ttggaaaata agatttcgat atcttctttt tttttgagat ggagtctggc tctgtctccc
6901 aggctggagt gcagtggcgt aatctcggct cactgcaacg tccgcctccc g
```

Fig. 3 (Cont.)

SEQ. ID NO:5

```
MEPPGRRECPFPSWRFPGLLLAAMVLLLYSFSDACEEPPTFEAMELIGKP    50
KPYYEIGERVDYKCKKGYFYIPPLATHTICDRNHTWLPVSDDACYRETCP    100
YIRDPLNGQAVPANGTYEFGYQMHFICNEGYYLIGEEILYCELKGSVAIW   150
SGKPPICEKVLCTPPPKIKNGKHTFSEVEVFEYLDAVTYSCDPAPGPDPF   200
SLIGESTIYCGDNSVWSRAAPECKVVKCRFPVVENGKQISGFGKKFYYKA   250
TVMFECDKGFYLDGSDTIVCDSNSTWDPPVPKCLKVSTSSTTKSPASSAS   300
GPRPTYKPPVSNYPGYPKPEEGILDSLDVWVIAVIVIAIVVGVAVICVVP   350
YRYLQRRKKKGKADGGAEYATYQTKSTTPAEQRG
```

Fig. 4A

SEQ. ID NO:6

```
    1 tctgctttcc tccggagaaa taacagcgtc ttccgcgccg cgcatggagc ctcccggccg
   61 ccgcgagtgt ccctttcctt cctggcgctt tcctgggttg cttctggcgg ccatggtgtt
  121 gctgctgtac tccttctccg atgcctgtga ggagccacca acatttgaag ctatggagct
  181 cattggtaaa ccaaaaccct actatgagat tggtgaacga gtagattata agtgtaaaaa
  241 aggatacttc tatataccct ctcttgccac ccatactatt tgtgatcgga atcatacatg
  301 gctacctgtc tcagatgacg cctgttatag agaaacatgt ccatatatac gggatccttt
  361 aaatggccaa gcagtccctg caaatgggac ttacgagttt ggttatcaga tgcactttat
  421 ttgtaatgag ggttattact taattggtga agaaattcta tattgtgaac ttaaaggatc
  481 agtagcaatt tggagcggta agccccaat atgtgaaaag gttttgtgta caccacctcc
  541 aaaaataaaa aatggaaaac acacctttag tgaagtagaa gtatttgagt atcttgatgc
  601 agtaacttat agttgtgatc ctgcacctgg accagatcca ttttcactta ttggagagag
  661 cacgatttat tgtggtgaca attcagtgtg gagtcgtgct gctccagagt gtaaagtggt
  721 caaatgtcga tttccagtag tcgaaaatgg aaaacagata tcaggatttg gaaaaaaatt
  781 ttactacaaa gcaacagtta tgtttgaatg cgataagggt ttttacctcg atggcagcga
  841 cacaattgtc tgtgacagta acagtacttg gatccccca gttccaaagt gtcttaaagt
  901 gtcgacttct tccactacaa aatctccagc gtccagtgcc tcaggtccta ggcctactta
  961 caagcctcca gtctcaaatt atccaggata tcctaaacct gaggaaggaa tacttgacag
 1021 tttggatgtt tgggtcattg ctgtgattgt tattgccata gttgttggag ttgcagtaat
 1081 ttgtgttgtc ccgtacagat atcttcaaag gaggaagaag aaagggaaag cagatggtgg
 1141 agctgaatat gccacttacc agactaaatc aaccactcca gcagagcaga gaggctgaat
 1201 agattccaca acctggttc ccagttcatc ttttgactct attaaaatct tcaatagttg
 1261 ttattctgta gtttcactct catgagtgca actgtggctt agctaatatt gcaatgtggc
 1321 ttgaatgtag gtagcatcct ttgatgcttc tttgaaactt gtatgaattt gggtatgaac
 1381 agattgcctg ctttccctta aataacactt agatttattg gaccagtcag cacagcatgc
 1441 ctgttgtat taaagcaggg atatgctgta ttttataaaa ttggcaaaat tagagaaata
 1501 tagttcacaa tgaaattata ttttctttgt
```

Fig. 4B

SEQ. ID NO:7
ATA TAC GAA TTC AGA TCT ATG ACC GTC GCG CGG CCG AGC GTG

SEQ. ID NO:8
ACA GTG CTC GAG CAT TCA GGT GGT GGG CCA CTC CA

SEQ. ID NO:9
ATA TAC CTC GAG TCC TAA CAA ATG CAC GCC TCC AAA TGT GG-3

SEQ. ID NO:10
ACA GTG ATG CAT TGG TTT GGG TTT TCA ACT TGG C

SEQ. ID NO:11
ATA TAC ATG CAT CTG ACT TTC CCA TTG GGA CAT CTT TAA AG

SEQ. ID NO:12
ACA GTG AGA TCT TTA GTG ATG GTG ATG GTG ATG AAT TCC ACA GCG AGG GGC AGG GCT

SEQ ID NO:13

SEQ. ID NO: 14

```
                                        ATGACCGTCGCGCGGCCGAGCGTGCCCGCGGCGCTGCCC
CTCCTCGGGGAGCTGCCCCGGCTGCTGCTGCTGGTGCTGTTGTGCCTGCCGGCCGTGTGGGGT
GACTGTGGCCTTCCCCCAGATGTACCTAATGCCCAGCCAGCTTTGGAAGGCCGTACAAGTTTT
CCCGAGGATACTGTAATAACGTACAAATGTGAAGAAAGCTTTGTGAAAATTCCTGGCGAGAAG
GACTCAGTGATCTGCCTTAAGGGCAGTCAATGGTCAGATATTGAAGAGTTCTGCAATCGTAGC
TGCGAGGTGCCAACAAGGCTAAATTCTGCATCCCTCAAACAGCCTTATATCACTCAGAATTAT
TTTCCAGTCGGTACTGTTGTGGAATATGAGTGCCGTCCAGGTTACAGAAGAGAACCTTCTCTA
TCACCAAAACTAACTTGCCTTCAGAATTTAAAATGGTCCACAGCAGTCGAATTTTGTAAAAAG
AAATCATGCCCTAATCCGGGAGAAATACGAAATGGTCAGATTGATGTACCAGGTGGCATATTA
TTTGGTGCAACCATCTCCTTCTCATGTAACACAGGGTACAAATTATTTGGCTCGACTTCTAGT
TTTTGTCTTATTTCAGGCAGCTCTGTCCAGTGGAGTGACCCGTTGCCAGAGTGCAGAGAAATT
TATTGTCCAGCACCACCACAAATTGACAATGGAATAATTCAAGGGGAACGTGACCATTATGGA
TATAGACAGTCTGTAACGTATGCATGTAATAAAGGATTCACCATGATTGGAGAGCACTCTATT
TATTGTACTGTGAATAATGATGAAGGAGAGTGGAGTGGCCCACCACCTGAATGC
TCGAGTCCTAACAAATGCACGCCTCCAAATGTGGAAAATGGAATATTGGTATCTGACAAC
AGAAGCTTATTTTCCTTAAATGAAGTTGTGGAGTTTAGGTGTCAGCCTGGCTTTGTCATG
AAAGGACCCCGCCGTGTGAAGTGCCAGGCCCTGAACAAATGGGAGCCGGAGCTACCAAGC
TGCTCCAGGGTATGTCAGCCACCTCCAGATGTCCTGCATGCTGAGCGTACCCAAAGGGAC
AAGGACAACTTTTCACCTGGGCAGGAAGTGTTCTACAGCTGTGAGCCCGGCTACGACCTC
AGAGGGGCTGCGTCTATGCGCTGCACACCCCAGGGAGACTGGAGCCCTGCAGCCCCACA
TGTGAAGTGAAATCCTGTGATGACTTCATGGGCCAACTTCTTAATGGCCGTGTGCTATTT
CCAGTAAATCTCCAGCTTGGAGCAAAAGTGGATTTTGTTTGTGATGAAGGATTTCAATTA
AAAGGCAGCTCTGCTAGTTACTGTGTCTTGGCTGGAATGGAAAGCCTTTGGAATAGCAGT
GTTCCAGTGTGTGAACAAATCTTTTGTCCAAGTCCTCCAGTTATTCCTAATGGGAGACAC
ACAGGAAAACCTCTGGAAGTCTTTCCCTTTGGAAAAGCAGTAAATTACACATGCGACCCC
CACCCAGACAGAGGGACGAGCTTCGACCTCATTGGAGAGAGCACCATCCGCTGCACAAGT
GACCCTCAAGGGAATGGGGTTTGGAGCAGCCCTGCCCCTCGCTGTGGAATTCTGGGTCAC
TGTCAAGCCCCAGATCATTTTCTGTTTGCCAAGTTGAAAACCCAAACCAATGCATCTGAC
TTTCCCATTGGGACATCTTTAAAGTACGAATGCCGTCCTGAGTACTACGGGAGGCCATTC
TCTATCACATGTCTAGATAACCTGGTCTGGTCAAGTCCCAAAGATGTCTGTAAACGTAAA
TCATGTAAAACTCCTCCAGATCCAGTGAATGGCATGGTGCATGTGATCACAGACATCCAG
GTTGGATCCAGAATCAACTATTCTTGTACTACAGGGCACCGACTCATTGGTCACTCATCT
GCTGAATGTATCCTCTCGGGCAATGCTGCCCATTGGAGCACGAAGCCGCCAATTTGTCAA
CGAATTCCTTGTGGGCTACCCCCCACCATCGCCAATGGAGATTTCATTAGCACCAACAGA
GAGAATTTTCACTATGGATCAGTGGTGACCTACCGCTGCAATCCTGGAAGCGGAGGGAGA
AAGGTGTTTGAGCTTGTGGGTGAGCCCTCCATATACTGCACCAGCAATGACGATCAAGTG
GGCATCTGGAGCGGCCCGGCCCCTCAGTGCATTATACCTAACAAATGCACGCCTCCAAAT
GTGGAAAATGGAATATTGGTATCTGACAACAGAAGCTTATTTTCCTTAAATGAAGTTGTG
GAGTTTAGGTGTCAGCCTGGCTTTGTCATGAAAGGACCCCGCCGTGTGAAGTGCCAGGCC
CTGAACAAATGGGAGCCGGAGCTACCAAGCTGCTCCAGGGTATGTCAGCCACCTCCAGAT
GTCCTGCATGCTGAGCGTACCCAAAGGGACAAGGACAACTTTTCACCCGGGCAGGAAGTG
TTCTACAGCTGTGAGCCCGGCTATGACCTCAGAGGGGCTGCGTCTATGCGCTGCACACCC
CAGGGAGACTGGAGCCCTGCAGCCCCACATGTGAAGTGAAATCCTGTGATGACTTCATG
GGCCAACTTCTTAATGGCCGTGTGCTATTTCCAGTAAATCTCCAGCTTGGAGCAAAAGTG
```

Fig. 8B

```
GATTTTGTTTGTGATGAAGGATTTCAATTAAAAGGCAGCTCTGCTAGTTATTGTGTCTTG
GCTGGAATGGAAAGCCTTTGGAATAGCAGTGTTCCAGTGTGTGAACAAATCTTTTGTCCA
AGTCCTCCAGTTATTCCTAATGGGAGACACACAGGAAAACCTCTGGAAGTCTTTCCCTTT
GGAAAAGCAGTAAATTACACATGCGACCCCCACCCAGACAGAGGGACGAGCTTCGACCTC
ATTGGAGAGAGCACCATCCGCTGCACAAGTGACCCTCAAGGGAATGGGGTTTGGAGCAGC
CCTGCCCCTCGCTGTGGAATTCATCACCATCACCATCACTAAAGATCT
```

Fig. 8B (Cont.)

SEQ ID NO:15

|   |   |   |   |   |   |   |   | M | T | V | A | R | P | S | V | P | A | A | L | P |
|---|---|---|---|---|---|---|---|---|---|---|---|---|---|---|---|---|---|---|---|---|
| L | L | G | E | L | P | R | L | L | L | V | L | L | C | L | P | A | V | W | G |   |
| D | C | G | L | P | P | D | V | P | N | A | Q | P | A | L | E | G | R | T | S | F |
| P | E | D | T | V | I | T | Y | K | C | E | E | S | F | V | K | I | P | G | E | K |
| D | S | V | I | C | L | K | G | S | Q | W | S | D | I | E | E | F | C | N | R | S |
| C | E | V | P | T | R | L | N | S | A | S | L | K | Q | P | Y | I | T | Q | N | Y |
| F | P | V | G | T | V | V | E | Y | E | C | R | P | G | Y | R | R | E | P | S | L |
| S | P | K | L | T | C | L | Q | N | L | K | W | S | T | A | V | E | F | C | K | K |
| K | S | C | P | N | P | G | E | I | R | N | G | Q | I | D | V | P | G | G | I | L |
| F | G | A | T | I | S | F | S | C | N | T | G | Y | K | L | F | G | S | T | S | S |
| F | C | L | I | S | G | S | S | V | Q | W | S | D | P | L | P | E | C | R | E | I |
| Y | C | P | A | P | P | Q | I | D | N | G | I | I | Q | G | E | R | D | H | Y | G |
| Y | R | Q | S | V | T | Y | A | C | N | K | G | F | T | M | I | G | E | H | S | I |
| Y | C | T | V | N | N | D | E | G | E | W | S | G | P | P | P | E | C |   |   |   |
| S | S | P | N | K | C | T | P | P | N | V | E | N | G | I | L | V | S | D | N |   |
| R | S | L | F | S | L | N | E | V | V | E | F | R | C | Q | P | G | F | V | M |   |
| K | G | P | R | R | V | K | C | Q | A | L | N | K | W | E | P | E | L | P | S |   |
| C | S | R | V | C | Q | P | P | P | D | V | L | H | A | E | R | T | Q | R | D |   |
| K | D | N | F | S | P | G | Q | E | V | F | Y | S | C | E | P | G | Y | D | L |   |
| R | G | A | A | S | M | R | C | T | P | Q | G | D | W | S | P | A | A | P | T |   |
| C | E | V | K | S | C | D | D | F | M | G | Q | L | L | N | G | R | V | L | F |   |
| P | V | N | L | Q | L | G | A | K | V | D | F | V | C | D | E | G | F | Q | L |   |
| K | G | S | S | A | S | Y | C | V | L | A | G | M | E | S | L | W | N | S | S |   |
| V | P | V | C | E | Q | I | F | C | P | S | P | V | I | P | N | G | R | H |   |   |
| T | G | K | P | L | E | V | F | P | F | G | K | A | V | N | Y | T | C | D | P |   |
| H | P | D | R | G | T | S | F | D | L | I | G | E | S | T | I | R | C | T | S |   |
| D | P | Q | G | N | G | V | W | S | S | P | A | P | R | C | G | I | L | G | H |   |
| C | Q | A | P | D | H | F | L | F | A | K | L | K | T | Q | T | N | A | S | D |   |
| F | P | I | G | T | S | L | K | Y | E | C | R | P | E | Y | Y | G | R | P | F |   |
| S | I | T | C | L | D | N | L | V | W | S | S | P | K | D | V | C | K | R | K |   |
| S | C | K | T | P | P | D | P | V | N | G | M | V | H | V | I | T | D | I | Q |   |
| V | G | S | R | I | N | Y | S | C | T | G | H | R | L | I | G | H | S | S |   |   |
| A | E | C | I | L | S | G | N | A | A | H | W | S | T | K | P | P | I | C | Q |   |
| R | I | P | C | G | L | P | P | T | I | A | N | G | D | F | I | S | T | N | R |   |
| E | N | F | H | Y | G | S | V | V | T | Y | R | C | N | P | G | S | G | G | R |   |
| K | V | F | E | L | V | G | E | P | S | I | Y | C | T | S | N | D | D | Q | V |   |
| G | I | W | S | G | P | A | P | Q | C | I | I | P | N | K | C | T | P | P | N |   |

Fig. 9A

| | | | | | | | | | | | | | | | |
|---|---|---|---|---|---|---|---|---|---|---|---|---|---|---|---|
| V | E | N | G | I | L | V | S | D | N | R | S | L | F | S | L | N | E | V | V |
| E | F | R | C | Q | P | G | F | V | M | K | G | P | R | R | V | K | C | Q | A |
| L | N | K | W | E | P | E | L | P | S | C | S | R | V | C | Q | P | P | P | D |
| V | L | H | A | E | R | T | Q | R | D | K | D | N | F | S | P | G | Q | E | V |
| F | Y | S | C | E | P | G | Y | D | L | R | G | A | A | S | M | R | C | T | P |
| Q | G | D | W | S | P | A | A | P | T | C | E | V | K | S | C | D | D | F | M |
| G | Q | L | L | N | G | R | V | L | F | P | V | N | L | Q | L | G | A | K | V |
| D | F | V | C | D | E | G | F | Q | L | K | G | S | S | A | S | Y | C | V | L |
| A | G | M | E | S | L | W | N | S | S | V | P | V | C | E | Q | I | F | C | P |
| S | P | P | V | I | P | N | G | R | H | T | G | K | P | L | E | V | F | P | F |
| G | K | A | V | N | Y | T | C | D | P | H | P | D | R | G | T | S | F | D | L |
| I | G | E | S | T | I | R | C | T | S | D | P | Q | G | N | G | V | W | S | S |
| P | A | P | R | C | G | I | L | G | H | C | Q | A | P | D | H | F | L | F | A |
| K | L | K | T | Q | T | N | A | S | D | F | P | I | G | T | S | L | K | Y | E |
| C | R | P | E | Y | Y | G | R | P | F | S | I | T | C | L | D | N | L | V | W |
| S | S | P | K | D | V | C | K | R | K | S | C | K | T | P | P | D | P | V | N |
| G | M | V | H | V | I | T | D | I | Q | V | | | | | | | | |

```
TCACCAAAACTAACTTGCCTTCAGAATTTAAAATGGTCCACAGCAGTCGAATTTTGTAAAAAG
AAATCATGCCCTAATCCGGGAGAAATACGAAATGGTCAGATTGATGTACCAGGTGGCATATTA
TTTGGTGCAACCATCTCCTTCTCATGTAACACAGGGTACAAATTATTTGGCTCGACTTCTAGT
TTTTGTCTTATTTCAGGCAGCTCTGTCCAGTGGAGTGACCCGTTGCCAGAGTGCAGAGAAATT
TATTGTCCAGCACCACCACAAATTGACAATGGAATAATTCAAGGGGAACGTGACCATTATGGA
TATAGACAGTCTGTAACGTATGCATGTAATAAAGGATTCACCATGATTGGAGAGCACTCTATT
TATTGTACTGTGAATAATGATGAAGGAGAGTGGAGTGGCCCACCACCTGAATGC
TCGAGTCCTAACAAATGCACGCCTCCAAATGTGGAAAATGGAATATTGGTATCTGACAAC
AGAAGCTTATTTTCCTTAAATGAAGTTGTGGAGTTTAGGTGTCAGCCTGGCTTTGTCATG
AAAGGACCCCGCCGTGTGAAGTGCCAGGCCCTGAACAAATGGGAGCCGGAGCTACCAAGC
TGCTCCAGGGTATGTCAGCCACCTCCAGATGTCCTGCATGCTGAGCGTACCCAAAGGGAC
AAGGACAACTTTTCACCTGGGCAGGAAGTGTTCTACAGCTGTGAGCCCGGCTACGACCTC
AGAGGGGCTGCGTCTATGCGCTGCACACCCCAGGGAGACTGGAGCCCTGCAGCCCCCACA
TGTGAAGTGAAATCCTGTGATGACTTCATGGGCCAACTTCTTAATGGCCGTGTGCTATTT
CCAGTAAATCTCCAGCTTGGAGCAAAAGTGGATTTTGTTTGTGATGAAGGATTTCAATTA
AAAGGCAGCTCTGCTAGTTACTGTGTCTTGGCTGGAATGGAAAGCCTTTGGAATAGCAGT
GTTCCAGTGTGTGAACAAATCTTTTGTCCAAGTCCTCCAGTTATTCCTAATGGGAGACAC
ACAGGAAAACCTCTGGAAGTCTTTCCCTTTGGAAAAGCAGTAAATTACACATGCGACCCC
CACCCAGACAGAGGGACGAGCTTCGACCTCATTGGAGAGAGCACCATCCGCTGCACAAGT
GACCCTCAAGGGAATGGGGTTTGGAGCAGCCCTGCCCCTCGCTGTGGAATTCTGGGTCAC
TGTCAAGCCCCAGATCATTTTCTGTTTGCCAAGTTGAAAACCCAAACCAATGCATCTGAC
TTTCCCATTGGGACATCTTTAAAGTACGAATGCCGTCCTGAGTACTACGGGAGGCCATTC
TCTATACATGTCTAGATAACCTGGTCTGGTCAAGTCCCAAAGATGTCTGTAAACGTAAA
TCATGTAAAACTCCTCCAGATCCAGTGAATGGCATGGTGCATGTGATCACAGACATCCAG
GTTGGATCCAGAATCAACTATTCTTGTACTACAGGGCACCGACTCATTGGTCACTCATCT
GCTGAATGTATCCTCTCGGGCAATGCTGCCCATTGGAGCACGAAGCCGCCAATTTGTCAA
CGAATTCCTTGTGGGCTACCCCCCACCATCGCCAATGGAGATTTCATTAGCACCAACAGA
GAGAATTTTCACTATGGATCAGTGGTGACCTACCGCTGCAATCCTGGAAGCGGAGGGAGA
AAGGTGTTTGAGCTTGTGGGTGAGCCCTCCATATACTGCACCAGCAATGACGATCAAGTG
GGCATCTGGAGCGGCCCGGCCCCTCAGTGCATTATACCTAACAAATGCACGCCTCCAAAT
GTGGAAAATGGAATATTGGTATCTGACAACAGAAGCTTATTTTCCTTAAATGAAGTTGTG
GAGTTTAGGTGTCAGCCTGGCTTTGTCATGAAAGGACCCCGCCGTGTGAAGTGCCAGGCC
CTGAACAAATGGGAGCCGGAGCTACCAAGCTGCTCCAGGGTATGTCAGCCACCTCCAGAT
GTCCTGCATGCTGAGCGTACCCAAAGGGACAAGGACAACTTTTCACCCGGGCAGGAAGTG
TTCTACAGCTGTGAGCCCGGCTATGACCTCAGAGGGGCTGCGTCTATGCGCTGCACACCC
CAGGGAGACTGGAGCCCTGCAGCCCCCACATGTGAAGTGAAATCCTGTGATGACTTCATG
GGCCAACTTCTTAATGGCCGTGTGCTATTTCCAGTAAATCTCCAGCTTGGAGCAAAAGTG
GATTTTGTTTGTGATGAAGGATTTCAATTAAAAGGCAGCTCTGCTAGTTATTGTGTCTTG
GCTGGAATGGAAAGCCTTTGGAATAGCAGTGTTCCAGTGTGTGAACAAATCTTTTGTCCA
AGTCCTCCAGTTATTCCTAATGGGAGACACACAGGAAAACCTCTGGAAGTCTTTCCCTTT
GGAAAAGCAGTAAATTACACATGCGACCCCCACCCAGACAGAGGGACGAGCTTCGACCTC
ATTGGAGAGAGCACCATCCGCTGCACAAGTGACCCTCAAGGGAATGGGGTTTGGAGCAGC
CCTGCCCCTCGCTGTGGAATTCTGGGTCACTGTCAAGCCCCAGATCATTTTCTGTTTGCC
AAGTTGAAAACCCAAACCAATGCATCTGACTTTCCCATTGGGACATCTTTAAAGTACGAA
TGCCGTCCTGAGTACTACGGGAGGCCATTCTCTATCACATGTCTAGATAACCTGGTCTGG
TCAAGTCCCAAAGATGTCTGTAAACGTAAATCATGTAAAACTCCTCCAGATCCAGTGAAT
GGCATGGTGCATGTGATCACAGACATCCAGGTT
GGATCCAGAATCAACTATTCTTGTACTACAGGGCACCGACTCATTGGTCACTCATCT
GCTGAATGTATCCTCTCGGGCAATGCTGCCCATTGGAGCACGAAGCCGCCAATTTGTCAA
CGAATTCCTTGTGGGCTACCCCCCACCATCGCCAATGGAGATTTCATTAGCACCAACAGA
GAGAATTTTCACTATGGATCAGTGGTGACCTACCGCTGCAATCCTGGAAGCGGAGGGAGA
```

Fig. 9B (Cont.)

```
AAGGTGTTTGAGCTTGTGGGTGAGCCCTCCATATACTGCACCAGCAATGACGATCAAGTG
GGCATCTGGAGCGGCCCGGCCCCTCAGTGCATTATACCTAACAAATGCACGCCTCCAAAT
GTGGAAAATGGAATATTGGTATCTGACAACAGAAGCTTATTTTCCTTAAATGAAGTTGTG
GAGTTTAGGTGTCAGCCTGGCTTTGTCATGAAAGGACCCCGCCGTGTGAAGTGCCAGGCC
CTGAACAAATGGGAGCCGGAGCTACCAAGCTGCTCCAGGGTATGTCAGCCACCTCCAGAT
GTCCTGCATGCTGAGCGTACCCAAAGGGACAAGGACAACTTTTCACCCGGGCAGGAAGTG
TTCTACAGCTGTGAGCCCGGCTATGACCTCAGAGGGGCTGCGTCTATGCGCTGCACACCC
CAGGGAGACTGGAGCCCTGCAGCCCCACATGTGAAGTGAAATCCTGTGATGACTTCATG
GGCCAACTTCTTAATGGCCGTGTGCTATTTCCAGTAAATCTCCAGCTTGGAGCAAAAGTG
GATTTTGTTTGTGATGAAGGATTTCAATTAAAAGGCAGCTCTGCTAGTTATTGTGTCTTG
GCTGGAATGGAAAGCCTTTGGAATAGCAGTGTTCCAGTGTGTGAACAAATCTTTTGTCCA
AGTCCTCCAGTTATTCCTAATGGGAGACACACAGGAAAACCTCTGGAAGTCTTTCCCTTT
GGAAAAGCAGTAAATTACACATGCGACCCCCACCCAGACAGAGGGACGAGCTTCGACCTC
ATTGGAGAGAGCACCATCCGCTGCACAAGTGACCCTCAAGGGAATGGGGTTTGGAGCAGC
CCTGCCCCTCGCTGTGGAATTCATCACCATCACCATCACTAAAGATCT
```

Fig. 9B (cont.)

SEQ. ID NO:17
ATA TAC GAA TTC TGG TTG AGT CCA AAT ATG GTC CC

Fig. 10A

SEQ. ID NO:18
ACA GTG AGA TCT TTA TCA TTT ACC CGG AGA CAG GGA G

Fig. 10B

SEQ. ID NO:19

SEQ. ID NO:20

```
                        ATGACCGTCGCGCGGCCGAGCGTGCCCGCGGCGCTGCCC
CTCCTCGGGGAGCTGCCCCGGCTGCTGCTGCTGGTGCTGTTGTGCCTGCCGGCCGTGTGGGGT
GACTGTGGCCTTCCCCCAGATGTACCTAATGCCCAGCCAGCTTTGGAAGGCCGTACAAGTTTT
CCCGAGGATACTGTAATAACGTACAAATGTGAAGAAAGCTTTGTGAAAATTCCTGGCGAGAAG
GACTCAGTGATCTGCCTTAAGGGCAGTCAATGGTCAGATATTGAAGAGTTCTGCAATCGTAGC
TGCGAGGTGCCAACAAGGCTAAATTCTGCATCCCTCAAACAGCCTTATATCACTCAGAATTAT
TTTCCAGTCGGTACTGTTGTGGAATATGAGTGCCGTCCAGGTTACAGAAGAGAACCTTCTCTA
TCACCAAAACTAACTTGCCTTCAGAATTTAAAATGGTCCACAGCAGTCGAATTTTGTAAAAAG
AAATCATGCCCTAATCCGGGAGAAATACGAAATGGTCAGATTGATGTACCAGGTGGCATATTA
TTTGGTGCAACCATCTCCTTCTCATGTAACACAGGGTACAAATTATTTGGCTCGACTTCTAGT
TTTTGTCTTATTTCAGGCAGCTCTGTCCAGTGGAGTGACCCGTTGCCAGAGTGCAGAGAAATT
TATTGTCCAGCACCACCACAAATTGACAATGGAATAATTCAAGGGGAACGTGACCATTATGGA
TATAGACAGTCTGTAACGTATGCATGTAATAAAGGATTCACCATGATTGGAGAGCACTCTATT
TATTGTACTGTGAATAATGATGAAGGAGAGTGGAGTGGCCCACCACCTGAATGC
TCGAGTCCTAACAAATGCACGCCTCCAAATGTGGAAATGGAATATTGGTATCTGACAAC
AGAAGCTTATTTTCCTTAAATGAAGTTGTGGAGTTTAGGTGTCAGCCTGGCTTTGTCATG
AAAGGACCCCGCCGTGTGAAGTGCCAGGCCCTGAACAAATGGGAGCCGGAGCTACCAAGC
TGCTCCAGGGTATGTCAGCCACCTCCAGATGTCCTGCATGCTGAGCGTACCCAAAGGGAC
AAGGACAACTTTTCACCTGGGCAGGAAGTGTTCTACAGCTGTGAGCCCGGCTACGACCTC
```

Fig. 11B

AGAGGGGCTGCGTCTATGCGCTGCACACCCCAGGGAGACTGGAGCCCTGCAGCCCCCACA
TGTGAAGTGAAATCCTGTGATGACTTCATGGGCCAACTTCTTAATGGCCGTGTGCTATTT
CCAGTAAATCTCCAGCTTGGAGCAAAAGTGGATTTTGTTTGTGATGAAGGATTTCAATTA
AAAGGCAGCTCTGCTAGTTACTGTGTCTTGGCTGGAATGGAAAGCCTTTGGAATAGCAGT
GTTCCAGTGTGTGAACAAATCTTTTGTCCAAGTCCTCCAGTTATTCCTAATGGGAGACAC
ACAGGAAAACCTCTGGAAGTCTTTCCCTTTGGAAAAGCAGTAAATTACACATGCGACCCC
CACCCAGACAGAGGGACGAGCTTCGACCTCATTGGAGAGAGCACCATCCGCTGCACAAGT
GACCCTCAAGGGAATGGGGTTTGGAGCAGCCCTGCCCCTCGCTGTG<u>GAATTCTG</u>
GTTGAGTCCAAATATGGTCCCCCATGCCCATCATGCCCAGCACCTGAGTTCCTG
GGGGGACCATCAGTCTTCCTGTTCCCCCCAAAACCAAGGACACTCTCATGATCTCCCGG
ACCCCTGAGGTCACGTGCGTGGTGGTGGACGTGAGCCAGGAAGACCCCGAGGTCCAGTTC
AACTGGTACGTGGATGGCGTGGAGGTGCATAATGCCAAGACAAAGCCGCGGGAGGAGCAG
TTCAACAGCACGTACCGTGTGGTCAGCGTCCTCACCGTCCTGCACCAGGACTGGCTGAAC
GGCAAGGAGTACAAGTGCAAGGTCTCCAACAAAGGCCTCCCGTCCTCCATCGAGAAAACC
ATCTCCAAAGCCAAAGGGCAGCCCCGAGAGCCACAGGTGTACACCCTGCCCCCATCCCAG
GAGGAGATGACCAAGAACCAGGTCAGCCTGACCTGCCTGGTCAAAGGCTTCTACCCCAGC
GACATCGCCGTGGAGTGGGAGAGCAATGGGCAGCCGGAGGACAACTACAAGACCACGCCT
CCCGTGCTGGACTCCGACGGCTCCTTCTTCCTCTACAGCAGGCTAACCGTGGACAAGAGC
AGGTGGCAGGAGGGGAATGTCTTCTCATGCTCCGTGATGCATGAGGCTCTGCACAACCAC
TACACACAGAAGAGCCTCTCCCTGTCTCCGGGTAAATGATAA<u>AGATCT</u>

Fig. 11B (Cont.)

SEQ. ID NO:21
ATA TAC GAA TTC TGG GTC ACT GTG AGG AGC CAC CAA CAT TTG AAG C

Fig. 12A

SEQ. ID NO:22
ACA GTG AGA TCT TTA GTG ATG GTG ATG GTG ATG CGA CAC TTT AAG ACA CTT
TGG AAC

Fig. 12B

SEQ. ID NO:23
```
M T V A R P S V P A A L P
L L G E L P R L L L V L L C L P A V W G
D C G L P P D V P N A Q P A L E G R T S F
P E D T V I T Y K C E E S F V K I P G E K
D S V I C L K G S Q W S D I E E F C N R S
C E V P T R L N S A S L K Q P Y I T Q N Y
F P V G T V V E Y E C R P G Y R R E P S L
S P K L T C L Q N L K W S T A V E F C K K
K S C P N P G E I R N G Q I D V P G G I L
F G A T I S F S C N 'T G Y K L F G S T S S
F C L I S G S S V Q W S D P L P E C R E I
```

SEQ. ID NO:24
ATGACCGTCGCGCGGCCGAGCGTGCCCGCGGCGCTGCCC
CTCCTCGGGGAGCTGCCCCGGCTGCTGCTGCTGGTGCTGTTGTGCCTGCCGGCCGTGTGGGGT
GACTGTGGCCTTCCCCCAGATGTACCTAATGCCCAGCCAGCTTTGGAAGGCCGTACAAGTTTT
CCCGAGGATACTGTAATAACGTACAAATGTGAAGAAAGCTTTGTGAAAATTCCTGGCGAGAAG
GACTCAGTGATCTGCCTTAAGGGCAGTCAATGGTCAGATATTGAAGAGTTCTGCAATCGTAGC
TGCGAGGTGCCAACAAGGCTAAATTCTGCATCCCTCAAACAGCCTTATATCACTCAGAATTAT
TTTCCAGTCGGTACTGTTGTGGAATATAGTGCCGTCCAGGTTACAGAAGAGAACCTTCTCTA
TCACCAAAACTAACTTGCCTTCAGAATTTAAAATGGTCCACAGCAGTCGAATTTTGTAAAAAG
AAATCATGCCCTAATCCGGGAGAAATACGAAATGGTCAGATTGATGTACCAGGTGGCATATTA
TTTGGTGCAACCATCTCCTTCTCATGTAACACAGGGTACAAATTATTTGGCTCGACTTCTAGT
TTTTGTCTTATTTCAGGCAGCTCTGTCCAGTGGAGTGACCCGTTGCCAGAGTGCAGAGAAATT
TATTGTCCAGCACCACCACAAATTGACAATGGAATAATTCAAGGGGAACGTGACCATTATGGA
TATAGACAGTCTGTAACGTATGCATGTAATAAAGGATTCACCATGATTGGAGAGCACTCTATT
TATTGTACTGTGAATAATGATGAAGGAGAGTGGAGTGGCCCACCACCTGAATGC
TCGAGTCCTAACAAATGCACGCCTCCAAATGTGGAAAATGGAATATTGGTATCTGACAAC
AGAAGCTTATTTTCCTTAAATGAAGTTGTGGAGTTTAGGTGTCAGCCTGGCTTTGTCATG

Fig. 13B

```
AAAGGACCCCGCCGTGTGAAGTGCCAGGCCCTGAACAAATGGGAGCCGGAGCTACCAAGC
TGCTCCAGGGTATGTCAGCCACCTCCAGATGTCCTGCATGCTGAGCGTACCCAAAGGGAC
AAGGACAACTTTTCACCTGGGCAGGAAGTGTTCTACAGCTGTGAGCCCGGCTACGACCTC
AGAGGGGCTGCGTCTATGCGCTGCACACCCCAGGGAGACTGGAGCCCTGCAGCCCCCACA
TGTGAAGTGAAATCCTGTGATGACTTCATGGGCCAACTTCTTAATGGCCGTGTGCTATTT
CCAGTAAATCTCCAGCTTGGAGCAAAAGTGGATTTTGTTTGTGATGAAGGATTTCAATTA
AAAGGCAGCTCTGCTAGTTACTGTGTCTTGGCTGGAATGGAAAGCCTTTGGAATAGCAGT
GTTCCAGTGTGTGAACAAATCTTTTGTCCAAGTCCTCCAGTTATTCCTAATGGGAGACAC
ACAGGAAAACCTCTGGAAGTCTTTCCCTTTGGAAAAGCAGTAAATTACACATGCGACCCC
CACCCAGACAGAGGGACGAGCTTCGACCTCATTGGAGAGAGCACCATCCGCTGCACAAGT
GACCCTCAAGGGAATGGGGTTTGGAGCAGCCCTGCCCCTCGCTGTGGAATTCTGGGTCAC
TGTGAGGAGCCACCAACATTTGAAGCTATGGAGCTCATTGGTAAACCAAAACCCTACTAT
GAGATTGGTGAACGAGTAGATTATAAGTGTAAAAAGGATACTTCTATATACCTCCTCTT
GCCACCCATACTATTTGTGATCGGAATCATACATGGCTACCTGTCTCAGATGACGCCTGT
TATAGAGAAACATGTCCATATATACGGGATCCTTTAAATGGCCAAGCAGTCCCTGCAAAT
GGGACTTACGAGTTTGGTTATCAGATGCACTTTATTTGTAATGAGGGTTATTACTTAATT
GGTGAAGAAATTCTATATTGTGAACTTAAAGGATCAGTAGCAATTTGGAGCGGTAAGCCC
CCAATATGTGAAAAGGTTTTGTGTACACCACCTCCAAAAATAAAAAATGGAAAACACACC
TTTAGTGAAGTAGAAGTATTTGAGTATCTTGATGCAGTAACTTATAGTTGTGATCCTGCA
CCTGGACCAGATCCATTTTCACTTATTGGAGAGAGCACGATTTATTGTGGTGACAATTCA
GTGTGGAGTCGTGCTGCTCCAGAGTGTAAAGTGGTCAAATGTCGATTTCCAGTAGTCGAA
AATGGAAAACAGATATCAGGATTTGGAAAAAAATTTTACTACAAAGCAACAGTTATGTTT
GAATGCGATAAGGGTTTTTACCTCGATGGCAGCGACACAATTGTCTGTGACAGTAACAGT
ACTTGGGATCCCCCAGTTCCAAAGTGTCTTAAA//GTGTCG//CATCACCATCACCATCAC
TAAAGATCT
```

Fig. 13B (Cont.)

HYBRID AND CHIMERIC POLYPEPTIDES THAT REGULATE ACTIVATION OF COMPLEMENT

This application is a Continuation of U.S. Ser. No. 10/597,373, filed Aug. 3, 2007, now U.S. Pat. No. 8,124,097 which corres. to PCT/IB2005/050257, filed Jan. 21, 2005, and claims priority from U.S. Provisional Application No. 60/537,860, filed Jan. 21, 2004, the subject matter of which are incorporated herein by reference in their entirety.

STATEMENT REGARDING FEDERALLY SPONSORED RESEARCH OR DEVELOPMENT

The present invention was made, at least in part, with support from NIH grant #AI23598 The U.S. government may have certain rights in this invention.

BACKGROUND OF THE INVENTION

The complement system comprises a number of serum proteins that function in the body's immune response to infection and tissue injury. Activation of complement can occur via three pathways, the classical pathway involving the binding of complement component C1q to antigen-antibody complexes, the lectin pathway involving binding of mannose binding lectins to antigens, and the alternative pathway involving binding of complement component C3b to an activator surface such as cell wall polysaccharides of yeast and bacterial microorganisms. Activation of complement results in the formation of anaphylatoxins (C3a and C5a), membrane attack complexes (C5b-9), and opsonins (C3b and C4b) that amplify inflammation and destroy foreign and necrotic cells.

Complement activation is regulated by a number of plasma and cell associated proteins. Such proteins inactivate specific steps of the classical, lectin, and/or alternative pathway by regulating the activity of C3/C5 convertases or serving as a cofactor for the factor I cleavage of C3b and/or C4b. These proteins are either soluble plasma proteins or membrane proteins (integral or lipid-anchored) expressed on a variety of cell types. These proteins possess many structural similarities.

Decay Accelerating Factor (DAF)

Decay accelerating factor (DAF, CD55) is a membrane-associated regulatory protein that protects self cells from activation of autologous complement on their surfaces. DAF acts by rapidly dissociating C3 and C5 convertases, the central enzymes of the cascade. DAF possesses the most potent decay accelerating activity of the proteins associated with complement regulation, and acts on both the classical pathway (C4b2a and C4b2a3b) and alternative pathway (C3bBb and C3BbC3b) enzymes. DAF, however, does not have cofactor function.

Structural analyses of DAF have shown that, starting from its N-terminus, it is composed of four ~60 amino acid-long units followed by a heavily O-glycosylated serine (S) and threonine (T) rich stretch, which is, in turn, linked to a post-translationally-added glycoinositolphospholipid (GPT) anchor. The amino acid sequence of DAF is shown in FIG. 1 A (SEQ. ID NO: 1). The four 60 amino acid long repeating units are termed complement control protein repeats (CCPs) or short consensus repeats (SCRs). CCPI includes amino acids 35-95 of SEQ. ID NO: 1. CCP2 includes amino acids 97-159; CCP3 includes amino acids 162-221 and CCP includes amino acids 224-284 of SEQ. ID NO: 1. They provide for all of DAF's regulatory activity. The heavily O-glycosylated region serves as a cushion which positions the CCPs at an appropriate distance above the surface membrane. The GPI anchor allows DAF to move freely in the plane of the plasma membrane enabling it to inactivate convertase complexes wherever they assemble.

The critical role that DAF plays in inhibiting complement activation is evident both from natural disease and studies in animal models employing Daf knockout mice. In the human disease paroxysmal nocturnal hemoglobinuria (PNH), mutation in the GPI anchor pathway leading to the absence of DAF renders affected blood cells susceptible to heightened C3b uptake and intravascular hemolysis. In the animal disease models employing the Daf knockout, the absence of DAF renders the mice markedly more susceptible to tissue damage in 1) nephrotoxic serum (NTS) induced nephritis, a model of human membranous glomerulonephritis, 2) dextran sodium sulfate (DSS) induced colitis, a model of inflammatory bowel disease, and 3) anti-acetylcholine receptor (anti-AChR) induced myasthenia gravis, a close model of the human autoimmune disorder.

The nucleotide sequence of a cDNA encoding DAF is shown in FIG. 1B (SEQ. ID NO: 2).

Complement Receptor 1 (CR1)

Complement receptor 1 (CR1 or the C3b receptor, CD35) is another potent regulator of complement activation. Unlike DAF which functions intrinsically to protect the cells that express it, CR1 functions extrinsically on targets of complement attack, e.g. pathogens. CR1 is a larger molecule in that, rather than 4 CCPs, it is comprised of 30 CCPs arranged in 4 groups of 7 CCPs termed long homologous repeats (LHRs). The CCPs and LHRs of CR1 are provided in Table I below. The amino acid residue numbers refer to the amino acid sequence provided in FIG. 2 (SEQ. ID NO: 3). Functional analyses have shown that CR1 possesses both decay accelerating activity and cofactor activity for cleavage of C4b and C3b by the serum enzyme, factor I. Early studies showed that among complement regulators, it is the most potent in this latter activity and that it is the only regulator that promotes both initial cleavage of C3b to iC3b and subsequent cleavage of the iC3b intermediate to C3dg, the surface-bound C3b end product.

Structure-function studies of CR1 have shown that its regulatory activity resides primarily in its three N-terminal LHRs, i.e., LHRs A, B, and C. Functional activity within each 7 CCP LHR is contained essentially in each case in the first 3 CCPs. Recent studies have shown that CR1's potent cofactor activity resides in LHRs B and C, while its decay accelerating activity resides in LHR A.

The nucleotide sequence of a cDNA encoding CR1 is shown in FIG. 3 (SEQ. ID NO: 4).

TABLE 1

| Amino Acid No. | Domain |
| --- | --- |
| 1 or 6-46 | Leader peptide |
| 47-106 | CCP1, begin LHR-A |
| 107-168 | CCP2 |
| 169-238 | CCP3 |
| 239-300 | CCP4 |
| 301-360 | CCP4 |
| 361-423 | CCP5 |
| 424-496 | CCP7, end LHR-A |
| 497-556 | CCP8, begin LHR-B |
| 557-618 | CCP9 |
| 619-688 | CCP10 |
| 689-750 | CCP11 |
| 751-810 | CCP12 |
| 811-873 | CCP12 |
| 874-946 | CCP14, end LHR-B |

TABLE 1-continued

| Amino Acid No. | Domain |
| --- | --- |
| 947-1006 | CCP15, begin LHR-C |
| 1007-1068 | CCP15 |
| 1069-1138 | CCP16 |
| 1139-1200 | CCP17 |
| 1201-1260 | CCP18 |
| 1261-1323 | CCP20 |
| 1324-1399 | CCP21, end LHR-C |
| 1400-1459 | CCP22, begin LHR-D |
| 1460-1521 | CCP23 |
| 1522-1591 | CCP24 |
| 1592-1653 | CCP25 |
| 1654-1713 | CCP26 |
| 1714-1776 | CCP27 |
| 1777-1851 | CCP28, and LHR-D |
| 1852-1911 | CCP29 |
| 1912-1972 | CCP30 |

Membrane Cofactor Protein (MCP)

MCP (also known as 'CD46') is present on the cell surface of a number of cell types including peripheral blood cells (excluding erythrocytes), cells of epithelial, endothelial and fibroblast lineages, trophoblasts and sperm. MCP has four CCPs and a serine/threonine enriched region in which heavy O-linked glycosylation occurs. MCP also has a transmembrane and cytoplasmic domain. The structure of MCP is provided in Table 2 below with reference to the amino acid sequence of MCP provided in FIG. 4A (SEQ. ID NO: 5). MCP works by binding to the C3b and C4b present on the cell surface thereby targeting C3b and C4b for degradation by factor I, a plasma protease, and thereby destroying any subsequent C3 or C4 convertase activity. Thus, MCP is said to have "cofactor activity". Because MCP is localized on the cell surface, it protects only the cells on which it is present and is therefore said to act in an intrinsic manner. The sequence of a cDNA encoding human MCP has been reported by Lublin et al, J. Exp. Med., (1988) 168:181-194. The nucleotide sequence of a cDNA encoding MCP is shown in FIG. 4B (SEQ ID NO: 6).

TABLE 2

| Amino Acid | Domain |
| --- | --- |
| 1-34 | Leader peptide |
| 35-95 | CCP |
| 96-158 | CCP |
| 159-224 | CCP |
| 225-285 | CCP |
| 286-314 | STP<br>B-domain: VSTSSTTKPASSAS<br>C-domain: GPRPTYKPPVSNP |
| 315-327 | Undefined segment |
| 328-351 | Transmembrane domain |
| 352-361 | Intracytoplasmic anchor |
| 362-377 | Cytoplasmic tail one:<br>TYLTDETHREVKFTSL |
| 362-384 | Cytoplasmic tail two:<br>KADGGAEYATYQTKSTTPAEQRC |

Effects of Excessive Activation of Complement

Excessive activation of complement causes damage to normal host tissues in a number of conditions. Some diseases in which complement is known to be activated include systemic lupus erythematosus, acute myocardial infarction, burn, sepsis, stroke and the adult respiratory distress syndrome. Accordingly, it is desirable to have soluble agents that can block complement activation. Such agents would be useful for treating the above-mentioned human diseases and a wide range of other diseases (See Table 3 below). The construction of hybrid complement regulatory proteins has been attempted previously, but with mixed results. For example, a hybrid containing CCPs 1-4 of MCP and CCPs 1-4 of DAF was constructed by Iwata, et al (J. Immunol. 1194, 152:3436). While this hybrid had greater activity in the alternative pathway than either MCP or DAF, it had less activity than DAF alone or DAF plus MCP in the classical pathway. Additionally, in tests of reciprocal chimeric complement inhibitors, one chimeric protein retained the activity of is CD59 and DAF components, while its reciprocal retained only the activity of its DAF component (Fodor, et al, J. Immunol., 1995, 155: 4135). Therefore, there is a need for a reliable method for constructing hybrid and chimeric complement regulatory proteins. There is also a need for a hybrid complement regulating protein that possesses the decay accelerating activity of DAF and the co factor activity of CR1.

TABLE 3

Potential Clinical Targets of Protein of the Invention

| Alternative Pathway | Classical Pathway |
| --- | --- |
| Reperfusion injury | Autoimmune diseases |
| Cerebral infarction (stroke) | Systemic lupus erythematosus |
| Acute myocardial infarction | Rheumatoid arthritis |
| Hypovolemic shock | Glomerulonephritis |
| Multiple organ failure | Hemolytic anemia |
| Crush injury | Myasthenia gravis |
| Intestinal ischemia | Multiple sclerosis |
| Inflammatory disorders | Vasculitis |
| Adult respiratory distress syndrome | Inflammatory bowel diseases |
| Thermal injury (burn & frostbite) | Bullous diseases |
| Post-pump syndrome (cardiopulmonary bypass & hemodialysis) | Urticaria |
| | Paroxysmal nocturnal |
| Crohn's disease | Hemoglobinuria |
| Sickle cell anemia | Cryoglobulinemia |
| Pancreatitis | Inflammatory disorders |
| Adverse drug reactions | Septic shock & endotoxemia |
| Radiographic contrast media allergy | Transplant rejection |
| Drug allergy | Hyperacute allograft |
| IL-2 induced vascular leakage syndrome | |
| Transplant rejection | |
| Hyperacute xenograft | |

BRIEF DESCRIPTION OF THE DRAWINGS

FIG. 1A is a listing of the amino acid sequence of human Decay Accelerating Factor (DAF), SEQ. ID NO: 1;

FIG. 1B is a listing of a DNA sequence encoding DAF, SEQ. ID NO: 2;

FIG. 2 is a listing of the amino acid sequence of human Complement Receptor 1 (CR1), SEQ. ID NO: 3;

FIG. 3 is a listing of a DNA sequence encoding CR1, SEQ. ID NO: 4;

FIG. 4A is listing of the amino acid sequence of human Membrane Cofactor Protein (MCP), SEQ. ID NO: 5;

FIG. 4B is a listing of a DNA sequence encoding MCP, SEQ. ID NO: 6;

FIG. 8A is a listing of the amino acid sequence of the protein DAF-CR1B, SEQ. ID NO: 13;

FIG. 8B is a listing of a DNA sequence encoding DAF-CR1B, SEQ. ID NO: 14;

FIG. 9A is a listing of the amino acid sequence of protein DAF-CR1BB, SEQ. ID NO: 15;

FIG. 9B is a listing of a DNA sequence encoding DAF-CR1BB, SEQ. ID NO: 15;

FIGS. 10A and 10B are listings of the PCR primers IgG45 and IgG43, SEQ. ID NO's: 17 and 18, respectively;

FIG. 11A is a listing of amino acid sequence of protein DAF-IgG4, SEQ. ID NO: 19;

FIG. 11B is a listing of a DNA sequence encoding DAF-IgG4, SEQ. ID NO: 20;

FIGS. 12A and 12B are listings of the PCR primers MCP5 and MCP3, SEQ. ID NO's: 21 and 22, respectively;

FIG. 13A is a listing of the amino acid sequence of protein DAF-MCP, SEQ ID NO: 23;

FIG. 13B is a listing of a DNA sequence encoding DAF-MCP, SEQ. ID NO: 24;

SUMMARY OF THE INVENTION

Figures 5, 6A, 6B, 7A, 7B, 7C, 7D:
FIG. 5 is a representation of a lipid tail structure.
FIGS. 6A and 6B are listings of PCR primers DSIGEB and DAF3P, SEQ. ID NO's: 7 and 8, respectively.
FIGS. 7A-7D are listings of PCR primers CR1094X, CR1099N, CR1350N, and CR1B3P, SEQ. ID NO's: 9-12, respectively.

It is therefore an aspect of the present invention to provide hybrid and chimeric complement regulating proteins. The present invention relates to a family of hybrid and chimeric polypeptides for regulating, more particularly for inhibiting, excessive complement activation.

A hybrid complement-regulating protein of the present invention comprises a first functional unit of a first complement regulatory protein having complement regulating properties, a first spacer sequence of at least about 200 amino acids encoding a polypeptide that does not exhibit complement regulating properties and at least a second functional unit attached to the spacer sequence. The second functional unit may be a polypeptide providing a functional unit of a second complement regulatory protein, a polypeptide derived from an immunoglobulin, or a polypeptide that enhances binding of the protein to an animal cell. The hybrid protein may also contain a second spacer sequence and a third functional unit of a complement regulatory protein, a polypeptide derived from an immunoglobulin, and a polypeptide that enhances binding of the protein to an animal cell. The optional third functional unit may be the same or different from the first or second functional units. It has been advantageously discovered that the construction of hybrid complement regulating proteins requires more than simply the presence of the protein domains providing decay accelerating activity (as from DAF) and co-factor activity (as from CR1 or MCP). Proper spacing of such domains is also required for activity of both domains in a hybrid protein. In one embodiment, the hybrid protein (referred to hereafter as a "DAF hybrid") comprises CCPs 2 and 3, of DAF as one functional unit. Preferably, such a functional unit also comprises CCP4 and more preferably, comprises CCPs 1-4 of DAF. The DAF hybrid protein can also include one or more functional units that have been derived from CR1, e.g., one or more functional units comprising CCPs 8-10 of CR1 or functional units comprising CCPs 15-17 of CR1, or combinations thereof. The DAF hybrid polypeptide can also include one or more functional units that have been derived from MCP, e.g. CCPs 2, 3, and 4. Preferably, the MCP functional unit also comprises CCP1 of MCP. The DAF hybrid protein can also comprise functional units that have been derived from other complement activation regulatory proteins. Examples of such proteins include, but are not limited to, the factor H protein and C4BP. In certain embodiments, the hybrid polypeptide comprises functional units that have been derived from three or more complement activation regulatory proteins, in which each functional unit is separated from the preceding functional unit and following functional unit in the hybrid polypeptide by a spacer.

The present spacer is a polypeptide that is greater than 200 amino acids in length, preferably greater than 250 amino acids in length. Where more than one spacer is used, the amino acid sequences of the spacers that are employed may be the same or different. The spacer may be a synthetic polypeptide fragment. Alternatively, the spacer is derived from a complement activation regulatory protein. In one embodiment, the spacer comprises all or substantially all of CCPs 4-7 of CR1, i, e, amino acid 239 through amino acid 496 of the CR1 sequence shown in FIG. 2 (SEQ. ID NO: 2). These CCPs have no known activity directly associated with them. While not wishing to condition patentability on any particular theory, it is believed that these CCPs function in the native CR1 protein to properly space those CCPs that do have directly-associated activity from each other. In another embodiment, the spacer comprises all or substantially all of CCPs 11-14 of the CR1 protein. In most embodiments, the spacer does not exhibit complement-regulating activity. The hybrid proteins of the present invention are based, at least in part, on Applicants discovery that on an equal molar basis, DAF is at least 4 to 5 times more efficient than LHR A of CR1 in inhibiting the classical pathway.

The chimeric polypeptides of the present invention comprise at least one functional unit that has been derived from a complement activation regulatory protein (referred to hereinafter as the "first functional unit"), a functional unit that has been derived from a protein that is not a complement activation regulatory protein (referred to hereinafter as the "second functional unit"), and a spacer for separating and appropriately spacing the first functional unit from the second functional unit. The spacer is as described above. The second functional unit can be derived from immunoglobulin (IgG) and may serve to reduce degradation of the chimeric polypeptide following injection into an animal. Alternatively, the second functional unit can be a targeting moiety that enhances binding of the chimeric polypeptide by certain animal tissues. An example of one such targeting moiety is a lipid tail, as shown in attached FIG. 5. Such a molecule is expected to target the chimeric polypeptide to the membrane bilayer interior, more particularly to areas of translocated acidic phospholipid. (See, Smith, R A (2002) Biochem Soc Trans 30 (Pt6):1037-41.) The second function unit can also be a targeting moiety that enhances binding of the chimeric polypeptide to an implant, or to an extracorporeal surface, e.g. a hemodialysis membrane. In certain embodiments, the chimeric protein may comprise multiple functional units that have been derived from one or more complement activation regulatory proteins, each of which are separated from one another by a spacer. Thus, the chimeric polypeptide of the present invention can be a hybrid-chimeric polypeptide, e.g. a polypeptide that comprises a functional unit derived from DAF, a functional unit that has been derived from CR1 and a functional unit that has been derived from IgG 4.

The present invention also provides isolated polynucleotides that encode the hybrid and chimeric polypeptides of the present invention, constructs formed by inserting an isolated polynucleotide of the present invention into an expression vector, and recombinant host cells into which the constructs of the present invention have been incorporated. In addition to the hybrid and/or chimeric polypeptide encoding sequence, such expression vectors comprise regulatory sequences that control or regulate expression of the polypeptide. Examples of suitable host cells are bacterial cells, yeast cells, insect cells, and mammalian cells. The present invention also relates to a process for preparing the hybrid and/or chimeric proteins of the present invention by culturing the cells of the present invention under conditions that promote expression of the hybrid and/or chimeric protein in the cell. For example, the process may be carried out by expressing the hybrid or chimeric protein in Chinese hamster ovary (CHO) cells or COS cells. The hybrid and chimeric proteins of the present invention may then be collected from a cell culture supernatant or cell lysate of the transformed host cells using an affinity column and then eluting the hybrid and/or chimeric protein from the column.

The present invention also features methods of reducing inflammation characterized by excessive complement activation in an animal subject. In one aspect, the method comprises administering one or more of the present hybrid polypeptides or chimeric polypeptides to an animal subject, particularly a human subject, afflicted with a condition associated with excessive complement activation. Thus, the present invention also relates to methods of treating patients afflicted with any of the diseases listed in Table 3 below. In another aspect, the present method comprises administering an expression vector comprising a polynucleotide that encodes a hybrid polypeptide or a chimeric polypeptide of the present invention to the animal subject.

DETAILED DESCRIPTION OF THE INVENTION

Described herein are hybrid proteins that comprise at least one functional unit of a first complement activation regulatory protein and at least one functional unit of a second complement activation regulatory protein, particularly a protein that inhibits the activity of C3 and/or C5 convertase. In certain embodiments, such hybrid proteins comprise more than one functional unit from a complement activation regulatory protein. In certain embodiments such hybrid proteins comprises functional units from more than 2 complement activation regulatory proteins. The functional units in the present hybrid proteins are separated and spaced apart by a spacer which is described in greater detail below. The functional units can be located in any order within the hybrid proteins of the present invention, provided that proper spacing exists between the functional units.

I. Hybrid Proteins

A. DAF Functional Unit

In certain embodiments, the present hybrid protein preferably comprises at least one functional unit from DAF. Such a functional unit is capable of dissociating C3 and C5 convertases. Thus, the DAF functional unit may comprise CCPs 2 and 3 of DAF, which are sufficient for decay accelerating activity against the classical pathway. Preferably, the DAF functional unit comprise CCPs 2, 3, and 4 of DAF, which are sufficient for decay accelerating activity against both the classical pathway C3 convertase and the alternative pathway C3 convertase. The amino acid sequence of such CCPs may be identical to the native or naturally occurring amino acid sequence of DAF. Alternatively, the amino acid sequence of such CCPs may be altered slightly, particularly at the amino or carboxy terminus. Such alterations occur when a restriction enzyme site is incorporated into the polynucleotide encoding the CCPs. Such alterations also occur when amino acids are deleted from the N terminus or C terminus of the functional unit. (For example, see Example 1 below in which a number of amino acids are deleted from the C terminus of CCP 4 of DAF.) In certain embodiments the hybrid protein may further comprise CCP 1 of DAF. It is also envisioned that some amino acid substitutions in the sequence may be introduced without effecting the activity of the functional until as disclosed in U.S. Pat. No. 6,521,450, the disclosure of which is hereby incorporated by reference herein. Therefore, the functional until may have less than complete homology to native protein component. Changes may be made by substitution of like charged amino acids for one another or substitution of hydrophilic amino acids for one another substitution of hydrophobic amino acids for one another and substitution of amino acids of similar mass for one another. In other regions, especially, those unassociated with activity less subtly changes may be made. In one embodiment, the protein contains a functional unit that has at least 95 percent homology to a region of CCPs 1, 2, 3 or 4 of the human DAF protein. The amino acid sequence of native DAF is shown in FIG. 1A (SEQ. ID NO: 1). CCP1 extends from and includes amino acid 35 through amino acid 95 of the native DAF protein. CCP2 extends from and includes amino acid through amino acid 97 through amino acid 159 of the native DAF protein. CCP3 extends from and includes amino acid 162-221 of the native DAF protein. CCP 4 extends from and includes 224-284 of the native DAF protein. The functional unit also comprises the amino acids that link CCP1 to CCP2, CCP2 to CCP3, and CCP3 to CCP 4 of the DAF protein.

B. CR1 Functional Units

The present hybrid protein may also comprise one or more functional units from CR1. Such functional unit is capable of acting as a cofactor for factor I-mediated cleavage of C3b to iC3b and C3f and further cleavage of iC3b to C3c and C3 dg. In this way, a hybrid protein may not only have strong activity in dissociating C3 convertase, but also strongly mediate further cleavage of the resulting C3b protein by factor I. Such a functional unit is also capable of acting as a cofactor for factor 1-mediated cleavage of C4b to C4d and Cr4c. (See K. Yazdanbakhsh et al., *Blood*, 2003). Thus, the hybrid protein of the present invention may comprise substantially all of CCPs 8-10 and/or CCPs 15-17 of CR1. The amino acid sequence of such CCPs may be identical to the native or naturally occurring amino acid sequence of CCPs 8-10 or CCPs 15-17 of CR1. Alternatively, the amino acid sequence of such CCPs may be altered slightly, particularly at the amino or carboxy terminus. Such alterations occur when a restriction enzyme site is incorporated into the polynucleotide encoding the CCPs 8-10 or CCPs 15-17 of CR1 or when amino acids, preferably a few amino acids, such as 1 to 10 aa's are deleted from the amino terminus or the carboxy terminus or both the amino terminus and the carboxy terminus of the functional unit. Amino acid substitutions, as described above, may also be introduced into the CCPs of CR1. The hybrid protein of the present invention may comprise two or more functional units from CR1. Such CR1 functional units may be the same or different. Thus, the hybrid protein of the present invention may comprise two functional units derived from LHR-B or one functional unit derived from LHR B and one functional unit derived from LHR-C of the CR1 protein. CCP 8 of CR1 extends from and includes amino acid 497-556 of the native CR1 protein. CCP 9 of CR1 extends from and includes amino acids 557-618 of the native CR1 protein. CCP 10 extends from and includes amino acids 619-688 of the native CR1 protein. CCP 15 of CR1 extends from and includes amino acid 947-1006 of the native CR1 protein. CCP 16 of CR1 extends from and includes amino acid 1007-1068 of the native CR1 protein. CCP 17 of CR1 extends from and includes amino acid 1069-1138 of the native CR1 protein.

C. MCP Functional Unit

The present hybrid protein may also comprise one or more functional units from MCP. Such functional unit is capable of acting as a cofactor for factor I-mediated cleavage of C3b to iC3b and C3f. Thus, the hybrid protein of the present invention may comprise substantially all of CCPs 1-4 of MCP. The amino acid sequence of such CCPs may be identical to the native or naturally-occurring amino acid sequence of CCPs 1-4 of MCP. Alternatively, the amino acid sequence of such CCPs may be altered slightly, particularly at the amino or carboxy terminus, or with substitutions as described above. Such alterations occur when a restriction enzyme site is incorporated into the polynucleotide encoding CCPs 1-4 of MCP, or when amino acids are deleted from the amino or carboxy terminus of this functional unit. Preferably, the hybrid protein of the present invention comprises two or more functional units from MCP or units having at least 95 percent homology to two or more functional units from MCP, or alternatively, a functional unit from MCP and a functional unit from CR1. CCP 1 of MCP extends from and includes amino acid 35-95 of the native MCP protein. CCP 2 of MCP extends from and includes amino acid 96-158 of the native MCP protein. CCP3 extends from and includes amino acid 159-224 of the native MCP protein. CCP4 extends from and includes amino acid 225-285 of the native MCP protein.

D. Spacer

The hybrid proteins of the present invention comprise one or more spacers. Each spacer in the present hybrid and/or chimeric proteins separate and appropriately space the functional units of the present hybrid and/or chimeric proteins from one another. Such spacer is a polypeptide that is greater than 200 amino acids in length, preferably greater than 250 amino acids in length. Where more than one spacer is required, the amino acid sequences of the spacers that are employed in the hybrid proteins of the present invention may be the same or different. In one preferred embodiment, the spacer comprises all or substantially all of CCPs 4-7 of CR1, i.e., amino acid 239 through amino acid 496 of the CR1 sequence shown in FIG. 2 (SEQ. ID NO: 3). In another preferred embodiment the spacer comprises all or substantially all of CCPs 11-14 of the CR1 protein. As used herein the term substantially all means that the spacer may lack a few, e.g. 1-10 amino acids from the N terminus and/or the C terminus of the spacer. The spacer may also comprise some amino acids that result from incorporating a restriction enzyme site into the spacer. Thus, the spacer may comprise a few amino acids at the N terminus or C terminus that are different from the amino acids that are found at the N terminus or C terminus of the CCP4-7 fragment that is derived from native CR1 or the CCP11-14 fragment that is derived from native CR1. The spaced may also contain substitutions within a sequence as described above, such that the spacer has at least about 95 percent homology to a corresponding native sequence.

Optionally, the hybrid proteins of the present invention may further include a tag, i.e., a second protein or one or more amino acids, preferably from about 2 to 65 amino acids, that are added to the amino or carboxy terminus of the hybrid protein. Typically, such additions are made to stabilize the protein or to simplify purification of an expressed recombinant form of the hybrid protein Such tags are known in the art. Representative examples of such tags include sequences which encode a series of histidine residues, the epitope tag FLAG, the Herpes simplex glycoprotein D, beta-galactosidase, maltose binding protein, or glutathione S-transferase.

The present invention also encompasses hybrid protein proteins in which one or more amino acids are altered by post-translation processes or synthetic methods. Examples of such modifications include, but are not limited to, glycosylation, iodination, myristoylation, and pegylation.

II. Chimeric Proteins.

The chimeric proteins of the present invention comprise one or more functional units of complement activation regulatory protein as described above and one or more functional units derived from a protein that is not a complement activation regulatory protein. Examples of functional units that are not derived from complement activation regulatory proteins include functional units that are derived from an immunoglobulin, particularly IgG4, and that serve to reduce degradation of the chimeric polypeptide following injection into an animal. Thus, the chimeric protein may include the hinge, CH2, and CH3 domains of IgG4. Alternatively, the second functional unit can be a targeting moiety that enhances binding of the chimeric polypeptide by certain animal tissues. An example of such targeting moiety is a lipid tail, as shown in attached FIG. 5. In certain embodiments, the chimeric protein may comprise multiple functional units that have been derived from one or more complement activation regulatory proteins, each of which are separated from one another by a spacer. Thus, the chimeric polypeptides of the present invention can be a hybrid, chimeric polypeptide.

Preparation of the Hybrid and Chimeric Proteins

The present hybrid proteins and chimeric proteins of the present invention are prepared using polynucleotides that encode such proteins and expression systems.

The functional units and spacers employed in the present hybrid and/or chimeric proteins can be made by obtaining total (t) or messenger (m) RNA from an appropriate tissue, cell line or white blood cells. Suitable RNA (total or messenger) is also available commercially. Blood can be drawn from a human or other animal subject and peripheral blood mononuclear cells (PBMCs) can be purified by Ficoll-Paque density centrifugation. Total RNA from PBMCs should contain CR1 and IgG4. Cell lines can be grown in controlled climate incubators with appropriate cell culture media. DAF and MCP are fairly ubiquitous proteins. Thus, these proteins can be found in most cell lines, e.g., the HeLa cell line.

Following isolation of suitable RNA, the RNA is reverse transcribed to cDNA using commerically available reagents and standard protocols, e.g., the Superscript protocol of Invitrogen. Once the appropriate cDNA is made, polymerase chain reaction (PCR) can be used in conjunction with DNA polymerases and oligonucleotide primer pairs (20 to 30 nucleotides in length) to amplify DAF, MCP, CR1 and/or IgG4 cDNA. One primer will be at the 5' end of the cDNA (for example at the start codon ATG or, in the case of the constant heavy chain, further downstream at the start of the constant heavy region 1 [CH1] and one primer will be at the 3' end of the cDNA, e.g. at the stop codon TAG, TAA, or TGA). The PCR products are then subcloned into vectors such as pT7Blue (pT7B) (Novagen, Madison, Wis.) and sequenced to confirm that the correct cDNA was amplified.

Expression Systems for Producing the Hybrid Proteins

The present hybrid proteins can be produced in procaryotic and eucaryotic cells each using different expression vectors that are appropriate for each host cell. Eucaryotic expression system such as the baculoviral or mammalian cells are described below.

The following are examples of expression vectors which may be used for gene expression in an eucaryotic expression system. The plasmid, pMSG, uses the promoter from mouse mammary tumor virus long terminal repeat (MMTV). Suitable host cells for pMSG expression are chinese hamster ovary (CHO) cells, HeLa cells and mouse Lkt negative cells (Lee, F., et al., 1981, Nature 294:228-232). The vector, pSVL, uses the SV40 late promoter. For high transient expression, suitable host cells for pSVL expression are COS cells (Sprague, J. et al., 1983, J. Virol. 45:773-781). The vector, pRSV, uses Rous Sarcoma Virus promoter. Suitable host cells for pRSV expression are mouse fibroblast cells, lymphoblastoid cells and COS cells (Gorman, Padmanabhan and Howard, 1983, Science 221:551-553).

Baculovirus expression vectors can also be used. These vectors are stably expressed in insect cells such as sf9 (Luckow, V. A. and Summers, M. D., 1988, Bio/Technology 6:47-55; Miller, L. K., 1988, Ann. Re. Microbiology 42:177-199).

Hybrid proteins of the invention can also be produced in a procaryotic expression system. The following are examples of expression vectors which can be expressed in procaryotic expression systems. The pOX expression series using the oxygen-dependent promoter can be expressed in *E. coli*. (Khosla, G., et al., 1990, Bio/Technology 8:554-558). pRL vector which uses the strong pL promoter of lambda phage (Reed, R. R., 1981, Cell 25:713-719; Mott, J. D., et al., 1985, Proc. Natl. Acad. Sci. U.S.A. 82:88-92) and the pKK223-3 vector which uses a hybrid promoter derived from the fusion between the promoters of the tryptophan and lactose operons of *E. coli*. (Borsius, J. and Holy, A., 1984, Proc. Natl. Acad. Sci. U.S.A. 81:6929-6933) can be used for expression in *E. coli*.

Suitable vectors for yeast expression are also well known in the art, e.g., Sleep, D., Belfield, D. P. and Goodey, A. R., 1990, Bio/Technology 8:42-46; Sakai, A. et al., 1991, Bio/Technology 9:1382-1385; Kotula, L. and Curtis, P. J., 1991, Bio/Technology 9:1386-1389, all of which are herein incorporated by reference.

Production, Quantitation, Purification and Analysis of the Hybrid Proteins.

Once a recombinant cell line that expresses the hybrid protein has been isolated, the secreted proteins are identified and verified with regard to their predicted structure. Various methods can be used to identify and characterize the expressed hybrid proteins. The presence of secreted hybrid proteins can be verified by immunoprecipitation with monoclonal antibodies to one or the other fragment, e.g., antibodies that bind to CCP's, 2, 3, or 4 of DAF or to LHR B or C of CR1.

Another method that could be used with present hybrid and/or chimeric proteins is a double immunoprecipitation, using two monoclonal antibodies of different specificities in succession. Pre-clearance of culture supernatant with one antibody would result in a negative immunoprecipitation with the second antibody. This method would verify that a single protein expresses both CR1 and DAF epitopes.

Alternatively, the hybrid DAF-CR1 protein, can be identified by Western blot. For example, after SDS-PAGE and transfer to nitrocellulose, blots can be developed with either anti-CR1 antibodies or anti-DAF monoclonal antibodies. The expressed bispecific recombinant protein would be reactive with both antibodies, again demonstrating the presence of specific DAF and CR1 epitopes in the hybrid protein.

Identification of the present hybrid and/or chimeric proteins can also be accomplished by ELISA. For example, a rabbit polyclonal antibody specific for either LHR B or C of CR1 or CCP's 2, 3, or 4 of DAF can be used to coat plastic microtiter ELISA plates, followed by the addition of culture supernatant from the recombinant cell line expressing the DAF-CR1 hybrid and incubation with the capture polyclonal antibody. A monoclonal anti-DAF or anti-CR1 second antibody, the specificity of which is different from the capture antibody, can be subsequently used. A positive reaction would indicate the presence of both epitopes on the hybrid or chimeric protein.

An ELISA can also be used to quantitate the levels of the DAF-CR1 hybrid protein in culture supernatants or any other unpurified solutions containing the chimeric protein by comparison to standard curve of known quantities of purified DAF-CR1 hybrid protein. Quantitation of DAF-CR1 hybrid protein would be useful for determination of production rates in recombinant cell lines, determination of protein concentration in partially purified preparations, and for determination of protein concentration in plasma for in vivo experiments.

The hybrid and/or chimeric proteins of the present invention can be purified from recombinant cell culture supernatant by a variety of standard chromatographic procedures, including but not limited to immunoaffinity chromatography, ion exchange chromatography, gel filtration chromatography, reverse-phase high pressure liquid chromatography (HPLC), lectin affinity chromatography, or chromatofocusing. For example, small quantities of culture supernatant containing serum supplement can be purified using immunoaffinity chromatography with, e.g., anti-CR1 or anti-DAF monoclonal antibodies. DAF-CR1 hybrid protein bound to the immobilized antibody can be eluted in purified form by use of a chaotropic solution.

Once the hybrid and/or chimeric protein is purified, its amino acid sequence can be deduced by direct protein sequence analysis using an automated system. The presence of N- and O-linked carbohydrates can be determined by use of specific endoglycosidase enzymes (Chavira, R. et al., 1984, Anal. Biochem. 136:446). Further characterizations of its biochemical structure can also be performed, including but not limited to pI determination by isoelectric focusing, hydrophilicity analysis, X-ray crystallographic analysis, and computer modeling.

Functional Characterization of the Present Hybrid and/or Chimeric Proteins

The hybrid proteins of the present invention have the ability to function both as a cofactor for Factor I and as a decay accelerating factor. In vitro assays can be performed to measure these biological activities (Medof, M. et al., 1984, J. Exp.

Med. 160:1558; Masaki, T. et al., 1992, J. Biochem 111:573). As described in the examples, assays for cofactor activity and for decay accelerating activity are used to demonstrate both these complement regulatory functions for the present hybrid protein. The consequence of either cofactor or decay accelerating activity, or in the case of a DAF-CR1 or DAF-MCP hybrid protein, both activities in combination, is the inactivation of C3/C5 convertases. Another suitable in vitro assay demonstrates that the present hybrid protein is capable of inhibiting C5 convertase activity as measured by the production of C5a. (Moran, P. et al., 1992, J. Immunol. 149:1736, herein incorporated by reference). Additional assays, as described in the examples below, demonstrate that the present hybrid proteins inhibit the complement-induced lysis of cells via the classical and alternative pathways.

Demonstration of In Vivo Therapeutic Activity of the Present Hybrid and/or Chimeric Proteins The Arthus reaction is an inflammatory response caused by the interaction of antigen in tissue with circulating antibody. It has been used as a classic example of a localized in vivo inflammatory response, and is characterized by the formation of immune complexes, complement activation, inflammatory cell recruitment, edema and tissue damage (Bailey, P. and Sturm, A., 1983, Biochem. Pharm 32:475). Experimentally, a reversed passive Arthus reaction can be established in an animal model by i.v. injection with antigen and subsequent challenge with antibody. Using guinea pigs as an animal model, the in vivo therapeutic efficacy of the hybrid and/or chimeric proteins of the invention can be evaluated.

Additional animal models with relevance to various clinical human diseases can also be used to test the in vivo efficacy of complement activation blockers. These include, but are not limited to: myocardial ischemia/reperfusion injury (acute myocardial infarction; Weisman, H. F. et al., 1990, Science 249:146); cerebral ischemic injury (stroke; Chang, L. et al., 1992, J. Cerebr. Blood Flow Metab. 12:1030); lung injury (ARDS; Hosea, S. et al., 1980, J. Clin. Invest. 66:375); xenograft rejection (transplants; Leventhal, J. et al., 1993, Transplantation 55:857); burn injury (Caldwell, F, et al., 1993, J. Burn Care Rehab. 14:420); acute pancreatitis (Steer, M. 1992, Yale J. Biol. Med. 65:421), nephritis (Pichler, R. et al., 1994, Am. J. Pathol. 144:915), cardiopulmonary bypass (Nilsson, L. et al., 1990, Artif. Organs 14:46), and multiple sclerosis (Linington, C. et al., 1989, Brain 112:895).

Administration of the Present Hybrid and Chimeric Proteins to Animal Subjects

The present hybrid and chimeric proteins can be combined with an appropriate pharmaceutical formulation and administered to an animal subject, particularly a human subject, by a variety of routes, including, but not limited to, intravenous bolus injection, intravenous infusion, intraperitoneal, intradermal, intramuscular, subcutaneous, and intranasal routes. The administration of the present hybrid proteins in vivo will enable the protein to bind endogenous C3/C5 convertases and inhibit the generation of additional C3b and C5b, of C3a and C5a anaphylatoxins, and of C5b-9 lytic complexes. The complement regulatory activities of the present hybrid proteins can therefore function to inhibit in vivo complement activation and the inflammatory sequelae that accompany it, such as neutrophil recruitment and activation, autolysis of host cells, and edema. The present hybrid and/or chimeric proteins can be used for the therapy of diseases or conditions that are mediated by inordinate and/or excessive activation of the complement system. These include, but are not limited to: tissue damage due to ischemia-reperfusion following myocardial infarction, aneurysm, stroke, hemorrhagic shock, or crush injury; burns; endotoxemia and septic shock; adult respiratory distress syndrome (ARDS); hyperacute rejection of grafts; cardiopulmonary bypass and pancreatitis. Autoimmune disorders including, but not limited to, systemic lupus erythematosis, rheumatoid arthritis, and multiple sclerosis, can also be treated with the hybrid and/or chimeric proteins of the invention (also see Table 3).

Various delivery systems are known and can be used to deliver the hybrid and/or chimeric proteins of the invention, such as encapsulation in liposomes, or controlled release devices. The hybrid and/or chimeric proteins of the invention can also be administered extracorporeally, e.g., pre-conditioning donor organs prior to transplantation. The hybrid and/or chimeric proteins of the invention can be formulated in a pharmaceutical excipient in the range of approximately 10 µg/kg and 10 mg/kg body weight for in vivo or ex vivo treatment.

Administration of Polynucleotides that Encode the Present Hybrid and/or Chimeric Proteins to an Animal Subject The present invention also relates to therapeutic methods in which polynucleotides that encode and express the present hybrid and/or chimeric polypeptides are introduced into a subject in need of the same, i.e. a subject, particularly a human subject, with a disorder associated with increased complement activation. Polynucleotides encoding and expressing one or more hybrid and/or chimeric polypeptide can be introduced into cells of the subject using any of a variety of methods known in the art to achieve transfer of DNA molecules into cells. For example, DNA encoding and expressing the hybrid and/or chimeric polypeptide can be incorporated into liposomes and targeted to and internalized by the cells of the subject. Polynucleotides encoding the hybrid and/or chimeric polypeptide can also be incorporated into plasmids that are introduced into cells of the subject by transfection. The hybrid and/or chimeric polypeptide encoding polynucleotides can also be introduced into cells using viruses. Such viral "vectors" can have DNA or RNA genomes. Numerous such viral vectors are well known to those skilled in the art. Viral vectors that have polynucleotide sequences encoding a DAF-CR1 hybrid polypeptide, for example, cloned into their genomes are referred to as "recombinant" viruses. Transfer of DNA molecules using viruses is particularly useful for transferring polynucleotide sequences into particular cells or tissues of an animal. Such techniques are commonly known in the art as gene therapy.

Expression vectors normally contain sequences that facilitate gene expression. An expression vehicle can comprise a transcriptional unit comprising an assembly of a protein encoding sequence and elements that regulate transcription and translation. Transcriptional regulatory elements generally include those elements that initiate transcription. Types of such elements include promoters and enhancers. Promoters may be constitutive, inducible or tissue specific. Transcriptional regulatory elements also include those that terminate transcription or provide the signal for processing of the 3' end of an RNA (signals for polyadenylation). Translational regulatory sequences are normally part of the protein encoding sequences and include translational start codons and translational termination codons. There may be additional sequences that are part of the protein encoding region, such as those sequences that direct a protein to the cellular membrane, a signal sequence for example.

The hybrid and/or chimeric polypeptide encoding polynucleotides that are introduced into cells are preferably expressed at a high level (i.e., the introduced polynucleotide sequence produces a high quantity of the hybrid and/or chimeric polypeptide within the cells) after introduction into the cells. Techniques for causing a high-level of expression of polynucleotide sequences introduced into cells are well known in the art. Such techniques frequently involve, but are not limited to, increasing the transcription of the polynucleotide sequence, once it has been introduced into cells. Such techniques frequently involve the use of transcriptional promoters that cause transcription of the introduced polynucleotide sequences to be initiated at a high rate. A variety of such promoters exist and are well known in the art. Frequently, such promoters are derived from viruses. Such promoters can result in efficient transcription of polynucleotide sequences in a variety of cell types. Such promoters can be constitutive (e.g., CMV enhancer/promoter from human cytomegalovirus) or inducible (e.g., MMTV enhancer/promoter from mouse mammary tumor virus). A variety of constitutive and inducible promoters and enhancers are known in the art. Other promoters that result in transcription of polynucleotide sequences in specific cell types, so-called "tissue-specific promoters," can also be used A variety of promoters that are expressed in specific tissues exist and are known in the art. For example, promoters whose expression is specific to neural, liver, epithelial and other cells exist and are well known in the art. Methods for making such DNA molecules (i.e., recombinant DNA methods) are well known to those skilled in the art.

In the art, vectors refer to nucleic acid molecules capable of mediating introduction of another nucleic acid or polynucleotide sequence to which it has been linked into a cell. One type of preferred vector is an episome, i.e., a nucleic acid capable of extrachromosomal replication. Other types of vectors become part of the genome of the cell into which they are introduced. Vectors capable of directing the expression of inserted DNA sequences are referred to as "expression vectors" and may include plasmids, viruses, or other types of molecules known in the art.

Typically, vectors contain one or more restriction endonuclease recognition sites which permit insertion of the hybrid polypeptide encoding sequence. The vector may further comprise a marker gene, such as for example, a dominant antibiotic resistance gene, which encode compounds that serve to identify and separate transformed cells from non-transformed cells.

One type of vector that can be used in the present invention is selected from viral vectors. Viral vectors are recombinant viruses which are generally based on various viral families comprising poxviruses, herpesviruses, adenoviruses, parvoviruses and retroviruses. Such recombinant viruses generally comprise an exogenous polynucleotide sequence (herein, a polynucleotide encoding the hybrid and/or chimeric polypeptide) under control of a promoter which is able to cause expression of the exogenous polynucleotide sequence in vector-infected host cells.

One type of viral vector is a defective adenovirus which has the exogenous polynucleotide sequence inserted into its genome. The term "defective adenovirus" refers to an adenovirus incapable of autonomously replicating in the target cell. Generally, the genome of the defective adenovirus lacks the sequences necessary for the replication of the virus in the infected cell. Such sequences are partially or, preferably, completely removed from the genome. To be able to infect target cells, the defective virus contains sufficient sequences from the original genome to permit encapsulation of the viral particles during in vitro preparation of the construct. Other sequences that the virus contains are any such sequences that are said to be genetically required "in cis."

Preferably, the adenovirus is of a serotype which is not pathogenic for man. Such serotypes include type 2 and 5 adenoviruses (Ad 2 or Ad 5). In the case of the Ad 5 adenoviruses, the sequences necessary for the replication are the E1A and E1B regions. Methods for preparing adenovirus vectors are described in U.S. Pat. No. 5,932,210, U.S. Pat. No. 5,985,846, and U.S. Pat. No. 6,033,908.

More preferably, the virus vector is an immunologically inert adenovirus. As used herein the term "immunologically inert" means the viral vector does not encode viral proteins that activate cellular and humoral host immune responses. Methods for preparing immunologically inert adenoviruses are described in Parks et al., *Proc Natl Acad Sci USA* 1996; 93(24) 13565-70; Leiber, A. et al., *J. Virol.* 1996; 70(12) 8944-60; Hardy s., et al, *J. Virol.* 1997, 71(3): 1842-9; and Morsy et al, *Proc. Natl. Acad. Sci. USA* 1998. 95: 7866-71, all of which are specifically incorporated herein by reference. Such methods involve Cre-loxP recombination. In vitro, Cre-loxP recombination is particularly adaptable to preparation of recombinant adenovirus and offers a method for removing unwanted viral nucleotide sequences. Replication deficient recombinant adenovirus lacks the E1 coding sequences necessary for viral replication. This function is provided by 293 cells, a human embryonic kidney cell line transformed by adenovirus. First generation adenoviruses are generated by co-transfecting 293 cells with a helper virus and a shuttle plasmid containing the foreign gene of interest. This results in the packaging of virus that replicates both the foreign gene and numerous viral proteins. More recently, 293 cells expressing Cre recombinase, and helper virus containing essential viral sequences and with a packaging signal flanked by loxP sites, have been developed (See Parks et al.) In this system, the helper virus supplies all of the necessary signals for replication and packaging in trans, but is not packaged due to excision of essential sequences flanked by loxP. When 293-Cre cells are co-transfected with this helper virus, and a shuttle plasmid (pRP1001) containing the packaging signal, nonsense "filler DNA", and the foreign gene, only an adenovirus containing filler DNA and the foreign gene is packaged (LoxAv). This results in a viral recombinant that retains the ability to infect target cells and synthesize the foreign gene, but does not produce viral proteins.

Another type of viral vector is a defective retrovirus which has the exogenous polynucleotide sequence inserted into its genome. Such recombinant retroviruses are well known in the art. Recombinant retroviruses for use in the present invention are preferably free of contaminating helper virus. Helper viruses are viruses that are not replication defective and sometimes arise during the packaging of the recombinant retrovirus.

Non-defective or replication competent viral vectors can also be used. Such vectors retain sequences necessary for replication of the virus. Other types of vectors are plasmid vectors.

The methods also involve introduction of polynucleotides encoding the present hybrid and/or chimeric polypeptides into an animal subject in the context of cells (e.g., ex vivo gene therapy).

EXAMPLES

The following examples contained herein are intended to illustrate but not limit the invention.

Example 1

Hybrid Protein DAF-CR1B

A hybrid protein, DAF-CR1B, comprising a decay accelerating functional unit derived from DAF, a cofactor 1 functional unit derived from CR1, and a spacer comprised of CCPs 4-7 of CR1 was made by recombinant techniques. The DAF portion of the hybrid protein DAF-CR1B was constructed using DAF13.2.1/pBTKS and two primers DSIGEB and DAF3P in a PCR reaction (Vent polymerase [New England Biolabs] with the following times: 94° C. 3 min [initial melting]; 94° C. 1 min, 55° C. 1 min 15 sec, 72° C., 1 min 15 sec for 25 cycles; and 72° C. 7 min [final extension]). DSIGEB is a 42 nucleotide ("nt") primer that has the sequence 5'-ATA TAC GAA TTC AGA TCT ATO ACC GTC GCG CGG CCG AGC GTG-3' (FIG. 6A SEQ. ID NO:7). DAF3P is a 35 nt primer that has the sequence 5'-ACA GTG CTC GAG CAT TCA GGT GGT GGG CCA CTC CA-3' (FIG. 6B, SEQ. ID NO:8). The resultant PCR product was named DAF1. It contained DAF's signal sequence followed by CCPs 1, 2, 3 and 4 ending with cysteine 249 (Cys-249) in CCP4. Upstream of the signal sequence, two restriction enzyme sites were built in, BglII (A▼GATCT) and 5' of BglII, EcoRI (G▼AATTC). Three prime (3') of CCP4 and encompassing part of the Cys-249 codon (TGC), the restriction enzyme site XhoI (C▼TCGAG) was inserted. DAF1 was subcloned into pT7B and fully sequenced.

The CR1 portion of the hybrid protein DAF-CR1B was constructed using CR1/AprM8. CR1/AprM18 was cut with the restriction enzyme NsiI (ATGCA▼T) releasing several pieces, two of which were recovered (1094 nts and 1350 nts) and subcloned into pGEM7Zf(+). The "1094" fragment (encompassing nts 557 to 1670 of CR1) was amplified by PCR using the primers CR1094X(5') and CR1094N(3'). CR1094X is a 41 nt primer having the sequence 5'-ATA TAC CTC GAG TCC TAA CAA ATG CAC GCC TCC AAA TGT GG-3' (FIG. 7A, SEQ ID NO:9). It has an XhoI site. CR1094N is a 34 nt primer having the sequence 5'-ACA GTG ATG CAT TGG TTT GGG TTT TCA ACT TGG C-3' (FIG. 7B, SEQ ID NO:10). It has an NsiI site. This set of primers produces a sequence from the linker between CCP3 and CCP4 of CR1 into CCP8 of CR1. PCR conditions were the same as those for DAF1. The "1350" fragment, encompassing nts 1671 to 3020 of CR1, was amplified by PCR using primers CR1350N(5') and CR1B3P(3'). CR1350N is a 41 nt primer having the sequence 5'-ATA TAC ATG CAT CTG ACT TTC CCA TTG GGA CAT CTT TAA AG-3' (FIG. 7C, SEQ ID NO: 11). It has an NsiI site. CR1B3P is a 57 nt primer having the sequence 5'-ACA GTG AGA TCT TTA GTG ATG GTG ATG GTG ATG AAT TCC ACA GCG AGG GGC AGG GCT-3' (FIG. 7D, SEQ ID NO: 12). It has a BglII site. PCR conditions were the same as those for DAF1 except the 25 cycle extension time at 72° was 2 min, not 1 min 15 sec. This set of primers produces a sequence from CCP8 of CR1 to the end of CCP14 (in LHRB, specifically, . . . SSPAPRCGI) with a C-terminal 6×His tag and stop codon. These PCR fragments were subcloned into pT7B.

It is noteworthy that the natural linker between CCP3 and CCP4 of CR1 is the amino acid sequence "IIPNK" (see FIG. 2, SEQ. ID NO: 3). Due to the insertion of the XhoI restriction site, the hybrid protein's linker between DAF CCP4 and CR1 CCP4 is "SSPNK" (see FIG. 8A (SEQ. ID NO: 13).

DNA sequence the data obtained confirmed the presence of the correct nucleotide sequences.

The vector pSG5 (Stratagene) was cut with the restriction enzymes EcoRI and BglII to accommodate the insertion of DAF1 (EcoRI to XhoI), CR828XN3(XhoI to NsiI) and CR1300NBF (NsiI to BglII). The vector and the three fragments were ligated using Promega T4 DNA ligase, and transformed into DH5α maximum efficiency competent cells. Agarose gel electrophoresis confirmed the presence of the vector and insert. The cDNA from one colony was used for transfection into COS cells using Lipofectamine (Invitrogen) reagent. The supernatant was harvested two days later. Western blots using 2H6, an anti-DAF CCP4 antibody, and an anti-His tag antibody indicated the presence of the hybrid protein. The amino acid sequences of the DAF-CR1B is provided in FIG. 8A (SEQ. ID NO: 13). A DNA sequence encoding DAF-CR1B is provided in FIG. 8B (SEQ. ID NO: 14).

Example 2

Hybrid Protein DAF-CR1BB

Another hybrid protein, DAF-CR1BB, was prepared by recombinant techniques. DAF-CR1BB, comprises DAF's four CCPs, a spacer comprised of CCPs 4-7 of CR1, separating the functional unit of DAF from a first cofactor 1 functional unit of CR1, LHR B, and a second spacer, CCPs 11-14 of CR1, separating the first cofactor 1 functional unit of CR1 from the second cofactor 1 functional unit of CR1, also LHR B. More specifically, DAF-CR1BB was prepared by adding an additional LHRB of CR1 to DAF-CR1B To add the additional cofactor LHR, DAF CR1B was cut with BamHI and a BamHI fragment (nucleotide #1861 to 3210) from CR1 in AprM8 was introduced. The BamHI fragment could enter the plasmid in either the correct or reverse orientation. Screening with SmaI found several clones with the correct nucleotide orientation. The amino acid sequence of DAF-CR1BB is provided in FIG. 9A (SEQ ID NO: 15). The DNA sequence encoding DAF-CR1BB is provided in FIG. 9B (SEQ ID NO: 16)

Example 3

Chimeric Protein DAF –Ig G4

To increase half life of the hybrid protein, while minimizing complement activation, as a starting point, part of the constant heavy region of IgG4 was amplified by PCR and connected 3' to nucleotides encoding a decay accelerating functional unit derived from DAF, and a spacer derived from CR1. The resulting protein DAF-IgG4, is composed of DAF CCPs1,2,3,4+CR1 CCP4,5,6,7 (part of LHRA)+IgG4, last amino acid (valine) of CH1-Hinge-CH2-CH3. The domains of IgG4 were amplified by PCR from pHC-huCg4, a gift of Gary McLean, 2222 Health Sciences Mall, Vancouver, B.C., Canada. The primers used in this PCR reaction were:

```
IgG45:
                            (FIG. 10A (SEQ ID NO: 17))
5'-ATA TAC GAA TTC TGG TTG AGT CCA AAT ATG GTC
CC-3'
and IgG43:
                            (FIG. 10B (SEQ ID NO: 18))
5'-ACA GTG AGA TCT TTA TCA TTT ACC CGG AGA CAG
GGA G-3'.
```

Per 100 µl PCR reaction, 2U Vent polymerase (New England Biolabs), 71.5 ng pHC-Cg4 (7157 bp), 50 µmol of each primer, and 10 mM of each dNTP were used. PCR settings were 1 initial denaturing cycle of 94° C. 3 min; 25 cycles of 94° C. 1 min, 55° C. 1 min 15 sec, and 72° C. 1 min; and a final extension cycle of 72° C. 7 min. A 700 bp fragment was recovered with the QIAquick gel purification kit. The fragment "IgG4 PCR" was ligated into the pT7Blue (pT7B) blunt vector (Novagen). Nova Blue (Novagen) and XL1Blue (Stratagene) competent cells were transformed with the ligation mixture and plated on Ampicillin 50, Tetracycline 15, IPTG/Xgal LB agar plates. DNA sequence data confirmed the presence of the correct nucleotide sequence. A DNA sample was subsequently cut with EcoRI ("E") and BglII ("B") in Promega Buffer H ("H") and the 700 bp band was purified with QIAquick. IgG41 E/B and pSG5 E/B/H were ligated using the Quick Ligation method (New England Biolabs) and transformed into DH5αmax (Invitrogen) competent cells. The presence of the correct inserts was confirmed by digestion with EcoRI and BglII in Buffer H (Promega).

The resulting plasmid was cut with EcoRI (~4800 bp linearized), purified, shrimp alkaline phosphatase ("SAP")-treated, purified again, and quick ligated to an/EcoRI-cut fragment (gel purified, 1650 bp) which contains the DAF and CR1 portions of the sequence. DH5αmax competent cells were transformed with the ligation mix. Plasmid DNA from resulting colonies were screened by cutting the DNA with BglII and examining the resulting band by agarose gel electrophoresis. Plasmid DNA was purified and cDNA was checked (uncut and BglII-cut). The amino acid sequence of DAF-IgG4 is provided in FIG. 11A (SEQ. ID NO: 19). The DNA sequence encoding DAF-IgG4 is provided in FIG. 11B (SEQ. ID NO: 20) The cDNA was transfected into COS cells.

Note that the IgG45 primer codes for a slightly different link between CR1 CCP7 and the Hinge of IgG4 (in DAF-IgG4) than the link between CR1 CCP7 and MCP CCP1 (in "DAF-MCP" see Example 4). IgG45 results in "GILV" ("V" is the last amino acid of the CH1 domain of IgG4) instead of "GILGH" which is found in DAF-MCP and is also the normal link between CR1 CCP7 and CCP8 (and is therefore what is found in DAF-CR1B and DAF-CR1BB hybrids).

Example 4

Hybrid Protein DAF-MCP

A hybrid protein, referred to hereafter as DAF-MCP, comprising a decay accelerating functional unit of DAF, a cofactor 1 functional unit derived from MCP, and a spacer derived from CR1 was prepared (DAF CCPs 1,2,3,4-CR1 CCPs 4,5,6,7-MCP CCPs 1,2,3,4+ 2 amino acids (VS) of MCP STP region+6×His). MCP cDNA (with 3'-end sequence encoding GPI-anchor addition) in PEE14 was used. More MCP cDNA in DH5α (Wizard SV DAF-IgG4-prep) ("MCP-GPI (A)") was subsequently prepared. Primers for the MCP portion of DAF-MCP are:

```
MCP5:
                          (FIG. 12A, SEQ ID NO: 21)
5'-ATA TAC GAA TTC TGG GTC ACT GTG AGG AGC CAC

CAA CAT TTG AAG C-3';
and

MCP3:
                          (FIG. 12B, SEQ. ID NO: 22)
5'-ACA GTG AGA TCT TTA GTG ATG GTG ATG GTG ATG

CGA CAC TTT AAG ACA CTT TGG AAC-3'.
```

The PCR reaction used Vent polymerase from New England Biolabs. The MCP PCR fragment was cut with EcoRI ("E") and BglII ("B") in Promega Buffer H ("H"). The Quick Ligase method (New England Biolabs) was used to ligate E/B/H-cut MCP PCR and E/B/H-cut pSG5. DH5α maximum efficiency competent cells were transformed with the mixture. Colonies were picked, the DNA was extracted from the bacteria and cut with E/B/H. All had an insert. Two DNA samples were sequenced. An error at Nucleotide 680 was found which changes the amino acid at that position. Primers were made to perform site-directed mutagenesis to correct the error (not shown). Subsequent DNA sequence data confirmed the correct sequence.

The resulting DNA was cut with EcoRI in Buffer H and purified with Qiagen PCR purification kit. The purification product was treated with shrimp alkaline phosphatase ("SAP"), and purified again. Quick ligation method was used to ligate EcoRI- and SAP-treated MCP1A/pSG5 and EcoRI-treated and gel purified 1650 base pair piece from DAF-CR1BA which adds the DAF and CR1 portions of the cDNA. After transformation, plasmid DNA was cut with BglII or with EcoRI to confirm the presence and correct orientation of the insert. The amino acid sequence of DAF-MCP is provided in FIG. 13A (SEQ. ID NO: 23). A DNA sequence of DAF-MCP is provided in FIG. 13 B (SEQ. ID NO: 24).

DNA was used for COS cell transfection. DAF-MCP 5A protein was visualized by western blot with monoclonal antibodies IA10 (against DAF CCP1) and GB24 (against MCP CCPs 3 and 4) (not shown). Size was between 90 kDa and 100 kDa.

Testing of the Hybrid Proteins

Hemolytic Assays

Hemolytic assays are performed to assess the activity of the components of the classical and alternative pathways of complement or the activity of the regulators of complement activation (RCA) proteins. Classical pathway activity is assessed using antibody-sensitized sheep erythrocytes (EshA) and can be undertaken in a variety of ways. Whole serum can be used, or purified components of the complement cascade can be used in a classical pathway C3 or C5 convertase hemolytic assay.

Experiments were undertaken using normal human, pig and rat serum to assess animal models for study. Human DAF has been found to be active against convertases formed in pig serum (J. M. Perez de la Lastra et al. 2000, *J. Immunol.* 165:2563). It is active at high concentrations against convertases formed in rat serum (C. L. Harris et al., 2000, *Immunology* 100:462). In contrast, human CR1 is highly active against convertases formed in rat serum. Classical pathway C3 convertase and C5 convertase assays utilizing purified human complement components were also done to compare the hybrids' performance to soluble DAF and soluble CR1.

Whole Serum Experiments

Serum (human, pig or rat) was titrated to a Z score of approximately 1, defined as an average of 1 lesion per sheep cell (A. P. Gee, 1983, "Molecular Titration of Components of the Classical Complement Pathway" in *Methods in Enzymology* 93:339). To each tube was added $1 \times 10^7$ EshA, an RCA protein and the serum in DGVB++ (dextrose gelatin veronal buffer with calcium and magnesium) to a total volume of 200 ul. This mixture was shaken for 30 min in a 37° C. water bath. GVBE (gelatin veronal buffer with EDTA) was subsequently added to stop the hemolytic reaction. The extent of lysis was determined by reading the $OD_{412}$ of the hemoglobin red supernatant.

Classical Pathway C3 Convertase Hemolytic Assay

EshA ($1 \times 10^7$ cells/tube) were sequentially shaken and spun down with 30SFU (site-forming units) of human C1 (ART) for 15 min, 15SFU of human C4 (Quidel) for 20 min, and sufficient human C2 (ART) for a Z score of 1 for 5 min, all at 30° C. Following formation of the classical pathway C3 convertase C4b2a, regulators were added for 15 min at 30° C. to assess their relative decay-accelerating activity. Guinea pig serum in GVBE (1:40 dilution) was subsequently added for 1 hr at 37° C. to allow formation of the terminal membrane complex. The cells were spun down and the OD$_{412}$ of the hemoglobin red supernatant was read to determine the extent of cell lysis.

Classical Pathway C5 Convertase Hemolytic Assay

The classical pathway C5 convertase hemolytic assay was run over a 2-day period. EshA (1×10$^7$ cells/tube) were shaken sequentially with 60SFU of human C1 (ART) for 15 min, 60SFU of human C4 (Quidel) for 20 min, and 10SFU human C2 (calculated after decay in a C3 convertase assay) (ART) along with 15SFU of human C3 (gift of C. Mold) for 5 min, all in a 30° C. water bath, to form the classical pathway C5 convertase C4b3b2a. Following this loading of complement components, 200 ul DGVB++ was added to each tube and the tubes were shaken for 2 hr in a 30° C. water bath to decay the C2. The cells were spun down, resuspended in DGVB++, and decay continued overnight with the cells at 4° C. The following day, the cells were shaken with 60SFU of human C1 for 15 min in a 30° C. water bath, followed by sufficient human C2 for a Z score of 1 (5 min, 30° C.). RCA proteins were added for 15 min at 30° C. to accelerate the decay of the C5 convertase. Subsequently, human C5 (Quidel) (1:250 dilution) was added for 5 min at 30° C., then guinea pig C6-9 in DGVBE (dextrose gelatin veronal buffer with EDTA) (1:150 dilution) for 1 hr at 37° C. Cells were spun down and the OD$_{412}$ of the hemoglobin red supernatant was read to determine the extent of cell lysis.

Cofactor Experiments

The RCA proteins CR1, factor H and membrane cofactor protein MCP can act as cofactors for the factor I cleavage of C3b to smaller fragments (reviewed in M. Botto, "C3" [p. 88] in The Complement FactsBook, ed. B. J. Morley and M. J. Walport, 2000, San Diego: Academic Press). The cofactor activity of CR1 resides in its LHRs B and C(S. C. Makrides et al., 1992, *J. Biol. Chem.* 267:24754; K. R. Kalli et al., 1991, *J. Exp. Med.* 174:1451; M. Krych et al., 1994, *J. Biol. Chem.* 269:13273). All three regulators can allow factor I to cleave C3b to iC3b. Factor I with CR1 can additionally cleave to iC3b to C3c. When the disulfide bridges are reduced, an SDS-PAGE (sodium dodecyl sulfate-polyacrylamide gel electrophoresis) gel will show the following bands:

C3b: α' (15 kDa), β (75 kDa)

iC3b: α'-68, α'-43, β (75 kDa), and a small soluble fragment C3f

C3c: α'-27, α'-40, β(75 kDa), and "membrane-attached" C3dg (40 kDa)

(A. Sahu et al., 1998, *J. Immunol.* 160:5596; A. M. Rosengard et al., 2002 *PNAS* 99:8808).

To confirm that the hybrid retained the cofactor activity of CR1, human C3b (ART Lot 20P, 20 ng), was mixed with human factor I (ART Lot 6P, 60 ng). Factor H (500 ng) or DAF-CR1BB (20 ng) or a control of 10 mM PO4 buffer with 145 mM NaCl, pH 7.3 was added for a total volume of 10 ul and incubated for 19 hr in a 37° water bath.

Figure 14:
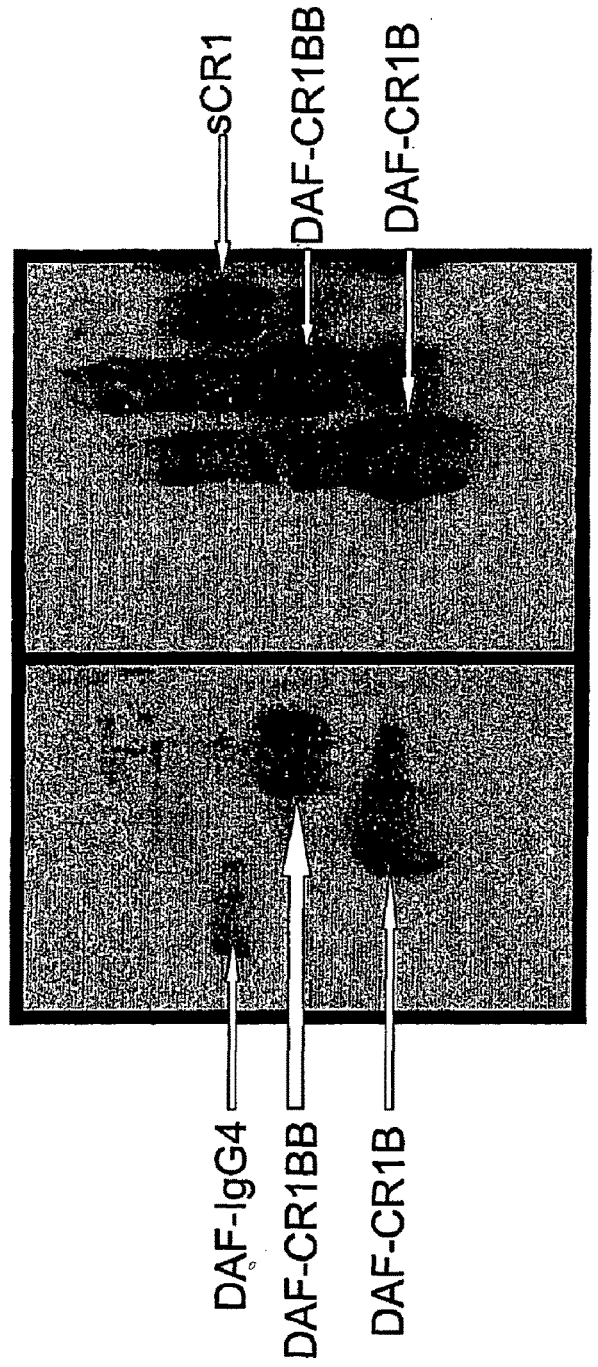
FIG. 14 is a Western blot of protein samples containing hybrid proteins probed with monoclonal antibodies raised against DAF and CR1.

Samples of DAF-CR1B, DAF-CR1BB, and DAF-IgG4 separated on a 5% SDS polyacrylamide gel and were examined by Western blot using monoclonal antibodies raised against DAF (IA10) or CR1 (E11) as shown in FIG. 14. Results indicated that the expressed hybrid proteins were recognized by antibodies to DAF or CR1 as expected.

Figure 15:
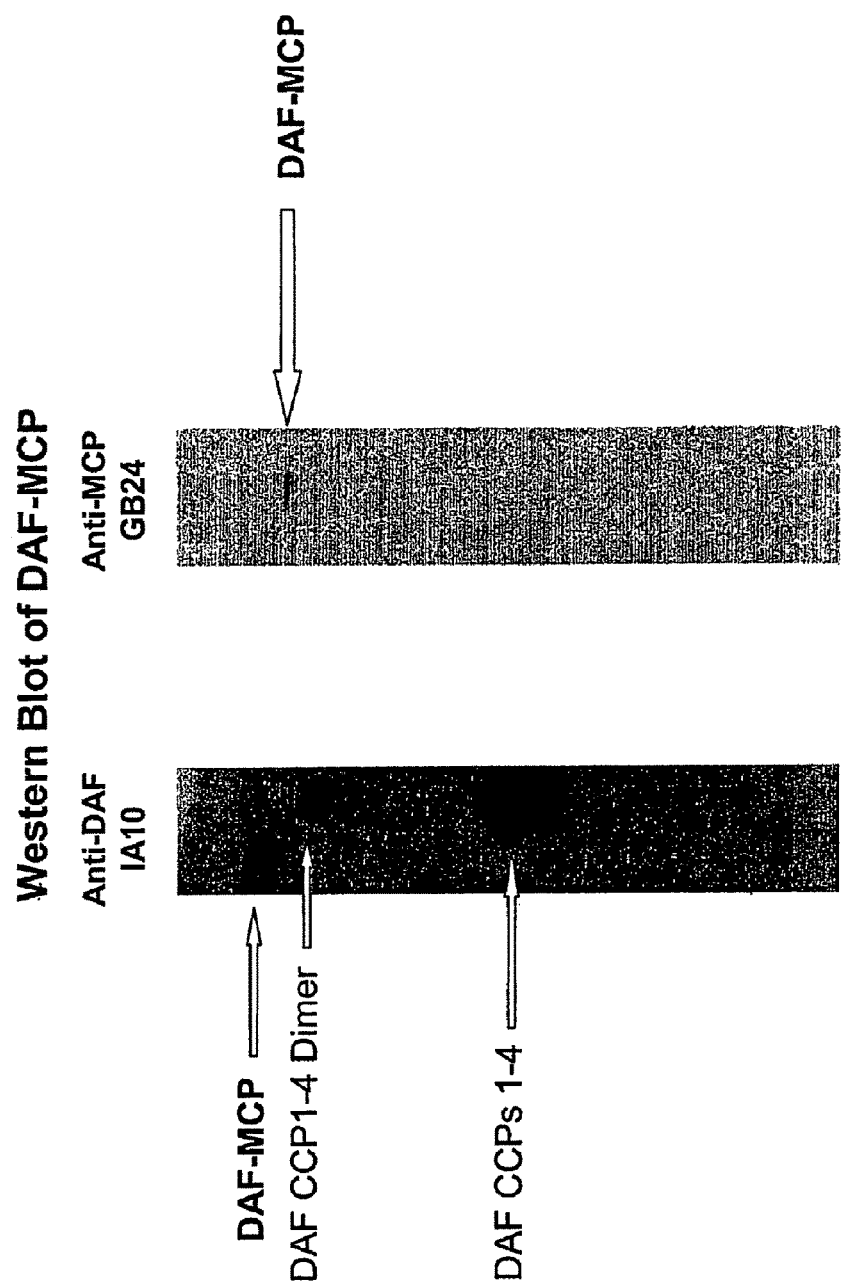
FIG. 15 is a Western blot of a protein samples containing DAF-MCP probed with monoclonal antibodies raised against DAF and MCP.

A sample containing DAF-MCP was separated by 10% SDE PAGE and analyzed by Western blot using a monoclonal antibody raised against MCP (GB24) or DAF (IA 10), as shown in FIG. 15. The expressed DAF-MCP protein was recognized by GB 24 as expected.

Figure 16:
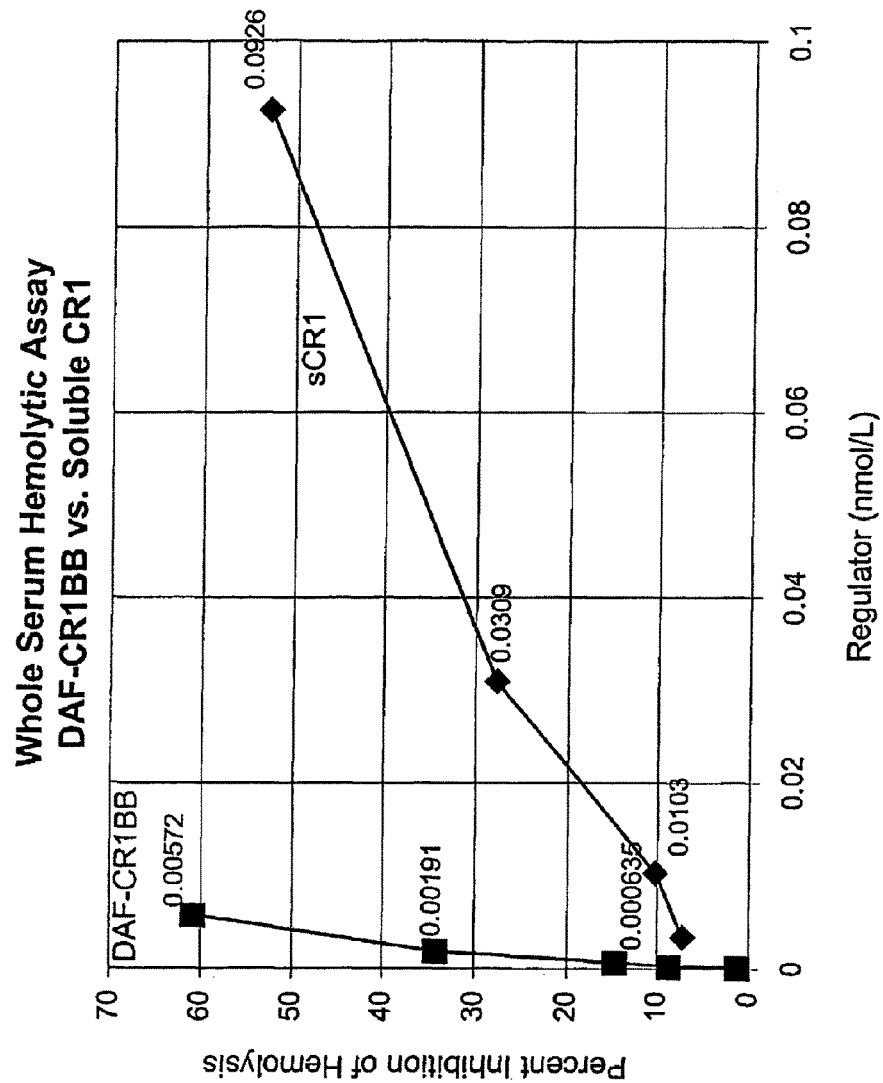
FIG. 16 is a graph showing the percent inhibition of hemolysis of DAF-CR1BB and sCR1 in a whole serum assay.
Figure 17:
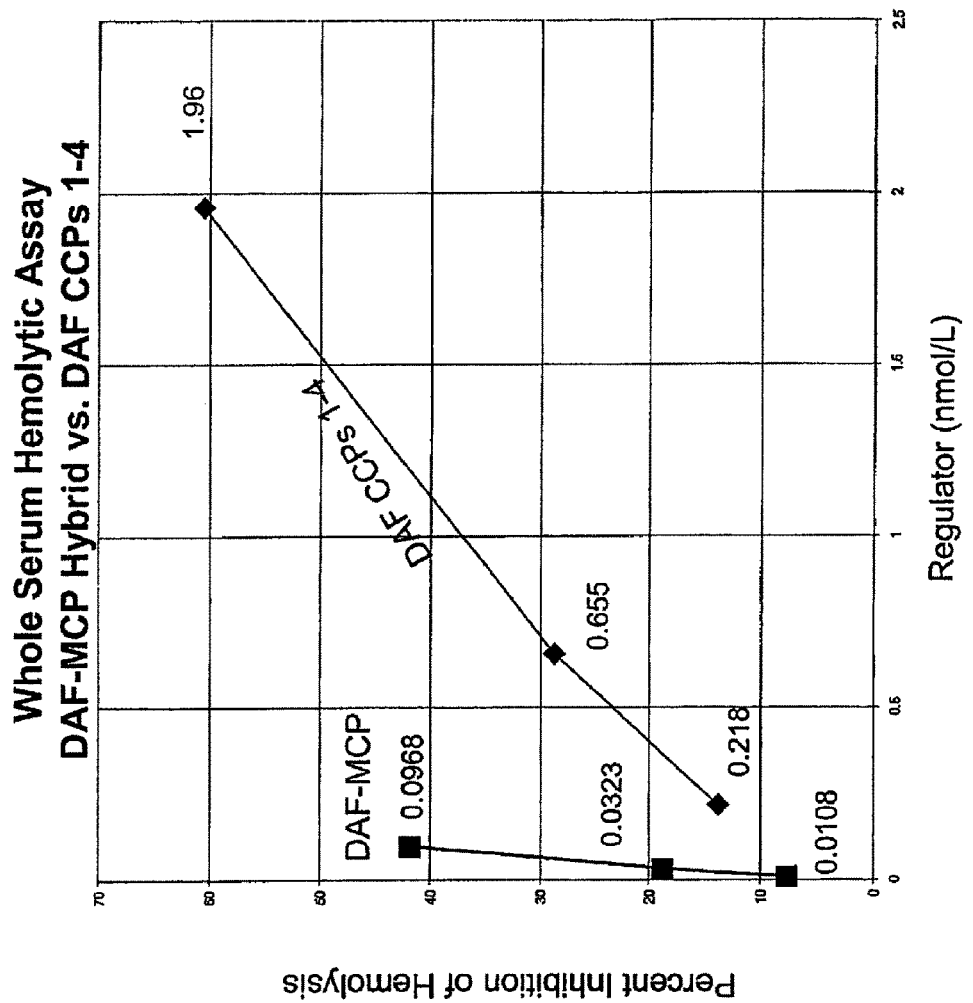
FIG. 17 is a graph showing the percent inhibition of hemolysis of DAF-MCP and DAF in a whole serum assay.

Whole serum hemolytic assays were used to test the ability of the hybrid proteins to inhibit complement activity. FIG. 16 shows the percent inhibition of hemolysis of DAF-CR1BB and SCR1 control versus the concentration of the protein tested. 20-fold more SCR1 is required to achieve 50% inhibition than DAF-CR1BB. FIG. 17 shows the percent inhibition of hemolysis of DAF-MCP and DAF control versus the concentration of the protein tested. To achieve 25 percent inhibition, DAF requires more than 10 fold greater concentration than DAF-MCP.

Figure 18A:
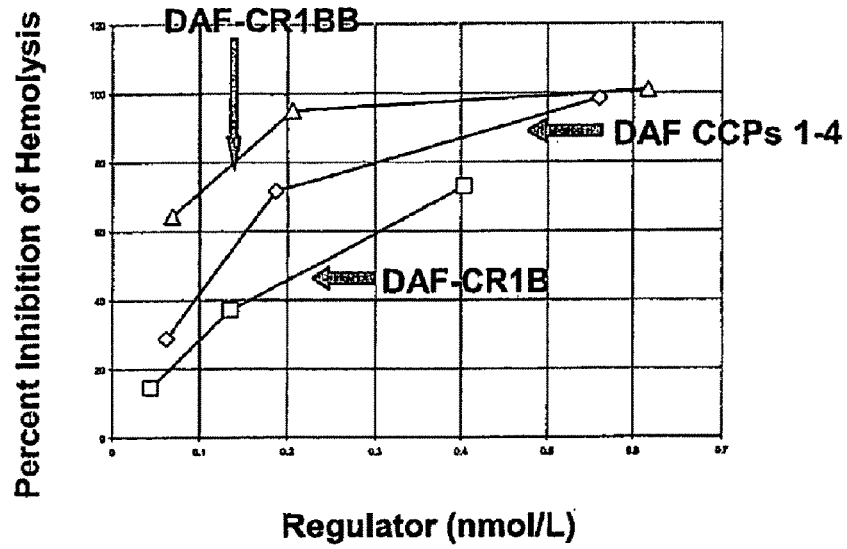
FIGS. 18A and 18B are graphs showing the percent inhibition of hemolysis of the hybrid proteins in a classical pathway C3 convertase assay.
Figure 18B:
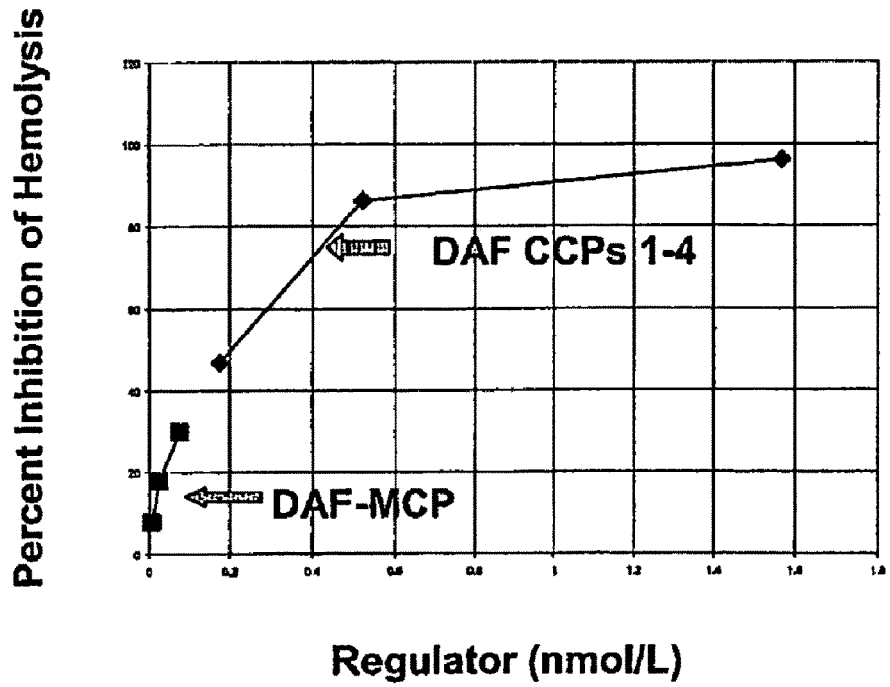

The results of classical pathway C3 convertase hemolytic assays, using the hybrid proteins of the present invention are shown in FIGS. 18 A and B, which are graphs showing the percent inhibition of hemolysis versus the concentration of proteins tested. Again, the hybrid protein containing a functional unit of DAF and two functional units of CR1 exhibited greater inhibition of hemolysis than protein containing only DAF CCPs 1-4.

Figure 19:
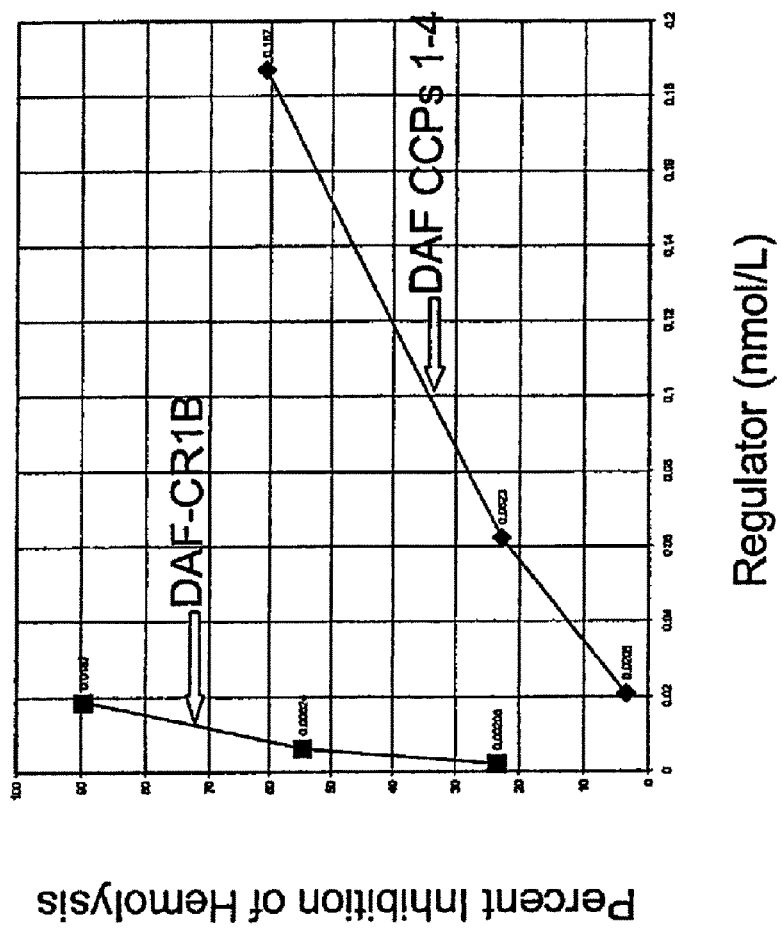
FIG. 19 is a graph showing the percent inhibition of hemolysis of DAF CR1B and DAF in a classical pathway C5 convertase assay.
Figure 20:
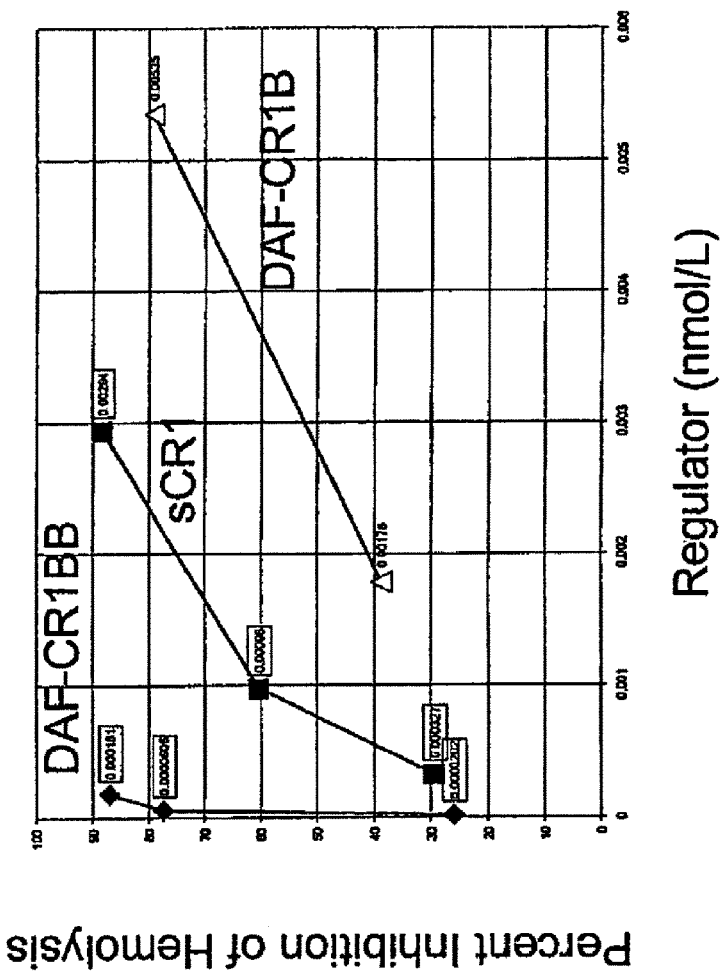
FIG. 20 is a graph showing the percent inhibition of hemolysis of DAF CR1BB, sCR1 and DAF-CR1B in a classical pathway C5 convertase assay.

The ability of the hybrid proteins to inhibit hemolysis in a classical pathway C5 convertase assay is shown in the graphs of FIGS. 19 and 20. In FIG. 19, DAF-CR1B provides superior inhibition of hemolysis compared to DAF. In FIG. 20, DAF-CR1BB shows 19-fold greater inhibition of hemolysis than CR1 and 71-fold greater inhibition than DAF-CR1B.

Figure 21:
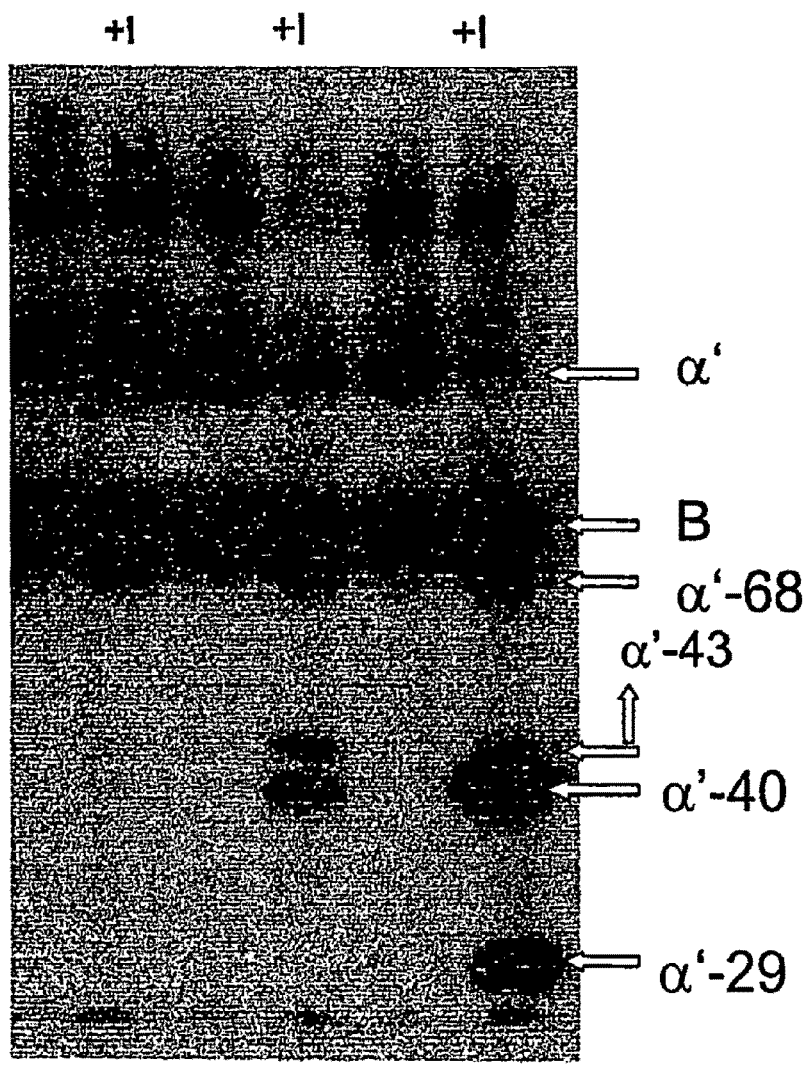
FIG. 21 is a Western blot of supernatants of cells expressing the hybrid proteins of DAF-MCP or DAF-CR1BB with and without factor I in a cofactor assay.
Figure 22:
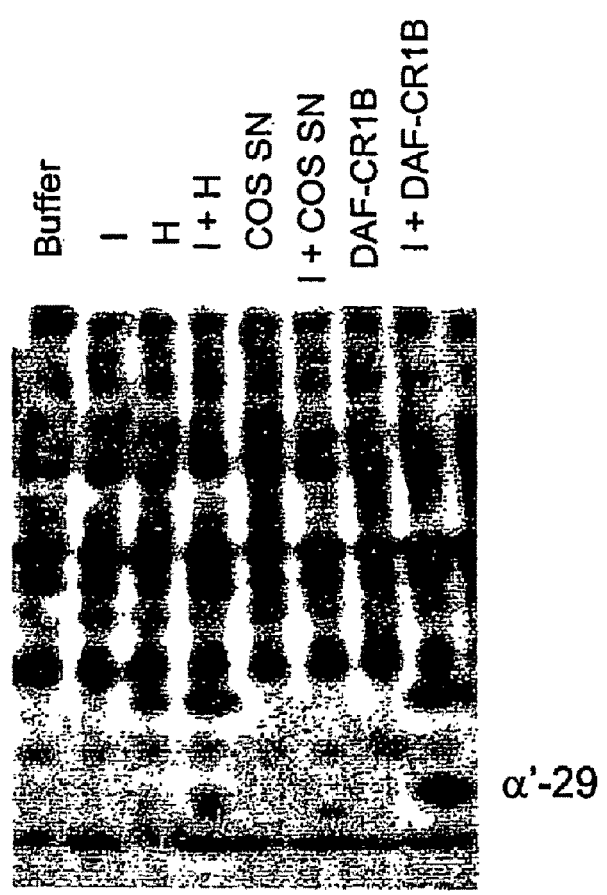
FIG. 22 is a Western blot of supernatants of cells expressing the hybrid proteins of DAF-Cr1B with and without factor I in a cofactor assay.

The ability of DAF-MCP and DAF-CR1BB to act as cofactors for factor I is shown in FIG. 21. Samples were separated by SDS-PAGE, and developed with an anti-human C3 polyclonal antibody. Supernatants from COS cells were analyzed neat, with DAF-MCP or with DAF-CR1BB. Each of the samples was assayed with or without factor I (+I). Supernatants with factor I and either DAF-MCP or DAF-CR1BB both exhibited 43 and 40 kDa bands corresponding to formation of iC3b and C3c, respectively. The DAF-CR1BB sample additionally displayed a 29 kDa band corresponding to formation of C3c. A similar result is shown in FIG. 22, where DAF-CR1B acts as cofactor for factor I as shown by the appearance of a band at 29 kDa.

Based upon the foregoing disclosure, it should be apparent that the present invention will carry out the aspects set forth above. It is therefore, to be understood that any variations evident fall within the scope of the invention and thus, the selection of specific component elements can be determined without departing from the spirit of the invention herein disclosed and described.

We claim:

1. A hybrid protein consisting of:

a functional unit of a complement regulatory protein, the functional unit consisting of Complement Control Protein repeats (CCPs) 2, 3 and 4 of human DAF or CCPs 1, 2, 3, and 4 of human DAF, the functional unit having decay accelerating activity against classical pathway and alternative pathway convertase, a targeting moiety that enhances binding of the hybrid protein to an animal tissue, wherein the targeting moiety is a lipid tail that targets a cell membrane bilayer, and a polypeptide spacer sequence is attached to and separates the functional unit and the targeting moiety, wherein the spacer sequence does not exhibit complement regulating properties and comprises at least 200 consecutive amino acids of SEQ ID NO: 3 CCPs 4-7 of CR1 (residues 239 to 496 of SEQ ID NO: 3) or CCPs 11-14 of CR1 (residues 689 to 874 through of SEQ ID NO: 3).

2. The protein of claim 1, the functional unit consisting of CCPs 1, 2, 3, and 4 of human DAF.

3. A hybrid protein consisting of:

a functional unit that consists of Complement Control Protein repeats (CCPs) 1, 2, 3 and 4 of human DAF and having decay accelerating activity against classical pathway and alternative pathway covertase, a targeting moiety that enhances binding of the hybrid protein to an animal tissue, wherein the targeting moiety is a lipid tail that targets a cell membrane bilayer, and a polypeptide spacer sequence that comprises at least 200 consecutive amino acids of human CR1, the spacer sequence is attached to and separates the functional unit and the targeting moiety, the spacer sequence does not exhibit complement regulating properties.

4. The protein of claim 3, wherein the spacer is selected from the group consisting of CCPs 4-7 of CR1 and CCPs 11-14 of CR1.

* * * * *

SEQUENCE LISTING

<160> NUMBER OF SEQ ID NOS: 35

<210> SEQ ID NO 1
<211> LENGTH: 381
<212> TYPE: PRT
<213> ORGANISM: Homo sapiens

```
<400> SEQUENCE: 1

Met Thr Val Ala Arg Pro Ser Val Pro Ala Leu Pro Leu Leu Gly
 1               5                  10                  15

Glu Leu Pro Arg Leu Leu Leu Val Leu Leu Cys Leu Pro Ala Val
                20                  25                  30

Trp Gly Asp Cys Gly Leu Pro Pro Asp Val Pro Asn Ala Gln Pro Ala
            35                  40                  45

Leu Glu Gly Arg Thr Ser Phe Pro Glu Asp Thr Val Ile Thr Tyr Lys
 50                      55                      60

Cys Glu Glu Ser Phe Val Lys Ile Pro Gly Glu Lys Asp Ser Val Ile
 65                  70                  75                  80

Cys Leu Lys Gly Ser Gln Trp Ser Asp Ile Glu Glu Phe Cys Asn Arg
                85                      90                  95

Ser Cys Glu Val Pro Thr Arg Leu Asn Ser Ala Ser Leu Lys Gln Pro
                100                 105                 110

Tyr Ile Thr Gln Asn Tyr Phe Pro Val Gly Thr Val Val Glu Tyr Glu
            115                 120                 125

Cys Arg Pro Gly Tyr Arg Arg Glu Pro Ser Leu Ser Pro Lys Leu Thr
130                 135                 140

Cys Leu Gln Asn Leu Lys Trp Ser Thr Ala Val Glu Phe Cys Lys Lys
145                 150                 155                 160

Lys Ser Cys Pro Asn Pro Gly Glu Ile Arg Asn Gly Gln Ile Asp Val
                165                 170                 175

Pro Gly Gly Ile Leu Phe Gly Ala Thr Ile Ser Phe Ser Cys Asn Thr
            180                 185                 190

Gly Tyr Lys Leu Phe Gly Ser Thr Ser Ser Phe Cys Leu Ile Ser Gly
            195                 200                 205

Ser Ser Val Gln Trp Ser Asp Pro Leu Pro Glu Cys Arg Glu Ile Tyr
210                 215                 220

Cys Pro Ala Pro Pro Gln Ile Asp Asn Gly Ile Ile Gln Gly Glu Arg
225                 230                 235                 240

Asp His Tyr Gly Tyr Arg Gln Ser Val Thr Tyr Ala Cys Asn Lys Gly
                245                 250                 255

Phe Thr Met Ile Gly Glu His Ser Ile Tyr Cys Thr Val Asn Asn Asp
            260                 265                 270

Glu Gly Glu Trp Ser Gly Pro Pro Pro Glu Cys Arg Gly Lys Ser Leu
            275                 280                 285

Thr Ser Lys Val Pro Pro Thr Val Gln Lys Pro Thr Thr Val Asn Val
290                 295                 300

Pro Thr Thr Glu Val Ser Pro Thr Ser Gln Lys Thr Thr Thr Lys Thr
305                 310                 315                 320

Thr Thr Pro Asn Ala Gln Ala Thr Arg Ser Thr Pro Val Ser Arg Thr
                325                 330                 335

Thr Lys His Phe His Glu Thr Thr Pro Asn Lys Gly Ser Gly Thr Thr
            340                 345                 350

Ser Gly Thr Thr Arg Leu Leu Ser Gly His Thr Cys Phe Thr Leu Thr
            355                 360                 365

Gly Leu Leu Gly Thr Leu Val Thr Met Gly Leu Leu Thr
370                 375                 380

<210> SEQ ID NO 2
<211> LENGTH: 2102
<212> TYPE: DNA
<213> ORGANISM: Homo sapiens
```

<400> SEQUENCE: 2

```
ccgctgggcg tagctgcgac tcggcggagt cccggcggcg cgtccttgtt ctaacccggc    60
gcgccatgac cgtcgcgcgg ccgagcgtgc ccgcggcgct gcccctcctc ggggagctgc   120
cccggctgct gctgctggtg ctgttgtgcc tgccggccgt gtggggtgac tgtggccttc   180
ccccagatgt acctaatgcc cagccagctt tggaaggccg tacaagtttt cccgaggata   240
ctgtaataac gtacaaatgt gaagaaagct ttgtgaaaat tcctggcgag aaggactcag   300
tgatctgcct taagggcagt caatggtcag atattgaaga gttctgcaat cgtagctgcg   360
aggtgccaac aaggctaaat tctgcatccc tcaaacagcc ttatatcact cagaattatt   420
ttccagtcgg tactgttgtg aatatgagt gccgtccagg ttacagaaga gaaccttctc   480
tatcaccaaa actaacttgc cttcagaatt taaaatggtc cacagcagtc gaattttgta   540
aaaagaaatc atgccctaat ccgggagaaa tacgaaatgg tcagattgat gtaccaggtg   600
gcatattatt tggtgcaacc atctccttct catgtaacac agggtacaaa ttatttggct   660
cgacttctag tttttgtctt atttcaggca gctctgtcca gtggagtgac ccgttgccag   720
agtgcagaga aatttattgt ccagcaccac cacaaattga caatggaata attcaagggg   780
aacgtgacca ttatggatat agacagtctg taacgtatgc atgtaataaa ggattcacca   840
tgattggaga gcactctatt tattgtactg tgaataatga tgaaggagag tggagtggcc   900
caccacctga atgcagagga aaatctctaa cttccaaggt cccaccaaca gttcagaaac   960
ctaccacagt aaatgttcca actacagaag tctcaccaac ttctcagaaa accaccacaa  1020
aaaccaccac accaaatgct caagcaacac ggagtacacc tgtttccagg acaaccaagc  1080
attttcatga acaaccccca aataaggaa gtggaaccac ttcaggtact acccgtcttc  1140
tatctgggca cacgtgtttc acgttgcagg gtttgcttgg gacgctagta accatgggct  1200
tgctgactta gccaaagaag agttaagaag aaaatacaca caagtataca gactgttcct  1260
agtttcttag acttatctgc atattggata aaataaatgc aattgtgctc ttcatttagg  1320
atgctttcat tgtctttaag atgtgttagg aatgtcaaca gagcaaggag aaaaaaggca  1380
gtcctggaat cacattctta gcacacctac acctcttgaa aatagaacaa cttgcagaat  1440
tgagagtgat tccttttccta aaagtgtaag aaagcataga gatttgttcg tatttagaat  1500
gggatcacga ggaaaagaga aggaaagtga tttttttcca caagatctgt aatgttattt  1560
ccacttataa aggaaataaa aaatgaaaaa cattatttgg atatcaaaag caaataaaaa  1620
cccaattcag tctcttctaa gcaaaattgc taaagagaga tgaaccacat tataaagtaa  1680
tctttggctg taaggcattt tcatctttcc ttcgggttgg caaaatattt taaaggtaaa  1740
acatgctggt gaaccagggg tgttgatggt gataagggag gaatatagaa tgaaagactg  1800
aatcttcctt tgttgcacaa atagagtttg gaaaagcct gtgaaaggtg tcttctttga  1860
cttaatgtct ttaaaagtat ccagagatac tacaatatta acataagaaa agattatata  1920
ttatttctga atcgagatgt ccatagtcaa atttgtaaat cttattcttt tgtaaatattt  1980
atttatattt atttatgaca gtgaacattc tgattttaca tgtaaaacaa gaaaagttga  2040
agaagatatg tgaagaaaaa tgtattttc ctaaatagaa ataaatgatc ccattttttg  2100
gt                                                                 2102
```

<210> SEQ ID NO 3
<211> LENGTH: 2044
<212> TYPE: PRT
<213> ORGANISM: Homo sapiens

<400> SEQUENCE: 3

```
Met Cys Leu Gly Arg Met Gly Ala Ser Ser Pro Arg Ser Pro Glu Pro
  1               5                  10                  15
Val Gly Pro Pro Ala Pro Gly Leu Pro Phe Cys Cys Gly Gly Ser Leu
             20                  25                  30
Leu Ala Val Val Leu Leu Ala Leu Pro Val Ala Trp Gly Gln Cys
         35                  40                  45
Asn Ala Pro Glu Trp Leu Pro Phe Ala Arg Pro Thr Asn Leu Thr Asp
 50                  55                  60
Glu Phe Glu Phe Pro Ile Gly Thr Tyr Leu Asn Tyr Glu Cys Arg Pro
 65                  70                  75                  80
Gly Tyr Ser Gly Arg Pro Phe Ser Ile Ile Cys Leu Lys Asn Ser Val
                 85                  90                  95
Trp Thr Gly Ala Lys Asp Arg Cys Arg Arg Lys Ser Cys Arg Asn Pro
             100                 105                 110
Pro Asp Pro Val Asn Gly Met Val His Val Ile Lys Gly Ile Gln Phe
             115                 120                 125
Gly Ser Gln Ile Lys Tyr Ser Cys Thr Lys Gly Tyr Arg Leu Ile Gly
         130                 135                 140
Ser Ser Ser Ala Thr Cys Ile Ile Ser Gly Asp Thr Val Ile Trp Asp
145                 150                 155                 160
Asn Glu Thr Pro Ile Cys Asp Arg Ile Pro Cys Gly Leu Pro Pro Thr
                 165                 170                 175
Ile Thr Asn Gly Asp Phe Ile Ser Thr Asn Arg Glu Asn Phe His Tyr
             180                 185                 190
Gly Ser Val Val Thr Tyr Arg Cys Asn Pro Gly Ser Gly Gly Arg Lys
         195                 200                 205
Val Phe Glu Leu Val Gly Glu Pro Ser Ile Tyr Cys Thr Ser Asn Asp
210                 215                 220
Asp Gln Val Gly Ile Trp Ser Gly Pro Ala Pro Gln Cys Ile Ile Pro
225                 230                 235                 240
Asn Lys Cys Thr Pro Pro Asn Val Glu Asn Gly Ile Leu Val Ser Asp
                 245                 250                 255
Asn Arg Ser Leu Phe Ser Leu Asn Glu Val Val Glu Phe Arg Cys Gln
             260                 265                 270
Pro Gly Phe Val Met Lys Gly Pro Arg Arg Val Lys Cys Gln Ala Leu
         275                 280                 285
Asn Lys Trp Glu Pro Glu Leu Pro Ser Cys Ser Arg Val Cys Gln Pro
290                 295                 300
Pro Pro Asp Val Leu His Ala Glu Arg Thr Gln Arg Asp Lys Asp Asn
305                 310                 315                 320
Phe Ser Pro Gly Gln Glu Val Phe Tyr Ser Cys Glu Pro Gly Tyr Asp
                 325                 330                 335
Leu Arg Gly Ala Ala Ser Met Arg Cys Thr Pro Gln Gly Asp Trp Ser
             340                 345                 350
Pro Ala Ala Pro Thr Cys Glu Val Lys Ser Cys Asp Asp Phe Met Gly
         355                 360                 365
Gln Leu Leu Asn Gly Arg Val Leu Phe Pro Val Asn Leu Gln Leu Gly
     370                 375                 380
Ala Lys Val Asp Phe Val Cys Asp Glu Gly Phe Gln Leu Lys Gly Ser
385                 390                 395                 400
Ser Ala Ser Tyr Cys Val Leu Ala Gly Met Glu Ser Leu Trp Asn Ser
                 405                 410                 415
```

-continued

Ser Val Pro Val Cys Glu Gln Ile Phe Cys Pro Ser Pro Val Ile
        420                 425             430

Pro Asn Gly Arg His Thr Gly Lys Pro Leu Glu Val Phe Pro Phe Gly
        435                 440             445

Lys Ala Val Asn Tyr Thr Cys Asp Pro His Pro Asp Arg Gly Thr Ser
    450                 455                 460

Phe Asp Leu Ile Gly Glu Ser Thr Ile Arg Cys Thr Ser Asp Pro Gln
465             470                 475                 480

Gly Asn Gly Val Trp Ser Ser Pro Ala Pro Arg Cys Gly Ile Leu Gly
                485                 490                 495

His Cys Gln Ala Pro Asp His Phe Leu Phe Ala Lys Leu Lys Thr Gln
            500                 505                 510

Thr Asn Ala Ser Asp Phe Pro Ile Gly Thr Ser Leu Lys Tyr Glu Cys
            515                 520                 525

Arg Pro Glu Tyr Tyr Gly Arg Pro Phe Ser Ile Thr Cys Leu Asp Asn
        530                 535                 540

Leu Val Trp Ser Ser Pro Lys Asp Val Cys Lys Arg Lys Ser Cys Lys
545                 550                 555                 560

Thr Pro Pro Asp Pro Val Asn Gly Met Val His Val Ile Thr Asp Ile
                565                 570                 575

Gln Val Gly Ser Arg Ile Asn Tyr Ser Cys Thr Thr Gly His Arg Leu
            580                 585                 590

Ile Gly His Ser Ser Ala Glu Cys Ile Leu Ser Gly Asn Ala Ala His
        595                 600                 605

Trp Ser Thr Lys Pro Pro Ile Cys Gln Arg Ile Pro Cys Gly Leu Pro
        610                 615                 620

Pro Thr Ile Ala Asn Gly Asp Phe Ile Ser Thr Asn Arg Glu Asn Phe
625             630                 635                 640

His Tyr Gly Ser Val Val Thr Tyr Arg Cys Asn Pro Gly Ser Gly Gly
                645                 650                 655

Arg Lys Val Phe Glu Leu Val Gly Glu Pro Ser Ile Tyr Cys Thr Ser
            660                 665                 670

Asn Asp Asp Gln Val Gly Ile Trp Ser Gly Pro Ala Pro Gln Cys Ile
            675                 680                 685

Ile Pro Asn Lys Cys Thr Pro Pro Asn Val Glu Asn Gly Ile Leu Val
        690                 695                 700

Ser Asp Asn Arg Ser Leu Phe Ser Leu Asn Glu Val Val Glu Phe Arg
705             710                 715                 720

Cys Gln Pro Gly Phe Val Met Lys Gly Pro Arg Arg Val Lys Cys Gln
                725                 730                 735

Ala Leu Asn Lys Trp Glu Pro Glu Leu Pro Ser Cys Ser Arg Val Cys
            740                 745                 750

Gln Pro Pro Pro Asp Val Leu His Ala Glu Arg Thr Gln Arg Asp Lys
        755                 760                 765

Asp Asn Phe Ser Pro Gly Gln Glu Val Phe Tyr Ser Cys Glu Pro Gly
        770                 775                 780

Tyr Asp Leu Arg Gly Ala Ala Ser Met Arg Cys Thr Pro Gln Gly Asp
785             790                 795                 800

Trp Ser Pro Ala Ala Pro Thr Cys Glu Val Lys Ser Cys Asp Asp Phe
                805                 810                 815

Met Gly Gln Leu Leu Asn Gly Arg Val Leu Phe Pro Val Asn Leu Gln
            820                 825                 830

-continued

```
Leu Gly Ala Lys Val Asp Phe Val Cys Asp Glu Gly Phe Gln Leu Lys
            835                 840                 845

Gly Ser Ser Ala Ser Tyr Cys Val Leu Ala Gly Met Glu Ser Leu Trp
850                 855                 860

Asn Ser Ser Val Pro Val Cys Glu Gln Ile Phe Cys Pro Ser Pro Pro
865                 870                 875                 880

Val Ile Pro Asn Gly Arg His Thr Gly Lys Pro Leu Glu Val Phe Pro
                885                 890                 895

Phe Gly Lys Ala Val Asn Tyr Thr Cys Asp Pro His Pro Asp Arg Gly
            900                 905                 910

Thr Ser Phe Asp Leu Ile Gly Glu Ser Thr Ile Arg Cys Thr Ser Asp
        915                 920                 925

Pro Gln Gly Asn Gly Val Trp Ser Ser Pro Ala Pro Arg Cys Gly Ile
    930                 935                 940

Leu Gly His Cys Gln Ala Pro Asp His Phe Leu Phe Ala Lys Leu Lys
945                 950                 955                 960

Thr Gln Thr Asn Ala Ser Asp Phe Pro Ile Gly Thr Ser Leu Lys Tyr
                965                 970                 975

Glu Cys Arg Pro Glu Tyr Tyr Gly Arg Pro Phe Ser Ile Thr Cys Leu
            980                 985                 990

Asp Asn Leu Val Trp Ser Ser Pro Lys Asp Val Cys Lys Arg Lys Ser
        995                 1000                1005

Cys Lys Thr Pro Pro Asp Pro Val Asn Gly Met Val His Val Ile Thr
    1010                1015                1020

Asp Ile Gln Val Gly Ser Arg Ile Asn Tyr Ser Cys Thr Thr Gly His
1025                1030                1035                1040

Arg Leu Ile Gly His Ser Ser Ala Glu Cys Ile Leu Ser Gly Asn Thr
                1045                1050                1055

Ala His Trp Ser Thr Lys Pro Pro Ile Cys Gln Arg Ile Pro Cys Gly
            1060                1065                1070

Leu Pro Pro Thr Ile Ala Asn Gly Asp Phe Ile Ser Thr Asn Arg Glu
        1075                1080                1085

Asn Phe His Tyr Gly Ser Val Val Thr Tyr Arg Cys Asn Leu Gly Ser
    1090                1095                1100

Arg Gly Arg Lys Val Phe Glu Leu Val Gly Glu Pro Ser Ile Tyr Cys
1105                1110                1115                1120

Thr Ser Asn Asp Asp Gln Val Gly Ile Trp Ser Gly Pro Ala Pro Gln
                1125                1130                1135

Cys Ile Ile Pro Asn Lys Cys Thr Pro Pro Asn Val Glu Asn Gly Ile
            1140                1145                1150

Leu Val Ser Asp Asn Arg Ser Leu Phe Ser Leu Asn Glu Val Val Glu
        1155                1160                1165

Phe Arg Cys Gln Pro Gly Phe Val Met Lys Gly Pro Arg Arg Val Lys
    1170                1175                1180

Cys Gln Ala Leu Asn Lys Trp Glu Pro Glu Leu Pro Ser Cys Ser Arg
1185                1190                1195                1200

Val Cys Gln Pro Pro Pro Glu Ile Leu His Gly Glu His Thr Pro Ser
                1205                1210                1215

His Gln Asp Asn Phe Ser Pro Gly Gln Glu Val Phe Tyr Ser Cys Glu
            1220                1225                1230

Pro Gly Tyr Asp Leu Arg Gly Ala Ala Ser Leu His Cys Thr Pro Gln
        1235                1240                1245

Gly Asp Trp Ser Pro Glu Ala Pro Arg Cys Ala Val Lys Ser Cys Asp
```

```
                1250                1255                1260
Asp Phe Leu Gly Gln Leu Pro His Gly Arg Val Leu Phe Pro Leu Asn
1265                1270                1275                1280
Leu Gln Leu Gly Ala Lys Val Ser Phe Val Cys Asp Glu Gly Phe Arg
                1285                1290                1295
Leu Lys Gly Ser Ser Val Ser His Cys Val Leu Val Gly Met Arg Ser
                1300                1305                1310
Leu Trp Asn Asn Ser Val Pro Val Cys Glu His Ile Phe Cys Pro Asn
                1315                1320                1325
Pro Pro Ala Ile Leu Asn Gly Arg His Thr Gly Thr Pro Ser Gly Asp
                1330                1335                1340
Ile Pro Tyr Gly Lys Glu Ile Ser Tyr Thr Cys Asp Pro His Pro Asp
1345                1350                1355                1360
Arg Gly Met Thr Phe Asn Leu Ile Gly Glu Ser Thr Ile Arg Cys Thr
                1365                1370                1375
Ser Asp Pro His Gly Asn Gly Val Trp Ser Ser Pro Ala Pro Arg Cys
                1380                1385                1390
Glu Leu Ser Val Arg Ala Gly His Cys Lys Thr Pro Glu Gln Phe Pro
                1395                1400                1405
Phe Ala Ser Pro Thr Ile Pro Ile Asn Asp Phe Glu Phe Pro Val Gly
1410                1415                1420
Thr Ser Leu Asn Tyr Glu Cys Arg Pro Gly Tyr Phe Gly Lys Met Phe
1425                1430                1435                1440
Ser Ile Ser Cys Leu Glu Asn Leu Val Trp Ser Ser Val Glu Asp Asn
                1445                1450                1455
Cys Arg Arg Lys Ser Cys Gly Pro Pro Pro Glu Pro Phe Asn Gly Met
                1460                1465                1470
Val His Ile Asn Thr Asp Thr Gln Phe Gly Ser Thr Val Asn Tyr Ser
                1475                1480                1485
Cys Asn Glu Gly Phe Arg Leu Ile Gly Ser Pro Ser Thr Thr Cys Leu
                1490                1495                1500
Val Ser Gly Asn Asn Val Thr Trp Asp Lys Lys Ala Pro Ile Cys Glu
1505                1510                1515                1520
Ile Ile Ser Cys Glu Pro Pro Pro Thr Ile Ser Asn Gly Asp Phe Tyr
                1525                1530                1535
Ser Asn Asn Arg Thr Ser Phe His Asn Gly Thr Val Val Thr Tyr Gln
                1540                1545                1550
Cys His Thr Gly Pro Asp Gly Glu Gln Leu Phe Glu Leu Val Gly Glu
                1555                1560                1565
Arg Ser Ile Tyr Cys Thr Ser Lys Asp Asp Gln Val Gly Val Trp Ser
                1570                1575                1580
Ser Pro Pro Pro Arg Cys Ile Ser Thr Asn Lys Cys Thr Ala Pro Glu
1585                1590                1595                1600
Val Glu Asn Ala Ile Arg Val Pro Gly Asn Arg Ser Phe Phe Ser Leu
                1605                1610                1615
Thr Glu Ile Ile Arg Phe Arg Cys Gln Pro Gly Phe Val Met Val Gly
                1620                1625                1630
Ser His Thr Val Gln Cys Gln Thr Asn Gly Arg Trp Gly Pro Lys Leu
                1635                1640                1645
Pro His Cys Ser Arg Val Cys Gln Pro Pro Glu Ile Leu His Gly
                1650                1655                1660
Glu His Thr Leu Ser His Gln Asp Asn Phe Ser Pro Gly Gln Glu Val
1665                1670                1675                1680
```

Phe Tyr Ser Cys Glu Pro Ser Tyr Asp Leu Arg Gly Ala Ala Ser Leu
            1685                1690                1695

His Cys Thr Pro Gln Gly Asp Trp Ser Pro Glu Ala Pro Arg Cys Thr
        1700                1705                1710

Val Lys Ser Cys Asp Asp Phe Leu Gly Gln Leu Pro His Gly Arg Val
    1715                1720                1725

Leu Leu Pro Leu Asn Leu Gln Leu Gly Ala Lys Val Ser Phe Val Cys
1730                1735                1740

Asp Glu Gly Phe Arg Leu Lys Gly Arg Ser Ala Ser His Cys Val Leu
1745                1750                1755                1760

Ala Gly Met Lys Ala Leu Trp Asn Ser Ser Val Pro Val Cys Glu Gln
            1765                1770                1775

Ile Phe Cys Pro Asn Pro Pro Ala Ile Leu Asn Gly Arg His Thr Gly
        1780                1785                1790

Thr Pro Phe Gly Asp Ile Pro Tyr Gly Lys Glu Ile Ser Tyr Ala Cys
    1795                1800                1805

Asp Thr His Pro Asp Arg Gly Met Thr Phe Asn Leu Ile Gly Glu Ser
1810                1815                1820

Ser Ile Arg Cys Thr Ser Asp Pro Gln Gly Asn Gly Val Trp Ser Ser
1825                1830                1835                1840

Pro Ala Pro Arg Cys Glu Leu Ser Val Pro Ala Ala Cys Pro His Pro
            1845                1850                1855

Pro Lys Ile Gln Asn Gly His Tyr Ile Gly Gly His Val Ser Leu Tyr
        1860                1865                1870

Leu Pro Gly Met Thr Ile Ser Tyr Thr Cys Asp Pro Gly Tyr Leu Leu
    1875                1880                1885

Val Gly Lys Gly Phe Ile Phe Cys Thr Asp Gln Gly Ile Trp Ser Gln
1890                1895                1900

Leu Asp His Tyr Cys Lys Glu Val Asn Cys Ser Phe Pro Leu Phe Met
1905                1910                1915                1920

Asn Gly Ile Ser Lys Glu Leu Glu Met Lys Lys Val Tyr His Tyr Gly
            1925                1930                1935

Asp Tyr Val Thr Leu Lys Cys Glu Asp Gly Tyr Thr Leu Glu Gly Ser
        1940                1945                1950

Pro Trp Ser Gln Cys Gln Ala Asp Asp Arg Trp Asp Pro Pro Leu Ala
    1955                1960                1965

Lys Cys Thr Ser Arg Ala His Asp Ala Leu Ile Val Gly Thr Leu Ser
    1970                1975                1980

Gly Thr Ile Phe Phe Ile Leu Leu Ile Ile Phe Leu Ser Trp Ile Ile
1985                1990                1995                2000

Leu Lys His Arg Lys Gly Asn Asn Ala His Glu Asn Pro Lys Glu Val
            2005                2010                2015

Ala Ile His Leu His Ser Gln Gly Gly Ser Ser Val His Pro Arg Thr
        2020                2025                2030

Leu Gln Thr Asn Glu Glu Asn Ser Arg Val Leu Pro
    2035                2040

<210> SEQ ID NO 4
<211> LENGTH: 6951
<212> TYPE: DNA
<213> ORGANISM: Homo sapiens

<400> SEQUENCE: 4
cgtggtttgt agatgtgctt ggggagaatg ggggcctctt ctccaagaag cccggagcct      60

```
gtcgggccgc cggcgcccgg tctccccttc tgctgcggag gatccctgct ggcggttgtg    120
gtgctgcttg cgctgccggt ggcctggggt caatgcaatg ccccagaatg gcttccattt    180
gccaggccta ccaacctaac tgatgagttt gagtttccca ttgggacata tctgaactat    240
gaatgccgcc ctggttattc cggaagaccg ttttctatca tctgcctaaa aaactcagtc    300
tggactggtg ctaaggacag gtgcagacgt aaatcatgtc gtaatcctcc agatcctgtg    360
aatggcatgg tgcatgtgat caaaggcatc cagttcggat cccaaattaa atattcttgt    420
actaaaggat accgactcat tggttcctcg tctgccacat gcatcatctc aggtgatact    480
gtcatttggg ataatgaaac acctatttgt gacagaattc cttgtgggct acccccccacc   540 atcaccaatg gagatttcat tagcaccaac agagagaatt ttcactatgg atcagtggtg    600
acctaccgct gcaatcctgg aagcggaggg agaaaggtgt ttgagcttgt gggtgagccc    660
tccatatact gcaccagcaa tgacgatcaa gtgggcatct ggagcggccc cgcccctcag    720
tgcattatac ctaacaaatg cacgcctcca aatgtggaaa atggaatatt ggtatctgac    780
aacagaagct tattttcctt aaatgaagtt gtggagttta ggtgtcagcc tggctttgtc    840
atgaaaggac cccgccgtgt gaagtgccag gccctgaaca atgggagcc ggagctacca    900 agctgctcca gggtatgtca gccacctcca gatgtcctgc atgctgagcg tacccaaagg    960
gacaaggaca cttttcacc tgggcaggaa gtgttctaca gctgtgagcc cggctacgac   1020
ctcagagggg ctgcgtctat gcgctgcaca ccccagggag actggagccc tgcagccccc   1080
acatgtgaag tgaaatcctg tgatgacttc atggggccaac ttcttaatgg ccgtgtgcta   1140
tttccagtaa atctccagct tggagcaaaa gtggattttg tttgtgatga aggatttcaa   1200
ttaaaaggca gctctgctag ttactgtgtc ttggctggaa tggaaagcct ttggaatagc   1260
agtgttccag tgtgtgaaca aatcttttgt ccaagtcctc cagttattcc taatgggaga   1320
cacacaggaa aacctctgga agtctttccc tttggaaaag cagtaaatta cacatgcgac   1380
ccccacccag acagagggac gagcttcgac ctcattggag agagcaccat ccgctgcaca   1440
agtgaccctc aagggaatgg ggtttggagc agccctgccc ctcgctgtgg aattctgggt   1500
cactgtcaag ccccagatca ttttctgttt gccaagttga aaacccaaac caatgcatct   1560
gactttccca ttgggacatc tttaaagtac gaatgccgtc ctgagtacta cgggaggcca   1620
ttctctatca catgtctaga taacctggtc tggtcaagtc ccaaagatgt ctgtaaacgt   1680
aaatcatgta aaactcctcc agatccagtg aatggcatgg tgcatgtgat cacagacatc   1740
caggttggat ccagaatcaa ctattcttgt actacagggc accgactcat tggtcactca   1800
tctgctgaat gtatcctctc gggcaatgct gcccattgga gcacgaagcc gccaatttgt   1860
caacgaattc cttgtgggct accccccacc atcgccaatg gagatttcat tagcaccaac   1920
agagagaatt ttcactatgg atcagtggtg acctaccgct gcaatcctgg aagcggaggg   1980
agaaaggtgt ttgagcttgt gggtgagccc tccatatact gcaccagcaa tgacgatcaa   2040
gtgggcatct ggagcggccc ggcccctcag tgcattatac ctaacaaatg cacgcctcca   2100
aatgtggaaa atggaatatt ggtatctgac aacagaagct tattttcctt aaatgaagtt   2160
gtggagttta ggtgtcagcc tggctttgtc atgaaaggac cccgccgtgt gaagtgccag   2220
gccctgaaca atgggagcc ggagctacca agctgctcca gggtatgtca gccacctcca   2280
gatgtcctgc atgctgagcg tacccaaagg gacaaggaca cttttcacc cgggcaggaa   2340 gtgttctaca gctgtgagcc cggctatgac ctcagagggg ctgcgtctat gcgctgcaca   2400
```

-continued

```
ccccagggag actggagccc tgcagccccc acatgtgaag tgaaatcctg tgatgacttc    2460
atgggccaac ttcttaatgg ccgtgtgcta tttccagtaa atctccagct tggagcaaaa    2520
gtggattttg tttgtgatga aggatttcaa ttaaaaggca gctctgctag ttattgtgtc    2580
ttggctggaa tggaaagcct tggaatagc agtgttccag tgtgtgaaca aatcttttgt    2640
ccaagtcctc cagttattcc taatgggaga cacacaggaa aacctctgga agtctttccc    2700
tttggaaaag cagtaaatta cacatgcgac ccccacccag acagagggac gagcttcgac    2760
ctcattggag agagcaccat ccgctgcaca agtgaccctc aagggaatgg ggtttggagc    2820
agccctgccc ctcgctgtgg aattctgggt cactgtcaag ccccagatca ttttctgttt    2880
gccaagttga aacccaaac caatgcatct gactttccca ttgggacatc tttaaagtac    2940
gaatgccgtc ctgagtacta cgggaggcca ttctctatca catgtctaga taacctggtc    3000
tggtcaagtc ccaaagatgt ctgtaaacgt aaatcatgta aaactcctcc agatccagtg    3060
aatggcatgg tgcatgtgat cacagacatc caggttggat ccagaatcaa ctattcttgt    3120
actacagggc accgactcat tggtcactca tctgctgaat gtatcctctc aggcaatact    3180
gcccattgga gcacgaagcc gccaatttgt caacgaattc cttgtgggct accccaacc    3240
atcgccaatg gagatttcat tagcaccaac agagagaatt ttcactatgg atcagtggtg    3300
acctaccgct gcaatcttgg aagcagaggg agaaaggtgt tgagcttgt gggtgagccc    3360
tccatatact gcaccagcaa tgacgatcaa gtgggcatct ggagcggccc cgcccctcag    3420
tgcattatac ctaacaaatg cacgcctcca aatgtggaaa atggaatatt ggtatctgac    3480
aacagaagct tattttcctt aaatgaagtt gtggagttta ggtgtcagcc tggctttgtc    3540
atgaaaggac cccgccgtgt gaagtgccag gccctgaaca atgggagcc agagttacca    3600
agctgctcca gggtgtgtca gccgcctcca gaaatcctgc atggtgagca tacccccaagc    3660
catcaggaca acttttcacc tgggcaggaa gtgttctaca gctgtgagcc tggctatgac    3720
ctcagagggg ctgcgtctct gcactgcaca ccccagggag actggagccc tgaagccccg    3780
agatgtgcag tgaaatcctg tgatgacttc ttgggtcaac tccctcatgg ccgtgtgcta    3840
tttccactta atctccagct tggggcaaag gtgtcctttg tctgtgatga agggtttcgc    3900
ttaaagggca gttccgttag tcattgtgtc ttggttggaa tgagaagcct ttggaataac    3960
agtgttcctg tgtgtgaaca tatcttttgt ccaaatcctc cagctatcct taatgggaga    4020
cacacaggaa ctccctctgg agatattccc tatggaaaag aaatatctta cacatgtgac    4080
ccccacccag acagagggat gaccttcaac ctcattgggg agagcaccat ccgctgcaca    4140
agtgaccctc atgggaatgg ggtttggagc agccctgccc ctcgctgtga actttctgtt    4200
cgtgctggtc actgtaaaac cccagagcag tttccatttg ccagtcctac gatcccaatt    4260
aatgactttg agtttccagt cgggacatct ttgaattatg aatgccgtcc tgggtatttt    4320
gggaaaatgt tctctatctc ctgcctagaa aacttggtct ggtcaagtgt tgaagacaac    4380
tgtagacgaa aatcatgtgg acctccacca gaacccttca atggaatggt gcatataaac    4440
acagatacac agtttggatc aacagttaat tattcttgta atgaagggtt tcgactcatt    4500
ggttccccat ctactacttg tctcgtctca ggcaataatg tcacatggga taagaaggca    4560
cctatttgtg agatcatatc ttgtgagcca cctccaacca tatccaatgg agacttctac    4620
agcaacaata gaacatcttt tcacaatgga acggtggtaa cttaccagtg ccacactgga    4680
ccagatggag aacagctgtt tgagcttgtg ggagaacggt caatatattg caccagcaaa    4740
gatgatcaag ttggtgtttg gagcagccct cccctcggt gtatttctac taataaatgc    4800
```

```
acagctccag aagttgaaaa tgcaattaga gtaccaggaa acaggagttt ctttteectc    4860
actgagatca tcagatttag atgtcagccc gggtttgtca tggtagggtc ccacactgtg    4920
cagtgccaga ccaatggcag atgggggccc aagctgccac actgctccag ggtgtgtcag    4980
ccgcctccag aaatcctgca tggtgagcat accctaagcc atcaggacaa cttttcacct    5040
gggcaggaag tgttctacag ctgtgagccc agctatgacc tcagagggc tgcgtctctg     5100
cactgcacgc cccagggaga ctggagccct gaagcccta gatgtacagt gaaatcctgt     5160
gatgacttcc tgggccaact ccctcatggc cgtgtgctac ttccacttaa tctccagctt    5220
ggggcaaagg tgtcctttgt ttgcgatgaa gggttccgat taaaaggcag gtctgctagt    5280
cattgtgtct tggctggaat gaaagccctt tggaatagca gtgttccagt gtgtgaacaa    5340
atcttttgtc caaatcctcc agctatcctt aatgggagac acacaggaac tccctttgga    5400
gatattccct atggaaaaga aatatcttac gcatgcgaca cccacccaga cagagggatg    5460
accttcaacc tcattgggga gagctccatc cgctgcacaa gtgaccctca agggaatggg    5520
gtttggagca gccctgcccc tcgctgtgaa cttctgttc ctgctgcctg cccacatcca     5580
cccaagatcc aaaacgggca ttacattgga ggacacgtat ctctatatct tcctgggatg    5640
acaatcagct acacttgtga ccccggctac ctgttagtgg gaaagggctt cattttctgt    5700
acagaccagg gaatctggag ccaattggat cattattgca aagaagtaaa ttgtagcttc    5760
ccactgttta tgaatggaat ctcgaaggag ttagaaatga aaaagtata tcactatgga    5820
gattatgtga ctttgaagtg tgaagatggg tatactctgg aaggcagtcc ctggagccag    5880
tgccaggcgg atgacagatg ggaccctcct ctggccaaat gtacctctcg tgcacatgat    5940
gctctcatag ttggcacttt atctggtacg atcttcttta ttttactcat cattttcctc    6000
tcttggataa ttctaaagca cagaaaaggc aataatgcac atgaaaaccc taagaagtg    6060
gctatccatt tacattctca aggaggcagc agcgttcatc cccgaactct gcaaacaaat    6120
gaagaaaata gcagggtcct tccttgacaa agtactatac agctgaagaa catctcgaat    6180
acaattttgg tgggaaagga gccaattgat ttcaacagaa tcagatctga gcttcataaa    6240
gtctttgaag tgacttcaca gagacgcaga catgtgcact tgaagatgct gccccttccc    6300
tggtacctag caaagctcct gcctctttgt gtgcgtcact gtgaaacccc caccettctg    6360
cctcgtgcta aacgcacaca gtatctagtc aggggaaaag actgcattta ggagatagaa    6420
aatagtttgg attacttaaa ggaataaggt gttgcctgga atttctggtt tgtaaggtgg    6480
tcactgttct tttttaaaat atttgtaata tggaatgggc tcagtaagaa gagcttggaa    6540
aatgcagaaa gttatgaaaa ataagtcact tataattatg ctacctactg ataaccactc    6600
ctaatatttt gattcatttt ctgcctatct tctttcacat atgtgttttt ttacatacgt    6660
acttttcccc ccttagtttg tttccttta ttttatagag cagaaccta gtcttttaaa     6720
cagtttagag tgaaatatat gctatatcag tttttacttt ctctagggag aaaaattaat    6780
ttactagaaa ggcatgaaat gatcatggga agagtggtta agactactga agagaaatat    6840
ttggaaaata gatttcgat atcttctttt tttttgagat ggagtctggc tctgtctccc     6900
aggctggagt gcagtggcgt aatctcggct cactgcaacg tccgcctccc g             6951
```

<210> SEQ ID NO 5
<211> LENGTH: 384
<212> TYPE: PRT
<213> ORGANISM: Homo sapiens

<400> SEQUENCE: 5

```
Met Glu Pro Pro Gly Arg Arg Glu Cys Pro Phe Pro Ser Trp Arg Phe
 1               5                  10                  15

Pro Gly Leu Leu Leu Ala Ala Met Val Leu Leu Tyr Ser Phe Ser
            20                  25                  30

Asp Ala Cys Glu Glu Pro Pro Thr Phe Glu Ala Met Glu Leu Ile Gly
            35                  40                  45

Lys Pro Lys Pro Tyr Tyr Glu Ile Gly Glu Arg Val Asp Tyr Lys Cys
 50                  55                  60

Lys Lys Gly Tyr Phe Tyr Ile Pro Pro Leu Ala Thr His Thr Ile Cys
 65                  70                  75                  80

Asp Arg Asn His Thr Trp Leu Pro Val Ser Asp Ala Cys Tyr Arg
                85                  90                  95

Glu Thr Cys Pro Tyr Ile Arg Asp Pro Leu Asn Gly Gln Ala Val Pro
                100                 105                 110

Ala Asn Gly Thr Tyr Glu Phe Gly Tyr Gln Met His Phe Ile Cys Asn
                115                 120                 125

Glu Gly Tyr Tyr Leu Ile Gly Glu Glu Ile Leu Tyr Cys Glu Leu Lys
130                 135                 140

Gly Ser Val Ala Ile Trp Ser Gly Lys Pro Pro Ile Cys Glu Lys Val
145                 150                 155                 160

Leu Cys Thr Pro Pro Lys Ile Lys Asn Gly Lys His Thr Phe Ser
                165                 170                 175

Glu Val Glu Val Phe Glu Tyr Leu Asp Ala Val Thr Tyr Ser Cys Asp
                180                 185                 190

Pro Ala Pro Gly Pro Asp Pro Phe Ser Leu Ile Gly Glu Ser Thr Ile
                195                 200                 205

Tyr Cys Gly Asp Asn Ser Val Trp Ser Arg Ala Ala Pro Glu Cys Lys
210                 215                 220

Val Val Lys Cys Arg Phe Pro Val Val Glu Asn Gly Lys Gln Ile Ser
225                 230                 235                 240

Gly Phe Gly Lys Lys Phe Tyr Tyr Lys Ala Thr Val Met Phe Glu Cys
                245                 250                 255

Asp Lys Gly Phe Tyr Leu Asp Gly Ser Asp Thr Ile Val Cys Asp Ser
                260                 265                 270

Asn Ser Thr Trp Asp Pro Pro Val Pro Lys Cys Leu Lys Val Ser Thr
                275                 280                 285

Ser Ser Thr Thr Lys Ser Pro Ala Ser Ser Ala Ser Gly Pro Arg Pro
                290                 295                 300

Thr Tyr Lys Pro Pro Val Ser Asn Tyr Pro Gly Tyr Pro Lys Pro Glu
305                 310                 315                 320

Glu Gly Ile Leu Asp Ser Leu Asp Val Trp Val Ile Ala Val Ile Val
                325                 330                 335

Ile Ala Ile Val Val Gly Val Ala Val Ile Cys Val Val Pro Tyr Arg
                340                 345                 350

Tyr Leu Gln Arg Arg Lys Lys Lys Gly Lys Ala Asp Gly Gly Ala Glu
                355                 360                 365

Tyr Ala Thr Tyr Gln Thr Lys Ser Thr Thr Pro Ala Glu Gln Arg Gly
370                 375                 380
```

<210> SEQ ID NO 6
<211> LENGTH: 1530
<212> TYPE: DNA
<213> ORGANISM: Homo sapiens

<400> SEQUENCE: 6

```
tctgctttcc tccggagaaa taacagcgtc ttccgcgccg cgcatggagc ctcccggccg    60
ccgcgagtgt cccttttcctt cctggcgctt tcctggggttg cttctggcgg ccatggtgtt   120
gctgctgtac tccttctccg atgcctgtga ggagccacca acatttgaag ctatggagct   180
cattggtaaa ccaaaaccct actatgagat tggtgaacga gtagattata agtgtaaaaa   240
aggatacttc tatataccctc ctcttgccac ccatactatt tgtgatcgga atcatacatg   300
gctacctgtc tcagatgacg cctgttatag agaaacatgt ccatatatac gggatccttt   360
aaatggccaa gcagtccctg caaatgggac ttacgagttt ggttatcaga tgcactttat   420
ttgtaatgag ggttattact taattggtga agaaattcta tattgtgaac ttaaaggatc   480
agtagcaatt tggagcggta agccccccaat atgtgaaaag gttttgtgta caccacctcc   540
aaaaataaaa aatggaaaac acacctttag tgaagtagaa gtatttgagt atcttgatgc   600
agtaacttat agttgtgatc ctgcacctgg accagatcca ttttcactta ttggagagag   660
cacgatttat tgtggtgaca attcagtgtg gagtcgtgct gctccagagt gtaaagtggt   720
caaatgtcga tttccagtag tcgaaaatgg aaaacagata tcaggatttg gaaaaaaatt   780
ttactacaaa gcaacagtta tgtttgaatg cgataagggt ttttacctcg atggcagcga   840
cacaattgtc tgtgacagta acagtacttg ggatccccca gttccaaagt gtcttaaagt   900
gtcgacttct tccactacaa aatctccagc gtccagtgcc tcaggtccta ggcctactta   960
caagcctcca gtctcaaatt atccaggata tcctaaacct gaggaaggaa tacttgacag  1020
tttggatgtt tgggtcattg ctgtgattgt tattgccata gttgttggag ttgcagtaat  1080
ttgtgttgtc ccgtacagat atcttcaaag gaggaagaag aaaggaaag cagatggtgg  1140
agctgaatat gccacttacc agactaaatc aaccactcca gcagagcaga gaggctgaat  1200
agattccaca acctggttgg ccagttcatc ttttgactct attaaaatct tcaatagttg  1260
ttattctgta gtttcactct catgagtgca actgtggctt agctaatatt gcaatgtggc  1320
ttgaatgtag gtagcatcct ttgatgcttc tttgaaactt gtatgaattt gggtatgaac  1380
agattgcctg cttttcccta aataacactt agatttattg gaccagtcag cacagcatgc  1440
ctggttgtat taaagcaggg atatgctgta ttttataaaa ttggcaaaat tagagaaata  1500
tagttcacaa tgaaattata ttttctttgt                                   1530
```

<210> SEQ ID NO 7
<211> LENGTH: 42
<212> TYPE: DNA
<213> ORGANISM: Artificial Sequence
<220> FEATURE:
<223> OTHER INFORMATION: Synthetic primer

<400> SEQUENCE: 7

```
atatacgaat tcagatctat gaccgtcgcg cggccgagcg tg                       42
```

<210> SEQ ID NO 8
<211> LENGTH: 35
<212> TYPE: DNA
<213> ORGANISM: Artificial Sequence
<220> FEATURE:
<223> OTHER INFORMATION: Synthetic primer

<400> SEQUENCE: 8

```
acagtgctcg agcattcagg tggtgggcca ctcca                              35
```

-continued

<210> SEQ ID NO 9
<211> LENGTH: 41
<212> TYPE: DNA
<213> ORGANISM: Artificial Sequence
<220> FEATURE:
<223> OTHER INFORMATION: Synthetic primer

<400> SEQUENCE: 9
atatacctcg agtcctaaca aatgcacgcc tccaaatgtg g        41

<210> SEQ ID NO 10
<211> LENGTH: 34
<212> TYPE: DNA
<213> ORGANISM: Artificial Sequence
<220> FEATURE:
<223> OTHER INFORMATION: Synthetic primer

<400> SEQUENCE: 10
acagtgatgc attggtttgg gttttcaact tggc        34

<210> SEQ ID NO 11
<211> LENGTH: 41
<212> TYPE: DNA
<213> ORGANISM: Artificial Sequence
<220> FEATURE:
<223> OTHER INFORMATION: Synthetic primer

<400> SEQUENCE: 11
atatacatgc atctgacttt cccattggga catctttaaa g        41

<210> SEQ ID NO 12
<211> LENGTH: 57
<212> TYPE: DNA
<213> ORGANISM: Artificial Sequence
<220> FEATURE:
<223> OTHER INFORMATION: Synthetic primer

<400> SEQUENCE: 12
acagtgagat ctttagtgat ggtgatggtg atgaattcca cagcgagggg cagggct        57

<210> SEQ ID NO 13
<211> LENGTH: 996
<212> TYPE: PRT
<213> ORGANISM: Homo sapiens

<400> SEQUENCE: 13

```
Met Thr Val Ala Arg Pro Ser Val Pro Ala Ala Leu Pro Leu Leu Gly
 1               5                  10                  15

Glu Leu Pro Arg Leu Leu Leu Leu Val Leu Leu Cys Leu Pro Ala Val
                20                  25                  30

Trp Gly Asp Cys Gly Leu Pro Pro Asp Val Pro Asn Ala Gln Pro Ala
            35                  40                  45

Leu Glu Gly Arg Thr Ser Phe Pro Glu Asp Thr Val Ile Thr Tyr Lys
        50                  55                  60

Cys Glu Glu Ser Phe Val Lys Ile Pro Gly Glu Lys Asp Ser Val Ile
 65                  70                  75                  80

Cys Leu Lys Gly Ser Gln Trp Ser Asp Ile Glu Glu Phe Cys Asn Arg
                85                  90                  95

Ser Cys Glu Val Pro Thr Arg Leu Asn Ser Ala Ser Leu Lys Gln Pro
            100                 105                 110

Tyr Ile Thr Gln Asn Tyr Phe Pro Val Gly Thr Val Val Glu Tyr Glu
        115                 120                 125
```

```
Cys Arg Pro Gly Tyr Arg Arg Glu Pro Ser Leu Ser Pro Lys Leu Thr
    130             135                 140
Cys Leu Gln Asn Leu Lys Trp Ser Thr Ala Val Glu Phe Cys Lys Lys
145             150                 155                 160
Lys Ser Cys Pro Asn Pro Gly Glu Ile Arg Asn Gly Gln Ile Asp Val
                165                 170                 175
Pro Gly Gly Ile Leu Phe Gly Ala Thr Ile Ser Phe Ser Cys Asn Thr
            180                 185                 190
Gly Tyr Lys Leu Phe Gly Ser Thr Ser Ser Phe Cys Leu Ile Ser Gly
        195                 200                 205
Ser Ser Val Gln Trp Ser Asp Pro Leu Pro Glu Cys Arg Glu Ile Tyr
    210                 215                 220
Cys Pro Ala Pro Pro Gln Ile Asp Asn Gly Ile Ile Gln Gly Glu Arg
225                 230                 235                 240
Asp His Tyr Gly Tyr Arg Gln Ser Val Thr Tyr Ala Cys Asn Lys Gly
                245                 250                 255
Phe Thr Met Ile Gly Glu His Ser Ile Tyr Cys Thr Val Asn Asn Asp
            260                 265                 270
Glu Gly Glu Trp Ser Gly Pro Pro Glu Cys Ser Ser Pro Asn Lys
        275                 280                 285
Cys Thr Pro Pro Asn Val Glu Asn Gly Ile Leu Val Ser Asp Asn Arg
290                 295                 300
Ser Leu Phe Ser Leu Asn Glu Val Val Glu Phe Arg Cys Gln Pro Gly
305                 310                 315                 320
Phe Val Met Lys Gly Pro Arg Arg Val Lys Cys Gln Ala Leu Asn Lys
            325                 330                 335
Trp Glu Pro Glu Leu Pro Ser Cys Ser Arg Val Cys Gln Pro Pro Pro
        340                 345                 350
Asp Val Leu His Ala Glu Arg Thr Gln Arg Asp Lys Asp Asn Phe Ser
    355                 360                 365
Pro Gly Gln Glu Val Phe Tyr Ser Cys Glu Pro Gly Tyr Asp Leu Arg
370                 375                 380
Gly Ala Ala Ser Met Arg Cys Thr Pro Gln Gly Asp Trp Ser Pro Ala
385                 390                 395                 400
Ala Pro Thr Cys Glu Val Lys Ser Cys Asp Asp Phe Met Gly Gln Leu
                405                 410                 415
Leu Asn Gly Arg Val Leu Phe Pro Val Asn Leu Gln Leu Gly Ala Lys
            420                 425                 430
Val Asp Phe Val Cys Asp Glu Gly Phe Gln Leu Lys Gly Ser Ser Ala
        435                 440                 445
Ser Tyr Cys Val Leu Ala Gly Met Glu Ser Leu Trp Asn Ser Ser Val
    450                 455                 460
Pro Val Cys Glu Gln Ile Phe Cys Pro Ser Pro Val Ile Pro Asn
465                 470                 475                 480
Gly Arg His Thr Gly Lys Pro Leu Glu Val Phe Pro Phe Gly Lys Ala
                485                 490                 495
Val Asn Tyr Thr Cys Asp Pro His Pro Asp Arg Gly Thr Ser Phe Asp
            500                 505                 510
Leu Ile Gly Glu Ser Thr Ile Arg Cys Thr Ser Asp Pro Gln Gly Asn
        515                 520                 525
Gly Val Trp Ser Ser Pro Ala Pro Arg Cys Gly Ile Leu Gly His Cys
530                 535                 540
```

-continued

Gln Ala Pro Asp His Phe Leu Phe Ala Lys Leu Lys Thr Gln Thr Asn
545                 550                 555                 560

Ala Ser Asp Phe Pro Ile Gly Thr Ser Leu Lys Tyr Glu Cys Arg Pro
            565                 570                 575

Glu Tyr Tyr Gly Arg Pro Phe Ser Ile Thr Cys Leu Asp Asn Leu Val
        580                 585                 590

Trp Ser Ser Pro Lys Asp Val Cys Lys Arg Lys Ser Cys Lys Thr Pro
    595                 600                 605

Pro Asp Pro Val Asn Gly Met Val His Val Ile Thr Asp Ile Gln Val
610                 615                 620

Gly Ser Arg Ile Asn Tyr Ser Cys Thr Thr Gly His Arg Leu Ile Gly
625                 630                 635                 640

His Ser Ser Ala Glu Cys Ile Leu Ser Gly Asn Ala Ala His Trp Ser
                645                 650                 655

Thr Lys Pro Pro Ile Cys Gln Arg Ile Pro Cys Gly Leu Pro Pro Thr
            660                 665                 670

Ile Ala Asn Gly Asp Phe Ile Ser Thr Asn Arg Glu Asn Phe His Tyr
        675                 680                 685

Gly Ser Val Val Thr Tyr Arg Cys Asn Pro Gly Ser Gly Gly Arg Lys
    690                 695                 700

Val Phe Glu Leu Val Gly Glu Pro Ser Ile Tyr Cys Thr Ser Asn Asp
705                 710                 715                 720

Asp Gln Val Gly Ile Trp Ser Gly Pro Ala Pro Gln Cys Ile Ile Pro
                725                 730                 735

Asn Lys Cys Thr Pro Pro Asn Val Glu Asn Gly Ile Leu Val Ser Asp
            740                 745                 750

Asn Arg Ser Leu Phe Ser Leu Asn Glu Val Val Glu Phe Arg Cys Gln
        755                 760                 765

Pro Gly Phe Val Met Lys Gly Pro Arg Arg Val Lys Cys Gln Ala Leu
    770                 775                 780

Asn Lys Trp Glu Pro Glu Leu Pro Ser Cys Ser Arg Val Cys Gln Pro
785                 790                 795                 800

Pro Pro Asp Val Leu His Ala Glu Arg Thr Gln Arg Asp Lys Asp Asn
                805                 810                 815

Phe Ser Pro Gly Gln Glu Val Phe Tyr Ser Cys Glu Pro Gly Tyr Asp
            820                 825                 830

Leu Arg Gly Ala Ala Ser Met Arg Cys Thr Pro Gln Gly Asp Trp Ser
        835                 840                 845

Pro Ala Ala Pro Thr Cys Glu Val Lys Ser Cys Asp Asp Phe Met Gly
    850                 855                 860

Gln Leu Leu Asn Gly Arg Val Leu Phe Pro Val Asn Leu Gln Leu Gly
865                 870                 875                 880

Ala Lys Val Asp Phe Val Cys Asp Glu Gly Phe Gln Leu Lys Gly Ser
                885                 890                 895

Ser Ala Ser Tyr Cys Val Leu Ala Gly Met Glu Ser Leu Trp Asn Ser
            900                 905                 910

Ser Val Pro Val Cys Glu Gln Ile Phe Cys Pro Ser Pro Pro Val Ile
        915                 920                 925

Pro Asn Gly Arg His Thr Gly Lys Pro Leu Glu Val Phe Pro Phe Gly
    930                 935                 940

Lys Ala Val Asn Tyr Thr Cys Asp Pro His Pro Asp Arg Gly Thr Ser
945                 950                 955                 960

Phe Asp Leu Ile Gly Glu Ser Thr Ile Arg Cys Thr Ser Asp Pro Gln

```
                965                 970                 975
Gly Asn Gly Val Trp Ser Ser Pro Ala Pro Arg Cys Gly Ile His His
            980                 985                 990
His His His His
        995

<210> SEQ ID NO 14
<211> LENGTH: 2997
<212> TYPE: DNA
<213> ORGANISM: Homo sapiens

<400> SEQUENCE: 14
atgaccgtcg cgcggccgag cgtgcccgcg gcgctgcccc tcctcgggga gctgccccgg      60
ctgctgctgc tggtgctgtt gtgcctgccg gccgtgtggg gtgactgtgg ccttccccca     120
gatgtaccta atgcccagcc agctttggaa ggccgtacaa gttttcccga ggatactgta     180
ataacgtaca atgtgaaga aagctttgtg aaaattcctg cgagaaggga ctcagtgatc      240
tgccttaagg gcagtcaatg gtcagatatt gaagagttct gcaatcgtag ctgcgaggtg     300
ccaacaaggc taaattctgc atccctcaaa cagccttata tcactcagaa ttattttcca     360
gtcggtactg ttgtggaata tgagtgccgt ccaggttaca aagagaaacc ttctctatca     420
ccaaaactaa cttgccttca gaatttaaaa tggtccacag cagtcgaatt ttgtaaaaag     480
aaatcatgcc ctaatccggg agaaatacga atggtcaga ttgatgtacc aggtggcata      540
ttatttggtg caaccatctc cttctcatgt aacacagggt acaaattatt ggctcgact     600 tctagttttt gtcttatttc aggcagctct gtccagtgga gtgacccgtt gccagagtgc     660
agagaaattt attgtccagc accaccacaa attgacaatg aataattca aggggaacgt      720 gaccattatg gatatagaca gtctgtaacg tatgcatgta taaaggatt caccatgatt      780 ggagagcact ctatttattg tactgtgaat aatgatgaag agagtggag tggcccacca      840 cctgaatgct cgagtcctaa caaatgcacg cctccaaatg tggaaaatgg aatattggta     900
tctgacaaca gaagcttatt ttcccttaaat gaagttgtgg agtttaggtg tcagcctggc     960
tttgtcatga aggaccccg ccgtgtgaag tgccaggccc tgaacaaatg ggagccggag      1020
ctaccaagct gctccagggt atgtcagcca cctccagatg tcctgcatgc tgagcgtacc     1080
caaagggaca ggacaacttt tcacctgggg caggaagtgt tctacagctg tgagcccggc     1140
tacgacctca gagggctgc gtctatgcgc tgcacacccc agggagactg gagccctgca     1200
gcccccacat gtgaagtgaa atcctgtgat gacttcatgg ccaacttct taatggccgt     1260 gtgctatttc cagtaaatct ccagcttgga gcaaaagtgg attttgtttg tgatgaagga    1320
tttcaattaa aggcagctc tgctagttac tgtgtcttgg ctggaatgga agcctttgg      1380 aatagcagtg ttccagtgtg tgaacaaatc ttttgtccaa gtcctccagt tattcctaat    1440
gggagacaca caggaaaaacc tctggaagtc tttcccttg gaaaagcagt aaattacaca    1500
tgcgaccccc acccagacag agggacgagc ttcgacctca ttggagagag caccatccgc    1560
tgcacaagtg accctcaagg gaatggggtt tggagcagcc ctgcccctcg ctgtggaatt    1620
ctgggtcact gtcaagcccc agatcatttt ctgtttgcca agttgaaaac ccaaaccaat    1680
gcatctgact ttcccattgg gacatcttta agtacgaat gccgtcctga gtactacggg    1740
aggccattct ctatcacatg tctagataac ctggtctggt caagtccaa agatgtctgt     1800 aaacgtaaat catgtaaaac tcctccagat ccagtgaatg gcatggtgca tgtgatcaca    1860
gacatccagg ttggatccag aatcaactat tcttgtacta cagggcaccg actcattggt    1920
```

```
cactcatctg ctgaatgtat cctctcgggc aatgctgccc attggagcac gaagccgcca  1980
atttgtcaac gaattccttg tgggctaccc cccaccatcg ccaatggaga tttcattagc  2040
accaacagag agaattttca ctatggatca gtggtgacct accgctgcaa tcctggaagc  2100
ggagggagaa aggtgtttga gcttgtgggt gagccctcca tatactgcac cagcaatgac  2160
gatcaagtgg gcatctggag cggcccggcc cctcagtgca ttatacctaa caaatgcacg  2220
cctccaaatg tggaaaatgg aatattggta tctgacaaca gaagcttatt ttccttaaat  2280
gaagttgtgg agtttaggtg tcagcctggc tttgtcatga aggaccccg ccgtgtgaag  2340 tgccaggccc tgaacaaatg ggagccggag ctaccaagct gctccagggt atgtcagcca  2400
cctccagatg tcctgcatgc tgagcgtacc caaagggaca aggacaactt tcacccggg  2460 caggaagtgt tctacagctg tgagcccggc tatgacctca gaggggctgc gtctatgcgc  2520
tgcacacccc agggagactg gagccctgca gcccccacat gtgaagtgaa atcctgtgat  2580
gacttcatgg ccaacttcct taatggccgt gtgctatttc cagtaaatct ccagcttgga  2640
gcaaaagtgg attttgtttg tgatgaagga tttcaattaa aaggcagctc tgctagttat  2700
tgtgtcttgg ctggaatgga aagcctttgg aatagcagtg ttccagtgtg tgaacaaatc  2760
ttttgtccaa gtcctccagt tattcctaat gggagacaca caggaaaaacc tctggaagtc  2820 tttcccttg gaaaagcagt aaattacaca tgcgacccc acccagacag agggacgagc  2880
ttcgacctca ttggagagag caccatccgc tgcacaagtg accctcaagg gaatggggtt  2940
tggagcagcc ctgcccctcg ctgtggaatt catcaccatc accatcacta aagatct  2997
```

<210> SEQ ID NO 15
<211> LENGTH: 1446
<212> TYPE: PRT
<213> ORGANISM: Homo sapiens

<400> SEQUENCE: 15

```
Met Thr Val Ala Arg Pro Ser Val Pro Ala Ala Leu Pro Leu Leu Gly
 1               5                   10                  15

Glu Leu Pro Arg Leu Leu Leu Val Leu Leu Cys Leu Pro Ala Val
            20                  25                  30

Trp Gly Asp Cys Gly Leu Pro Pro Asp Val Pro Asn Ala Gln Pro Ala
        35                  40                  45

Leu Glu Gly Arg Thr Ser Phe Pro Glu Asp Thr Val Ile Thr Tyr Lys
    50                  55                  60

Cys Glu Glu Ser Phe Val Lys Ile Pro Gly Glu Lys Asp Ser Val Ile
65                  70                  75                  80

Cys Leu Lys Gly Ser Gln Trp Ser Asp Ile Glu Glu Phe Cys Asn Arg
                85                  90                  95

Ser Cys Glu Val Pro Thr Arg Leu Asn Ser Ala Ser Leu Lys Gln Pro
            100                 105                 110

Tyr Ile Thr Gln Asn Tyr Phe Pro Val Gly Thr Val Val Glu Tyr Glu
        115                 120                 125

Cys Arg Pro Gly Tyr Arg Arg Glu Pro Ser Leu Ser Pro Lys Leu Thr
    130                 135                 140

Cys Leu Gln Asn Leu Lys Trp Ser Thr Ala Val Glu Phe Cys Lys Lys
145                 150                 155                 160

Lys Ser Cys Pro Asn Pro Gly Glu Ile Arg Asn Gly Gln Ile Asp Val
                165                 170                 175

Pro Gly Gly Ile Leu Phe Gly Ala Thr Ile Ser Phe Ser Cys Asn Thr
```

```
                180                 185                 190
Gly Tyr Lys Leu Phe Gly Ser Thr Ser Ser Phe Cys Leu Ile Ser Gly
            195                 200                 205

Ser Ser Val Gln Trp Ser Asp Pro Leu Pro Glu Cys Arg Glu Ile Tyr
210                 215                 220

Cys Pro Ala Pro Pro Gln Ile Asp Asn Gly Ile Ile Gln Gly Glu Arg
225                 230                 235                 240

Asp His Tyr Gly Tyr Arg Gln Ser Val Thr Tyr Ala Cys Asn Lys Gly
                245                 250                 255

Phe Thr Met Ile Gly Glu His Ser Ile Tyr Cys Thr Val Asn Asn Asp
            260                 265                 270

Glu Gly Glu Trp Ser Gly Pro Pro Glu Cys Ser Ser Pro Asn Lys
                275                 280                 285

Cys Thr Pro Pro Asn Val Glu Asn Gly Ile Leu Val Ser Asp Asn Arg
290                 295                 300

Ser Leu Phe Ser Leu Asn Glu Val Val Glu Phe Arg Cys Gln Pro Gly
305                 310                 315                 320

Phe Val Met Lys Gly Pro Arg Arg Val Lys Cys Gln Ala Leu Asn Lys
                325                 330                 335

Trp Glu Pro Glu Leu Pro Ser Cys Ser Arg Val Cys Gln Pro Pro
                340                 345                 350

Asp Val Leu His Ala Glu Arg Thr Gln Arg Asp Lys Asp Asn Phe Ser
                355                 360                 365

Pro Gly Gln Glu Val Phe Tyr Ser Cys Glu Pro Gly Tyr Asp Leu Arg
            370                 375                 380

Gly Ala Ala Ser Met Arg Cys Thr Pro Gln Gly Asp Trp Ser Pro Ala
385                 390                 395                 400

Ala Pro Thr Cys Glu Val Lys Ser Cys Asp Asp Phe Met Gly Gln Leu
                405                 410                 415

Leu Asn Gly Arg Val Leu Phe Pro Val Asn Leu Gln Leu Gly Ala Lys
            420                 425                 430

Val Asp Phe Val Cys Asp Glu Gly Phe Gln Leu Lys Gly Ser Ser Ala
            435                 440                 445

Ser Tyr Cys Val Leu Ala Gly Met Glu Ser Leu Trp Asn Ser Ser Val
            450                 455                 460

Pro Val Cys Glu Gln Ile Phe Cys Pro Ser Pro Val Ile Pro Asn
465                 470                 475                 480

Gly Arg His Thr Gly Lys Pro Leu Glu Val Phe Pro Phe Gly Lys Ala
                485                 490                 495

Val Asn Tyr Thr Cys Asp Pro His Pro Asp Arg Gly Thr Ser Phe Asp
            500                 505                 510

Leu Ile Gly Glu Ser Thr Ile Arg Cys Thr Ser Asp Pro Gln Gly Asn
            515                 520                 525

Gly Val Trp Ser Ser Pro Ala Pro Arg Cys Gly Ile Leu Gly His Cys
            530                 535                 540

Gln Ala Pro Asp His Phe Leu Phe Ala Lys Leu Lys Thr Gln Thr Asn
545                 550                 555                 560

Ala Ser Asp Phe Pro Ile Gly Thr Ser Leu Lys Tyr Glu Cys Arg Pro
                565                 570                 575

Glu Tyr Tyr Gly Arg Pro Phe Ser Ile Thr Cys Leu Asp Asn Leu Val
            580                 585                 590

Trp Ser Ser Pro Lys Asp Val Cys Lys Arg Lys Ser Cys Lys Thr Pro
            595                 600                 605
```

```
Pro Asp Pro Val Asn Gly Met Val His Val Ile Thr Asp Ile Gln Val
    610                 615                 620

Gly Ser Arg Ile Asn Tyr Ser Cys Thr Thr Gly His Arg Leu Ile Gly
625                 630                 635                 640

His Ser Ser Ala Glu Cys Ile Leu Ser Gly Asn Ala Ala His Trp Ser
                645                 650                 655

Thr Lys Pro Pro Ile Cys Gln Arg Ile Pro Cys Gly Leu Pro Pro Thr
            660                 665                 670

Ile Ala Asn Gly Asp Phe Ile Ser Thr Asn Arg Glu Asn Phe His Tyr
        675                 680                 685

Gly Ser Val Val Thr Tyr Arg Cys Asn Pro Gly Ser Gly Gly Arg Lys
690                 695                 700

Val Phe Glu Leu Val Gly Glu Pro Ser Ile Tyr Cys Thr Ser Asn Asp
705                 710                 715                 720

Asp Gln Val Gly Ile Trp Ser Gly Pro Ala Pro Gln Cys Ile Ile Pro
                725                 730                 735

Asn Lys Cys Thr Pro Pro Asn Val Glu Asn Gly Ile Leu Val Ser Asp
            740                 745                 750

Asn Arg Ser Leu Phe Ser Leu Asn Glu Val Val Glu Phe Arg Cys Gln
        755                 760                 765

Pro Gly Phe Val Met Lys Gly Pro Arg Arg Val Lys Cys Gln Ala Leu
770                 775                 780

Asn Lys Trp Glu Pro Glu Leu Pro Ser Cys Ser Arg Val Cys Gln Pro
785                 790                 795                 800

Pro Pro Asp Val Leu His Ala Glu Arg Thr Gln Arg Asp Lys Asp Asn
                805                 810                 815

Phe Ser Pro Gly Gln Glu Val Phe Tyr Ser Cys Glu Pro Gly Tyr Asp
            820                 825                 830

Leu Arg Gly Ala Ala Ser Met Arg Cys Thr Pro Gln Gly Asp Trp Ser
        835                 840                 845

Pro Ala Ala Pro Thr Cys Glu Val Lys Ser Cys Asp Asp Phe Met Gly
850                 855                 860

Gln Leu Leu Asn Gly Arg Val Leu Phe Pro Val Asn Leu Gln Leu Gly
865                 870                 875                 880

Ala Lys Val Asp Phe Val Cys Asp Glu Gly Phe Gln Leu Lys Gly Ser
                885                 890                 895

Ser Ala Ser Tyr Cys Val Leu Ala Gly Met Glu Ser Leu Trp Asn Ser
            900                 905                 910

Ser Val Pro Val Cys Glu Gln Ile Phe Cys Pro Ser Pro Pro Val Ile
        915                 920                 925

Pro Asn Gly Arg His Thr Gly Lys Pro Leu Glu Val Phe Pro Phe Gly
    930                 935                 940

Lys Ala Val Asn Tyr Thr Cys Asp Pro His Pro Asp Arg Gly Thr Ser
945                 950                 955                 960

Phe Asp Leu Ile Gly Glu Ser Thr Ile Arg Cys Thr Ser Asp Pro Gln
                965                 970                 975

Gly Asn Gly Val Trp Ser Ser Pro Ala Pro Arg Cys Gly Ile Leu Gly
            980                 985                 990

His Cys Gln Ala Pro Asp His Phe Leu Phe Ala Lys Leu Lys Thr Gln
        995                 1000                1005

Thr Asn Ala Ser Asp Phe Pro Ile Gly Thr Ser Leu Lys Tyr Glu Cys
    1010                1015                1020
```

```
Arg Pro Glu Tyr Tyr Gly Arg Pro Phe Ser Ile Thr Cys Leu Asp Asn
1025                1030                1035                1040

Leu Val Trp Ser Ser Pro Lys Asp Val Cys Lys Arg Lys Ser Cys Lys
            1045                1050                1055

Thr Pro Pro Asp Pro Val Asn Gly Met Val His Val Ile Thr Asp Ile
        1060                1065                1070

Gln Val Gly Ser Arg Ile Asn Tyr Ser Cys Thr Thr Gly His Arg Leu
    1075                1080                1085

Ile Gly His Ser Ser Ala Glu Cys Ile Leu Ser Gly Asn Ala Ala His
    1090                1095                1100

Trp Ser Thr Lys Pro Pro Ile Cys Gln Arg Ile Pro Cys Gly Leu Pro
1105                1110                1115                1120

Pro Thr Ile Ala Asn Gly Asp Phe Ile Ser Thr Asn Arg Glu Asn Phe
            1125                1130                1135

His Tyr Gly Ser Val Val Thr Tyr Arg Cys Asn Pro Gly Ser Gly Gly
        1140                1145                1150

Arg Lys Val Phe Glu Leu Val Gly Glu Pro Ser Ile Tyr Cys Thr Ser
    1155                1160                1165

Asn Asp Asp Gln Val Gly Ile Trp Ser Gly Pro Ala Pro Gln Cys Ile
1170                1175                1180

Ile Pro Asn Lys Cys Thr Pro Pro Asn Val Glu Asn Gly Ile Leu Val
1185                1190                1195                1200

Ser Asp Asn Arg Ser Leu Phe Ser Leu Asn Glu Val Val Glu Phe Arg
            1205                1210                1215

Cys Gln Pro Gly Phe Val Met Lys Gly Pro Arg Arg Val Lys Cys Gln
        1220                1225                1230

Ala Leu Asn Lys Trp Glu Pro Glu Leu Pro Ser Cys Ser Arg Val Cys
    1235                1240                1245

Gln Pro Pro Pro Asp Val Leu His Ala Glu Arg Thr Gln Arg Asp Lys
1250                1255                1260

Asp Asn Phe Ser Pro Gly Gln Glu Val Phe Tyr Ser Cys Glu Pro Gly
1265                1270                1275                1280

Tyr Asp Leu Arg Gly Ala Ala Ser Met Arg Cys Thr Pro Gln Gly Asp
            1285                1290                1295

Trp Ser Pro Ala Ala Pro Thr Cys Glu Val Lys Ser Cys Asp Asp Phe
        1300                1305                1310

Met Gly Gln Leu Leu Asn Gly Arg Val Leu Phe Pro Val Asn Leu Gln
    1315                1320                1325

Leu Gly Ala Lys Val Asp Phe Val Cys Asp Glu Gly Phe Gln Leu Lys
1330                1335                1340

Gly Ser Ser Ala Ser Tyr Cys Val Leu Ala Gly Met Glu Ser Leu Trp
1345                1350                1355                1360

Asn Ser Ser Val Pro Val Cys Glu Gln Ile Phe Cys Pro Ser Pro Pro
            1365                1370                1375

Val Ile Pro Asn Gly Arg His Thr Gly Lys Pro Leu Glu Val Phe Pro
        1380                1385                1390

Phe Gly Lys Ala Val Asn Tyr Thr Cys Asp Pro His Pro Asp Arg Gly
    1395                1400                1405

Thr Ser Phe Asp Leu Ile Gly Glu Ser Thr Ile Arg Cys Thr Ser Asp
    1410                1415                1420

Pro Gln Gly Asn Gly Val Trp Ser Ser Pro Ala Pro Arg Cys Gly Ile
1425                1430                1435                1440

His His His His His His
```

1445

<210> SEQ ID NO 16
<211> LENGTH: 4347
<212> TYPE: DNA
<213> ORGANISM: Homo sapiens

<400> SEQUENCE: 16

```
atgaccgtcg cgcggccgag cgtgcccgcg gcgctgcccc tcctcgggga gctgccccgg      60
ctgctgctgc tggtgctgtt gtgcctgccg gccgtgtggg gtgactgtgg ccttccccca     120
gatgtaccta atgcccagcc agctttggaa ggccgtacaa gttttcccga ggatactgta     180
ataacgtaca aatgtgaaga aagctttgtg aaaattcctg gcgagaagga ctcagtgatc     240
tgccttaagg gcagtcaatg gtcagatatt gaagagttct gcaatcgtag ctgcgaggtg     300
ccaacaaggc taaattctgc atccctcaaa cagccttata tcactcagaa ttattttcca     360
gtcggtactg ttgtggaata tgagtgccgt ccaggttaca agagagaacc ttctctatca     420
ccaaaactaa cttgccttca gaatttaaaa tggtccacag cagtcgaatt ttgtaaaaag     480
aaatcatgcc ctaatccggg agaaatacga atggtcaga ttgatgtacc aggtggcata     540
ttatttggtg caaccatctc cttctcatgt aacacagggt acaaattatt ggctcgact      600 tctagttttt gtcttatttc aggcagctct gtccagtgga gtgacccgtt gccagagtgc     660
agagaaattt attgtccagc accaccacaa attgacaatg gaataattca aggggaacgt     720
gaccattatg gatatagaca gtctgtaacg tatgcatgta ataaaggatt caccatgatt     780
ggagagcact ctatttattg tactgtgaat aatgatgaag gagagtggag tggcccacca     840
cctgaatgct cgagtcctaa caaatgcacg cctccaaatg tggaaaatgg aatattggta     900
tctgacaaca aagcttatt ttcccttaaat gaagttgtgg agtttaggtg tcagcctggc     960
tttgtcatga aaggaccccg ccgtgtgaag tgccaggccc tgaacaaatg ggagccggag    1020
ctaccaagct gctccagggt atgtcagcca cctccagatg tcctgcatgc tgagcgtacc    1080
caaagggaca aggacaactt ttcacctggg caggaagtgt tctacagctg tgagcccggc    1140
tacgacctca gagggctgc gtctatgcgc tgcacacccc agggagactg gagccctgca    1200
gcccccacat gtgaagtgaa atcctgtgat gacttcatgg ccaacttct taatggccgt    1260 gtgctatttc agtaaaatct ccagcttgga gcaaaagtgg attttgtttg tgatgaagga    1320
tttcaattaa aaggcagctc tgctagttac tgtgtcttgg ctggaatgga aagcctttgg    1380
aatagcagtg ttccagtgtg tgaacaaatc ttttgtccaa gtcctccagt tattcctaat    1440
gggagacaca caggaaaacc tctggaagtc tttccctttg gaaaagcagt aaattacaca    1500 tgcgacccc acccagacag agggacgagc ttcgacctca ttggagagag caccatccgc    1560
tgcacaagtg accctcaagg gaatgggtt tggagcagcc ctgcccctcg ctgtggaatt    1620
ctgggtcact gtcaagcccc agatcatttt ctgtttgcca agttgaaaac ccaaaccaat    1680
gcatctgact ttcccattgg acatctttta aagtacgaat gccgtcctga gtactacggg    1740
aggccattct ctatcacatg tctagataac ctggtctggt caagtcccaa agatgtctgt    1800
aaacgtaaat catgtaaaac tcctccagat ccagtgaatg gcatggtgca tgtgatcaca    1860
gacatccagg ttggatccag aatcaactat tcttgtacta cagggcaccg actcattggt    1920
cactcatctg ctgaatgtat cctctcgggc aatgctgccc attggagcac gaagccgcca    1980
atttgtcaac gaattccttg tgggctaccc ccaccatcg ccaatggaga tttcattagc    2040
accaacagag agaattttca ctatggatca gtggtgacct accgctgcaa tcctggaagc    2100
```

```
ggagggagaa aggtgtttga gcttgtgggt gagccctcca tatactgcac cagcaatgac    2160
gatcaagtgg gcatctggag cggcccggcc cctcagtgca ttatacctaa caaatgcacg    2220
cctccaaatg tggaaaatgg aatattggta tctgacaaca gaagcttatt ttccttaaat    2280
gaagttgtgg agtttaggtg tcagcctggc tttgtcatga aaggaccccg ccgtgtgaag    2340
tgccaggccc tgaacaaatg ggagccggag ctaccaagct gctccagggt atgtcagcca    2400
cctccagatg tcctgcatgc tgagcgtacc caaagggaca aggacaactt ttacccggg     2460 caggaagtgt tctacagctg tgagcccggc tatgacctca gagggctgc gtctatgcgc     2520 tgcacacccc agggagactg gagccctgca gcccccacat gtgaagtgaa atcctgtgat    2580
gacttcatgg gccaacttct taatggccgt gtgctatttc cagtaaatct ccagcttgga    2640
gcaaaagtgg attttgtttg tgatgaagga tttcaattaa aaggcagctc tgctagttat    2700
tgtgtcttgg ctggaatgga aagcctttgg aatagcagtg ttccagtgtg tgaacaaatc    2760
ttttgtccaa gtcctccagt tattcctaat gggagacaca caggaaaaacc tctggaagtc   2820 tttcccttg gaaaagcagt aaattacaca tgcgaccccc acccagacag agggacgagc     2880
ttcgacctca ttggagagag caccatccgc tgcacaagtg accctcaagg gaatggggtt    2940
tggagcagcc ctgcccctcg ctgtggaatt ctgggtcact gtcaagcccc agatcatttt    3000
ctgtttgcca agttgaaaac ccaaaccaat gcatctgact ttcccattgg gacatcttta    3060
aagtacgaat gccgtcctga gtactacggg aggccattct ctatcacatg tctagataac    3120
ctggtctggt caagtcccaa agatgtctgt aaacgtaaat catgtaaaac tcctccagat    3180
ccagtgaatg gcatggtgca tgtgatcaca gacatccagg ttggatccag aatcaactat    3240
tcttgtacta cagggcaccg actcattggt cactcatctg ctgaatgtat cctctcgggc    3300
aatgctgccc attggagcac gaagccgcca atttgtcaac gaattccttg tgggctaccc    3360
cccaccatcg ccaatggaga tttcattagc accaacagag agaattttca ctatggatca    3420
gtggtgacct accgctgcaa tcctggaagc ggagggagaa aggtgtttga gcttgtgggt    3480
gagccctcca tatactgcac cagcaatgac gatcaagtgg gcatctggag cggcccggcc    3540
cctcagtgca ttatacctaa caaatgcacg cctccaaatg tggaaaatgg aatattggta    3600
tctgacaaca gaagcttatt ttccttaaat gaagttgtgg agtttaggtg tcagcctggc    3660
tttgtcatga aaggaccccg ccgtgtgaag tgccaggccc tgaacaaatg ggagccggag    3720
ctaccaagct gctccagggt atgtcagcca cctccagatg tcctgcatgc tgagcgtacc    3780
caaagggaca aggacaactt ttacccggg caggaagtgt tctacagctg tgagcccggc     3840
tatgacctca gagggctgc gtctatgcgc tgcacacccc agggagactg gagccctgca     3900
gcccccacat gtgaagtgaa atcctgtgat gacttcatgg gccaacttct taatggccgt    3960
gtgctatttc cagtaaatct ccagcttgga gcaaaagtgg attttgtttg tgatgaagga    4020
tttcaattaa aaggcagctc tgctagttat tgtgtcttgg ctggaatgga aagcctttgg    4080
aatagcagtg ttccagtgtg tgaacaaatc ttttgtccaa gtcctccagt tattcctaat    4140
gggagacaca caggaaaaacc tctggaagtc tttcccttg gaaaagcagt aaattacaca    4200
tgcgaccccc acccagacag agggacgagc ttcgacctca ttggagagag caccatccgc    4260
tgcacaagtg accctcaagg gaatggggtt tggagcagcc ctgcccctcg ctgtggaatt    4320
catcaccatc accatcacta aagatct                                        4347

<210> SEQ ID NO 17
```

-continued

<211> LENGTH: 35
<212> TYPE: DNA
<213> ORGANISM: Artificial Sequence
<220> FEATURE:
<223> OTHER INFORMATION: Synthetic primer

<400> SEQUENCE: 17
atatacgaat tctggttgag tccaaatatg gtccc                              35

<210> SEQ ID NO 18
<211> LENGTH: 37
<212> TYPE: DNA
<213> ORGANISM: Artificial Sequence
<220> FEATURE:
<223> OTHER INFORMATION: Synthetic primer

<400> SEQUENCE: 18
acagtgagat ctttatcatt tacccggaga cagggag                            37

<210> SEQ ID NO 19
<211> LENGTH: 771
<212> TYPE: PRT
<213> ORGANISM: Homo Sapiens

<400> SEQUENCE: 19

Met Thr Val Ala Arg Pro Ser Val Pro Ala Ala Leu Pro Leu Leu Gly
 1               5                  10                  15

Glu Leu Pro Arg Leu Leu Leu Val Leu Leu Cys Leu Pro Ala Val
            20                  25                  30

Trp Gly Asp Cys Gly Leu Pro Pro Asp Val Pro Asn Ala Gln Pro Ala
        35                  40                  45

Leu Glu Gly Arg Thr Ser Phe Pro Glu Asp Thr Val Ile Thr Tyr Lys
    50                  55                  60

Cys Glu Glu Ser Phe Val Lys Ile Pro Gly Glu Lys Asp Ser Val Ile
65                  70                  75                  80

Cys Leu Lys Gly Ser Gln Trp Ser Asp Ile Glu Glu Phe Cys Asn Arg
                85                  90                  95

Ser Cys Glu Val Pro Thr Arg Leu Asn Ser Ala Ser Leu Lys Gln Pro
            100                 105                 110

Tyr Ile Thr Gln Asn Tyr Phe Pro Val Gly Thr Val Val Glu Tyr Glu
        115                 120                 125

Cys Arg Pro Gly Tyr Arg Arg Glu Pro Ser Leu Ser Pro Lys Leu Thr
    130                 135                 140

Cys Leu Gln Asn Leu Lys Trp Ser Thr Ala Val Glu Phe Cys Lys Lys
145                 150                 155                 160

Lys Ser Cys Pro Asn Pro Gly Glu Ile Arg Asn Gly Gln Ile Asp Val
                165                 170                 175

Pro Gly Gly Ile Leu Phe Gly Ala Thr Ile Ser Phe Ser Cys Asn Thr
            180                 185                 190

Gly Tyr Lys Leu Phe Gly Ser Thr Ser Ser Phe Cys Leu Ile Ser Gly
        195                 200                 205

Ser Ser Val Gln Trp Ser Asp Pro Leu Pro Glu Cys Arg Glu Ile Tyr
    210                 215                 220

Cys Pro Ala Pro Pro Gln Ile Asp Asn Gly Ile Ile Gln Gly Glu Arg
225                 230                 235                 240

Asp His Tyr Gly Tyr Arg Gln Ser Val Thr Tyr Ala Cys Asn Lys Gly
                245                 250                 255

Phe Thr Met Ile Gly Glu His Ser Ile Tyr Cys Thr Val Asn Asn Asp

```
              260                 265                 270
Glu Gly Glu Trp Ser Gly Pro Pro Glu Cys Ser Ser Pro Asn Lys
            275                 280                 285
Cys Thr Pro Pro Asn Val Glu Asn Gly Ile Leu Val Ser Asp Asn Arg
290                 295                 300
Ser Leu Phe Ser Leu Asn Glu Val Val Glu Phe Arg Cys Gln Pro Gly
305                 310                 315                 320
Phe Val Met Lys Gly Pro Arg Arg Val Lys Cys Gln Ala Leu Asn Lys
                325                 330                 335
Trp Glu Pro Glu Leu Pro Ser Cys Ser Arg Val Cys Gln Pro Pro Pro
                340                 345                 350
Asp Val Leu His Ala Glu Arg Thr Gln Arg Asp Lys Asp Asn Phe Ser
                355                 360                 365
Pro Gly Gln Glu Val Phe Tyr Ser Cys Glu Pro Gly Tyr Asp Leu Arg
            370                 375                 380
Gly Ala Ala Ser Met Arg Cys Thr Pro Gln Gly Asp Trp Ser Pro Ala
385                 390                 395                 400
Ala Pro Thr Cys Glu Val Lys Ser Cys Asp Asp Phe Met Gly Gln Leu
                405                 410                 415
Leu Asn Gly Arg Val Leu Phe Pro Val Asn Leu Gln Leu Gly Ala Lys
                420                 425                 430
Val Asp Phe Val Cys Asp Glu Gly Phe Gln Leu Lys Gly Ser Ser Ala
            435                 440                 445
Ser Tyr Cys Val Leu Ala Gly Met Glu Ser Leu Trp Asn Ser Ser Val
            450                 455                 460
Pro Val Cys Glu Gln Ile Phe Cys Pro Ser Pro Pro Val Ile Pro Asn
465                 470                 475                 480
Gly Arg His Thr Gly Lys Pro Leu Glu Val Phe Pro Phe Gly Lys Ala
                485                 490                 495
Val Asn Tyr Thr Cys Asp Pro His Pro Asp Arg Gly Thr Ser Phe Asp
                500                 505                 510
Leu Ile Gly Glu Ser Thr Ile Arg Cys Thr Ser Asp Pro Gln Gly Asn
            515                 520                 525
Gly Val Trp Ser Ser Pro Ala Pro Arg Cys Gly Ile Leu Val Glu Ser
            530                 535                 540
Lys Tyr Gly Pro Pro Cys Pro Ser Cys Pro Ala Pro Glu Phe Leu Gly
545                 550                 555                 560
Gly Pro Ser Val Phe Leu Phe Pro Pro Lys Pro Lys Asp Thr Leu Met
                565                 570                 575
Ile Ser Arg Thr Pro Glu Val Thr Cys Val Val Val Asp Val Ser Gln
                580                 585                 590
Glu Asp Pro Glu Val Gln Phe Asn Trp Tyr Val Asp Gly Val Glu Val
            595                 600                 605
His Asn Ala Lys Thr Lys Pro Arg Glu Glu Gln Phe Asn Ser Thr Tyr
            610                 615                 620
Arg Val Val Ser Val Leu Thr Val Leu His Gln Asp Trp Leu Asn Gly
625                 630                 635                 640
Lys Glu Tyr Lys Cys Lys Val Ser Asn Lys Gly Leu Pro Ser Ser Ile
                645                 650                 655
Glu Lys Thr Ile Ser Lys Ala Lys Gly Gln Pro Arg Glu Pro Gln Val
                660                 665                 670
Tyr Thr Leu Pro Pro Ser Gln Glu Glu Met Thr Lys Asn Gln Val Ser
            675                 680                 685
```

```
Leu Thr Cys Leu Val Lys Gly Phe Tyr Pro Ser Asp Ile Ala Val Glu
        690                 695                 700

Trp Glu Ser Asn Gly Gln Pro Glu Asp Asn Tyr Lys Thr Thr Pro Pro
705                 710                 715                 720

Val Leu Asp Ser Asp Gly Ser Phe Phe Leu Tyr Ser Arg Leu Thr Val
                725                 730                 735

Asp Lys Ser Arg Trp Gln Glu Gly Asn Val Phe Ser Cys Ser Val Met
                740                 745                 750

His Glu Ala Leu His Asn His Tyr Thr Gln Lys Ser Leu Ser Leu Ser
        755                 760                 765

Pro Gly Lys
    770

<210> SEQ ID NO 20
<211> LENGTH: 2325
<212> TYPE: DNA
<213> ORGANISM: Homo sapiens

<400> SEQUENCE: 20
```

| | | | | | |
|---|---|---|---|---|---|
| atgaccgtcg | cgcggccgag | cgtgcccgcg | gcgctgcccc | tcctcgggga | gctgccccgg | 60 |
| ctgctgctgc | tggtgctgtt | gtgcctgccg | gccgtgtggg | gtgactgtgg | ccttcccca | 120 |
| gatgtaccta | tgcccagcc | agctttggaa | ggcgtacaa | gttttcccga | ggatactgta | 180 |
| ataacgtaca | atgtgaaga | agctttgtg | aaaattcctg | gcgagaagga | ctcagtgatc | 240 |
| tgccttaagg | gcagtcaatg | gtcagatatt | gaagagttct | gcaatcgtag | ctgcgaggtg | 300 |
| ccaacaaggc | taaattctgc | atccctcaaa | cagccttata | tcactcagaa | ttattttcca | 360 |
| gtcggtactg | ttgtggaata | tgagtgccgt | ccaggttaca | gaagagaacc | ttctctatca | 420 |
| ccaaaactaa | cttgccttca | gaatttaaaa | tggtccacag | cagtcgaatt | ttgtaaaaag | 480 |
| aaatcatgcc | ctaatccggg | agaaatacga | atggtcaga | ttgatgtacc | aggtggcata | 540 |
| ttatttggtg | caaccatctc | cttctcatgt | aacacagggt | acaaattatt | tggctcgact | 600 |
| tctagttttt | gtcttatttc | aggcagctct | gtccagtgga | gtgacccgtt | gccagagtgc | 660 |
| agagaaattt | attgtccagc | accaccacaa | attgacaatg | gaataattca | aggggaacgt | 720 |
| gaccattatg | gatatagaca | gtctgtaacg | tatgcatgta | ataaaggatt | caccatgatt | 780 |
| ggagagcact | ctatttattg | tactgtgaat | aatgatgaag | gagagtggag | tggcccacca | 840 |
| cctgaatgct | cgagtcctaa | caaatgcacg | cctccaaatg | tggaaaatgg | aatattggta | 900 |
| tctgacaaca | gaagcttatt | ttccttaaat | gaagttgtgg | agtttaggtg | tcagcctggc | 960 |
| tttgtcatga | aggaccccg | ccgtgtgaag | tgccaggccc | tgaacaaatg | ggagccggag | 1020 |
| ctaccaagct | gctccagggt | atgtcagcca | cctccagatg | tcctgcatgc | tgagcgtacc | 1080 |
| caaagggaca | aggacaactt | tcacctgggc | aggaagtgt | tctacagctg | tgagcccggc | 1140 |
| tacgacctca | gagggctgc | gtctatgcgc | tgcacacccc | aggagactg | gagccctgca | 1200 |
| gcccccacat | gtgaagtgaa | atcctgtgat | gacttcatgg | ccaacttct | taatggccgt | 1260 |
| gtgctatttc | cagtaaatct | ccagcttgga | gcaaagtgg | attttgtttg | tgatgaagga | 1320 |
| tttcaattaa | aaggcagctc | tgctagttac | tgtgtcttgg | ctggaatgga | aagcttttgg | 1380 |
| aatagcagtg | ttccagtgtg | tgaacaaatc | ttttgtccaa | gtcctccagt | tattcctaat | 1440 |
| gggagacaca | caggaaaaacc | tctggaagtc | tttcccttg | gaaaagcagt | aaattacaca | 1500 |
| tgcgaccccc | acccagacag | agggacgagc | ttcgacctca | ttggagagag | caccatccgc | 1560 |

-continued

```
tgcacaagtg accctcaagg gaatggggtt tggagcagcc ctgcccctcg ctgtggaatt    1620
ctggttgagt ccaaatatgg tcccccatgc ccatcatgcc cagcacctga gttcctgggg    1680
ggaccatcag tcttcctgtt ccccccaaaa cccaaggaca ctctcatgat ctcccggacc    1740
cctgaggtca cgtgcgtggt ggtggacgtg agccaggaag accccgaggt ccagttcaac    1800
tggtacgtgg atggcgtgga ggtgcataat gccaagacaa agccgcggga ggagcagttc    1860
aacagcacgt accgtgtggt cagcgtcctc accgtcctgc accaggactg gctgaacggc    1920
aaggagtaca agtgcaaggt ctccaacaaa ggcctcccgt cctccatcga aaaaccatc    1980 tccaaagcca aagggcagcc ccgagagcca caggtgtaca ccctgccccc atcccaggag    2040
gagatgacca agaaccaggt cagcctgacc tgcctggtca aaggcttcta ccccagcgac    2100
atcgccgtgg agtgggagag caatgggcag ccggaggaca actacaagac cacgcctccc    2160
gtgctggact ccgacggctc cttcttcctc tacagcaggc taaccgtgga caagagcagg    2220
tggcaggagg ggaatgtctt ctcatgctcc gtgatgcatg aggctctgca caaccactac    2280
acacagaaga gcctctccct gtctccgggt aaatgataaa gatct                    2325
```

<210> SEQ ID NO 21
<211> LENGTH: 46
<212> TYPE: DNA
<213> ORGANISM: Artificial Sequence
<220> FEATURE:
<223> OTHER INFORMATION: Synthetic primer

<400> SEQUENCE: 21
atatacgaat tctgggtcac tgtgaggagc caccaacatt tgaagc    46

<210> SEQ ID NO 22
<211> LENGTH: 57
<212> TYPE: DNA
<213> ORGANISM: Artificial Sequence
<220> FEATURE:
<223> OTHER INFORMATION: Synthetic primer

<400> SEQUENCE: 22
acagtgagat ctttagtgat ggtgatggtg atgcgacact taagacact ttggaac    57

<210> SEQ ID NO 23
<211> LENGTH: 802
<212> TYPE: PRT
<213> ORGANISM: Homo Sapiens

<400> SEQUENCE: 23

Met Thr Val Ala Arg Pro Ser Val Pro Ala Ala Leu Pro Leu Leu Gly
 1               5                  10                  15

Glu Leu Pro Arg Leu Leu Leu Leu Val Leu Leu Cys Leu Pro Ala Val
            20                  25                  30

Trp Gly Asp Cys Gly Leu Pro Pro Asp Val Pro Asn Ala Gln Pro Ala
        35                  40                  45

Leu Glu Gly Arg Thr Ser Phe Pro Glu Asp Thr Val Ile Thr Tyr Lys
    50                  55                  60

Cys Glu Glu Ser Phe Val Lys Ile Pro Gly Glu Lys Asp Ser Val Ile
65                  70                  75                  80

Cys Leu Lys Gly Ser Gln Trp Ser Asp Ile Glu Glu Phe Cys Asn Arg
                85                  90                  95

Ser Cys Glu Val Pro Thr Arg Leu Asn Ser Ala Ser Leu Lys Gln Pro
            100                 105                 110

```
Tyr Ile Thr Gln Asn Tyr Phe Pro Val Gly Thr Val Glu Tyr Glu
            115                 120                 125

Cys Arg Pro Gly Tyr Arg Glu Pro Ser Leu Ser Pro Lys Leu Thr
130                 135                 140

Cys Leu Gln Asn Leu Lys Trp Ser Thr Ala Val Glu Phe Cys Lys Lys
145                 150                 155                 160

Lys Ser Cys Pro Asn Pro Gly Glu Ile Arg Asn Gly Gln Ile Asp Val
                165                 170                 175

Pro Gly Gly Ile Leu Phe Gly Ala Thr Ile Ser Phe Ser Cys Asn Thr
                180                 185                 190

Gly Tyr Lys Leu Phe Gly Ser Thr Ser Ser Phe Cys Leu Ile Ser Gly
                195                 200                 205

Ser Ser Val Gln Trp Ser Asp Pro Leu Pro Glu Cys Arg Glu Ile Tyr
210                 215                 220

Cys Pro Ala Pro Pro Gln Ile Asp Asn Gly Ile Ile Gln Gly Glu Arg
225                 230                 235                 240

Asp His Tyr Gly Tyr Arg Gln Ser Val Thr Tyr Ala Cys Asn Lys Gly
                245                 250                 255

Phe Thr Met Ile Gly Glu His Ser Ile Tyr Cys Thr Val Asn Asn Asp
            260                 265                 270

Glu Gly Glu Trp Ser Gly Pro Pro Pro Glu Cys Ser Ser Pro Asn Lys
            275                 280                 285

Cys Thr Pro Pro Asn Val Glu Asn Gly Ile Leu Val Ser Asp Asn Arg
            290                 295                 300

Ser Leu Phe Ser Leu Asn Glu Val Val Glu Phe Arg Cys Gln Pro Gly
305                 310                 315                 320

Phe Val Met Lys Gly Pro Arg Arg Val Lys Cys Gln Ala Leu Asn Lys
                325                 330                 335

Trp Glu Pro Glu Leu Pro Ser Cys Ser Arg Val Cys Gln Pro Pro Pro
                340                 345                 350

Asp Val Leu His Ala Glu Arg Thr Gln Arg Asp Lys Asp Asn Phe Ser
            355                 360                 365

Pro Gly Gln Glu Val Phe Tyr Ser Cys Glu Pro Gly Tyr Asp Leu Arg
            370                 375                 380

Gly Ala Ala Ser Met Arg Cys Thr Pro Gln Gly Asp Trp Ser Pro Ala
385                 390                 395                 400

Ala Pro Thr Cys Glu Val Lys Ser Cys Asp Asp Phe Met Gly Gln Leu
                405                 410                 415

Leu Asn Gly Arg Val Leu Phe Pro Val Asn Leu Gln Leu Gly Ala Lys
                420                 425                 430

Val Asp Phe Val Cys Asp Glu Gly Phe Gln Leu Lys Gly Ser Ser Ala
            435                 440                 445

Ser Tyr Cys Val Leu Ala Gly Met Glu Ser Leu Trp Asn Ser Ser Val
            450                 455                 460

Pro Val Cys Glu Gln Ile Phe Cys Pro Ser Pro Val Ile Pro Asn
465                 470                 475                 480

Gly Arg His Thr Gly Lys Pro Leu Glu Val Phe Pro Phe Gly Lys Ala
                485                 490                 495

Val Asn Tyr Thr Cys Asp Pro His Pro Asp Arg Gly Thr Ser Phe Asp
            500                 505                 510

Leu Ile Gly Glu Ser Thr Ile Arg Cys Thr Ser Asp Pro Gln Gly Asn
            515                 520                 525
```

Gly Val Trp Ser Ser Pro Ala Pro Arg Cys Gly Ile Leu Gly His Cys
            530                 535                 540

Glu Glu Pro Pro Thr Phe Glu Ala Met Glu Leu Ile Gly Lys Pro Lys
545                 550                 555                 560

Pro Tyr Tyr Glu Ile Gly Glu Arg Val Asp Tyr Lys Cys Lys Lys Gly
                565                 570                 575

Tyr Phe Tyr Ile Pro Pro Leu Ala Thr His Thr Ile Cys Asp Arg Asn
            580                 585                 590

His Thr Trp Leu Pro Val Ser Asp Asp Ala Cys Tyr Arg Glu Thr Cys
        595                 600                 605

Pro Tyr Ile Arg Asp Pro Leu Asn Gly Gln Ala Val Pro Ala Asn Gly
    610                 615                 620

Thr Tyr Glu Phe Gly Tyr Gln Met His Phe Ile Cys Asn Glu Gly Tyr
625                 630                 635                 640

Tyr Leu Ile Gly Glu Glu Ile Leu Tyr Cys Glu Leu Lys Gly Ser Val
                645                 650                 655

Ala Ile Trp Ser Gly Lys Pro Pro Ile Cys Glu Lys Val Leu Cys Thr
            660                 665                 670

Pro Pro Pro Lys Ile Lys Asn Gly Lys His Thr Phe Ser Glu Val Glu
        675                 680                 685

Val Phe Glu Tyr Leu Asp Ala Val Thr Tyr Ser Cys Asp Pro Ala Pro
    690                 695                 700

Gly Pro Asp Pro Phe Ser Leu Ile Gly Glu Ser Thr Ile Tyr Cys Gly
705                 710                 715                 720

Asp Asn Ser Val Trp Ser Arg Ala Ala Pro Glu Cys Lys Val Val Lys
                725                 730                 735

Cys Arg Phe Pro Val Val Glu Asn Gly Lys Gln Ile Ser Gly Phe Gly
            740                 745                 750

Lys Lys Phe Tyr Tyr Lys Ala Thr Val Met Phe Glu Cys Asp Lys Gly
        755                 760                 765

Phe Tyr Leu Asp Gly Ser Asp Thr Ile Val Cys Asp Ser Asn Ser Thr
    770                 775                 780

Trp Asp Pro Pro Val Pro Lys Cys Leu Lys Val Ser His His His His
785                 790                 795                 800

His His

<210> SEQ ID NO 24
<211> LENGTH: 2415
<212> TYPE: DNA
<213> ORGANISM: Homo sapiens

<400> SEQUENCE: 24
atgaccgtcg cgcggccgag cgtgcccgcg gcgctgcccc tcctcgggga gctgccccgg    60
ctgctgctgc tggtgctgtt gtgcctgccg gccgtgtggg gtgactgtgg ccttccccca   120
gatgtaccta atgcccagcc agctttggaa ggccgtacaa gttttcccga ggatactgta   180
ataacgtaca atgtgaaga aagctttgtg aaaattcctg gcgagaagga ctcagtgatc   240
tgccttaagg gcagtcaatg gtcagatatt gaagagttct gcaatcgtag ctgcgaggtg   300
ccaacaaggc taaattctgc atccctcaaa cagccttata tcactcagaa ttattttcca   360
gtcggtactg ttgtggaata tgagtgccgt ccaggttaca agagagaacc ttctctatca   420
ccaaaactaa cttgccttca gaattttaaa tggtccacag cagtcgaatt ttgtaaaaag   480
aaatcatgcc ctaatccggg agaaatacga atggtcaga ttgatgtacc aggtggcata   540

```
ttatttggtg caaccatctc cttctcatgt aacacagggt acaaattatt tggctcgact    600
tctagttttt gtcttatttc aggcagctct gtccagtgga gtgacccgtt gccagagtgc    660
agagaaattt attgtccagc accaccacaa attgacaatg aataattca aggggaacgt    720
gaccattatg gatatagaca gtctgtaacg tatgcatgta ataaaggatt caccatgatt    780
ggagagcact ctatttattg tactgtgaat aatgatgaag gagagtggag tggcccacca    840
cctgaatgct cgagtcctaa caaatgcacg cctccaaatg tggaaaatgg aatattggta    900
tctgacaaca gaagcttatt ttccttaaat gaagttgtgg agtttaggtg tcagcctggc    960
tttgtcatga aggaccccg ccgtgtgaag tgccaggccc tgaacaaatg ggagccggag    1020
ctaccaagct gctccagggt atgtcagcca cctccagatg tcctgcatgc tgagcgtacc    1080
caaagggaca aggacaactt ttcacctggg caggaagtgt tctacagctg tgagcccggc    1140
tacgacctca gagggctgc gtctatgcgc tgcacacccc agggagactg gagccctgca    1200
gcccccacat gtgaagtgaa atcctgtgat gacttcatgg ccaacttcct taatggccgt    1260
gtgctatttc cagtaaatct ccagcttgga gcaaaagtgg attttgtttg tgatgaagga    1320
tttcaattaa aaggcagctc tgctagttac tgtgtcttgg ctggaatgga aagccttttgg  1380
aatagcagtg ttccagtgtg tgaacaaatc ttttgtccaa gtcctccagt tattcctaat    1440
gggagacaca caggaaaaacc tctggaagtc tttcccttg gaaaagcagt aaattacaca    1500
tgcgaccccc acccagacag agggacgagc ttcgacctca ttggagagag caccatccgc    1560
tgcacaagtg accctcaagg gaatgggggtt tggagcagcc ctgcccctcg ctgtggaatt    1620
ctgggtcact gtgaggagcc accaacattt gaagctatgg agctcattgg taaaccaaaa    1680
ccctactatg agattggtga acgagtagat tataagtgta aaaaaggata cttctatata    1740
cctcctcttg ccacccatac tatttgtgat cggaatcata catggctacc tgtctcagat    1800
gacgcctgtt atagagaaac atgtccatat atacgggatc ctttaaatgg ccaagcagtc    1860
cctgcaaatg ggacttacga gtttggttat cagatgcact ttatttgtaa tgagggttat    1920
tacttaattg gtgaagaaat tctatattgt gaacttaaag gatcagtagc aatttggagc    1980
ggtaagcccc caatatgtga aaaggttttg tgtacaccac ctccaaaaat aaaaaatgga    2040
aaacacacct ttagtgaagt agaagtattt gagtatcttg atgcagtaac ttatagttgt    2100
gatcctgcac ctggaccaga tccatttttca cttattggag agagcacgat ttattgtggt    2160
gacaattcag tgtggagtcg tgctgctcca gagtgtaaag tggtcaaatg tcgatttcca    2220
gtagtcgaaa atgaaaaaca gatatcagga tttggaaaaa aattttacta caaagcaaca    2280
gttatgtttg aatgcgataa gggttttttac ctcgatggca gcgacacaat tgtctgtgac    2340
agtaacagta cttgggatcc cccagttcca aagtgtctta agtgtcgca tcaccatcac    2400
catcactaaa gatct                                                    2415
```

<210> SEQ ID NO 25
<211> LENGTH: 16
<212> TYPE: PRT
<213> ORGANISM: Artificial Sequence
<220> FEATURE:
<223> OTHER INFORMATION: Synthetic lipid tail sequence

<400> SEQUENCE: 25

Gly Ser Ser Lys Ser Pro Ser Lys Lys Lys Lys Lys Lys Pro Gly Asp
 1               5                  10                  15

```
<210> SEQ ID NO 26
<211> LENGTH: 14
<212> TYPE: PRT
<213> ORGANISM: Homo sapiens

<400> SEQUENCE: 26

Val Ser Thr Ser Ser Thr Thr Lys Pro Ala Ser Ser Ala Ser
 1               5                  10

<210> SEQ ID NO 27
<211> LENGTH: 13
<212> TYPE: PRT
<213> ORGANISM: Homo sapiens

<400> SEQUENCE: 27

Gly Pro Arg Pro Thr Tyr Lys Pro Pro Val Ser Asn Pro
 1               5                  10

<210> SEQ ID NO 28
<211> LENGTH: 16
<212> TYPE: PRT
<213> ORGANISM: Homo sapiens

<400> SEQUENCE: 28

Thr Tyr Leu Thr Asp Glu Thr His Arg Glu Cys Lys Phe Thr Ser Leu
 1               5                  10                  15

<210> SEQ ID NO 29
<211> LENGTH: 23
<212> TYPE: PRT
<213> ORGANISM: Homo sapiens

<400> SEQUENCE: 29

Lys Ala Asp Gly Gly Ala Glu Tyr Ala Thr Tyr Gln Thr Lys Ser Thr
 1               5                  10                  15

Thr Pro Ala Glu Gln Arg Cys
                20

<210> SEQ ID NO 30
<211> LENGTH: 9
<212> TYPE: PRT
<213> ORGANISM: Artificial Sequence
<220> FEATURE:
<223> OTHER INFORMATION: Synthetic peptide

<400> SEQUENCE: 30

Ser Ser Pro Ala Pro Arg Cys Gly Ile
 1               5

<210> SEQ ID NO 31
<211> LENGTH: 6
<212> TYPE: PRT
<213> ORGANISM: Artificial Sequence
<220> FEATURE:
<223> OTHER INFORMATION: Synthetic 6xHis tag

<400> SEQUENCE: 31

His His His His His His
 1               5

<210> SEQ ID NO 32
<211> LENGTH: 5
<212> TYPE: PRT
<213> ORGANISM: Homo sapiens
```

-continued

```
<400> SEQUENCE: 32

Ile Ile Pro Asn Lys
  1             5

<210> SEQ ID NO 33
<211> LENGTH: 5
<212> TYPE: PRT
<213> ORGANISM: Homo sapiens

<400> SEQUENCE: 33

Ser Ser Pro Asn Lys
  1             5

<210> SEQ ID NO 34
<211> LENGTH: 4
<212> TYPE: PRT
<213> ORGANISM: Artificial Sequence
<220> FEATURE:
<223> OTHER INFORMATION: Synthetic peptide

<400> SEQUENCE: 34

Gly Ile Leu Val
  1

<210> SEQ ID NO 35
<211> LENGTH: 5
<212> TYPE: PRT
<213> ORGANISM: Homo sapiens

<400> SEQUENCE: 35

Gly Ile Leu Gly His
  1             5
```